United States Patent

Eppstein et al.

[11] Patent Number: 6,142,939
[45] Date of Patent: *Nov. 7, 2000

[54] MICROPORATION OF HUMAN SKIN FOR DRUG DELIVERY AND MONITORING APPLICATIONS

[75] Inventors: Jonathan A. Eppstein, Atlanta; Michael R. Hatch, Sugar Hills; Difei Yang, Chamblee, all of Ga.

[73] Assignees: SpectRx, Inc., Norcross; Altea Technologies, Inc., Atlanta, both of Ga.

[*] Notice: This patent is subject to a terminal disclaimer.

[21] Appl. No.: 09/208,166

[22] Filed: Dec. 9, 1998

Related U.S. Application Data

[63] Continuation of application No. 08/776,863, Sep. 5, 1997, Pat. No. 5,885,211, which is a continuation-in-part of application No. 08/520,547, Aug. 29, 1995, abandoned, which is a continuation-in-part of application No. 08/152,442, Nov. 15, 1993, Pat. No. 5,458,140, and application No. 08/152,174, Dec. 8, 1993, Pat. No. 5,445,611.

[60] Provisional application No. 60/008,043, Oct. 30, 1995.

[51] Int. Cl.⁷ .................................................. A61B 5/00
[52] U.S. Cl. ..................... 600/309; 600/365; 600/573; 601/2; 604/290; 606/9; 606/131; 607/96
[58] Field of Search ........................... 600/309, 310, 600/316, 365, 573, 476; 601/2, 3; 607/96, 100, 104; 604/22, 20, 49, 289, 290; 606/9, 131

[56] References Cited

U.S. PATENT DOCUMENTS

| | | | |
|---|---|---|---|
| 4,775,361 | 10/1988 | Jacques et al. | 604/20 |
| 4,844,098 | 7/1989 | Mitchen | 128/765 |
| 4,860,743 | 8/1989 | Abela | 182/303 |

(List continued on next page.)

FOREIGN PATENT DOCUMENTS

| | | |
|---|---|---|
| (11)259351A1 | 8/1988 | Germany . |
| WO 92/00106 | 1/1992 | WIPO . |
| WO94/09713 | 5/1994 | WIPO . |
| WO 95/10223 | 4/1995 | WIPO . |
| WO 97/04832 | 2/1997 | WIPO . |

OTHER PUBLICATIONS

Conference of IEEE Engineering in Medicine and Biology Society, eld 10/31–11/3/96 –Publication "Development of Micro Electrothermal Branding Tools for Embryo Labeling", by Lin Wang, David J. Beebe, Allen R. Williams and Kim D. Easley.

"Ultraviolet–Laser Ablation of Skin" Lane et al. 121 Arch. Dermatol., 609–617 (1985).

"Controlled Removal of Human Stratum Corneum by Pulsed Laser" Jacques et al., 88 J. Invest. Dermatol., 88–93 (1987).

(List continued on next page.)

*Primary Examiner*—Ruth S. Smith
*Attorney, Agent, or Firm*—Needle & Rosenberg, P.C.

[57] ABSTRACT

A method of enhancing the permeability of the skin to an analyte for diagnostic purposes or to a drug for therapeutic purposes is described utilizing microporation and optionally sonic energy and a chemical enhancer. If selected, the sonic energy may be modulated by means of frequency modulation, amplitude modulation, phase modulation, and/or combinations thereof. Microporation is accomplished by (a) ablating the stratum corneum by localized rapid heating of water such that such water is vaporized, thus eroding the cells; (b) puncturing the stratum corneum with a microlancet calibrated to form a micropore of up to about 1000 μm in diameter; (c) ablating the stratum corneum by focusing a tightly focused beam of sonic energy onto the stratum corneum; (d) hydraulically puncturing the stratum corneum with a high pressure jet of fluid to form a micropore of up to about 1000 μm in diameter, or (e) puncturing the stratum corneum with short pulses of electricity to form a micropore of up to about 1000 μm in diameter. A dye with an absorption maximum matched to the wavelength of a pulsed light source can be absorbed into the stratum corneum to concentrate the energy of the pulsed light source and aid in ablation of the stratum corneum. Alternatively, a hot wire can be caused to contact the stratum corneum.

33 Claims, 33 Drawing Sheets

U.S. PATENT DOCUMENTS

| | | | |
|---|---|---|---|
| 5,003,987 | 4/1991 | Grinwald | 128/734 |
| 5,016,615 | 5/1991 | Driller et al. | 128/24 |
| 5,019,034 | 5/1991 | Weaver et al. | 604/20 |
| 5,041,109 | 8/1991 | Abela | 606/15 |
| 5,092,864 | 3/1992 | Hayes et al. | 606/10 |
| 5,115,805 | 5/1992 | Bommannan et al. | 128/24 |
| 5,139,023 | 8/1992 | Stanley et al. | 128/637 |
| 5,190,558 | 3/1993 | Ito | 606/131 |
| 5,226,907 | 7/1993 | Tankovich | 606/133 |
| 5,246,437 | 9/1993 | Abela | 606/5 |
| 5,267,985 | 12/1993 | Shimada et al. | 128/24.1 |
| 5,323,769 | 6/1994 | Bommannan et al. | 601/2 |
| 5,423,803 | 6/1995 | Tankovich et al. | 606/9 |
| 5,425,728 | 6/1995 | Tankovich | 606/9 |
| 5,445,611 | 8/1995 | Eppstein et al. | 604/49 |
| 5,458,140 | 10/1995 | Eppstein et al. | 128/632 |
| 5,554,153 | 9/1996 | Costello et al. | 606/9 |
| 5,885,211 | 3/1999 | Eppstein et al. | 600/309 |

OTHER PUBLICATIONS

"Dermabrasion, Chemabrasion, and Laserbrasion" James E. Fulton, Jr., MD, Amer. Soc. For Dermatologic Surgery (1996) 619–628.

"Pulse Duration Dependence for Laser Photothermal Imaging Media" Hare et al., Soc. For Imaging Science and Technology (1997).

"Preparation of Isolated Sheets of Human Stratum Corneum" Kligman et al., 88 Arch. Dermatol. (1963) 702–705.

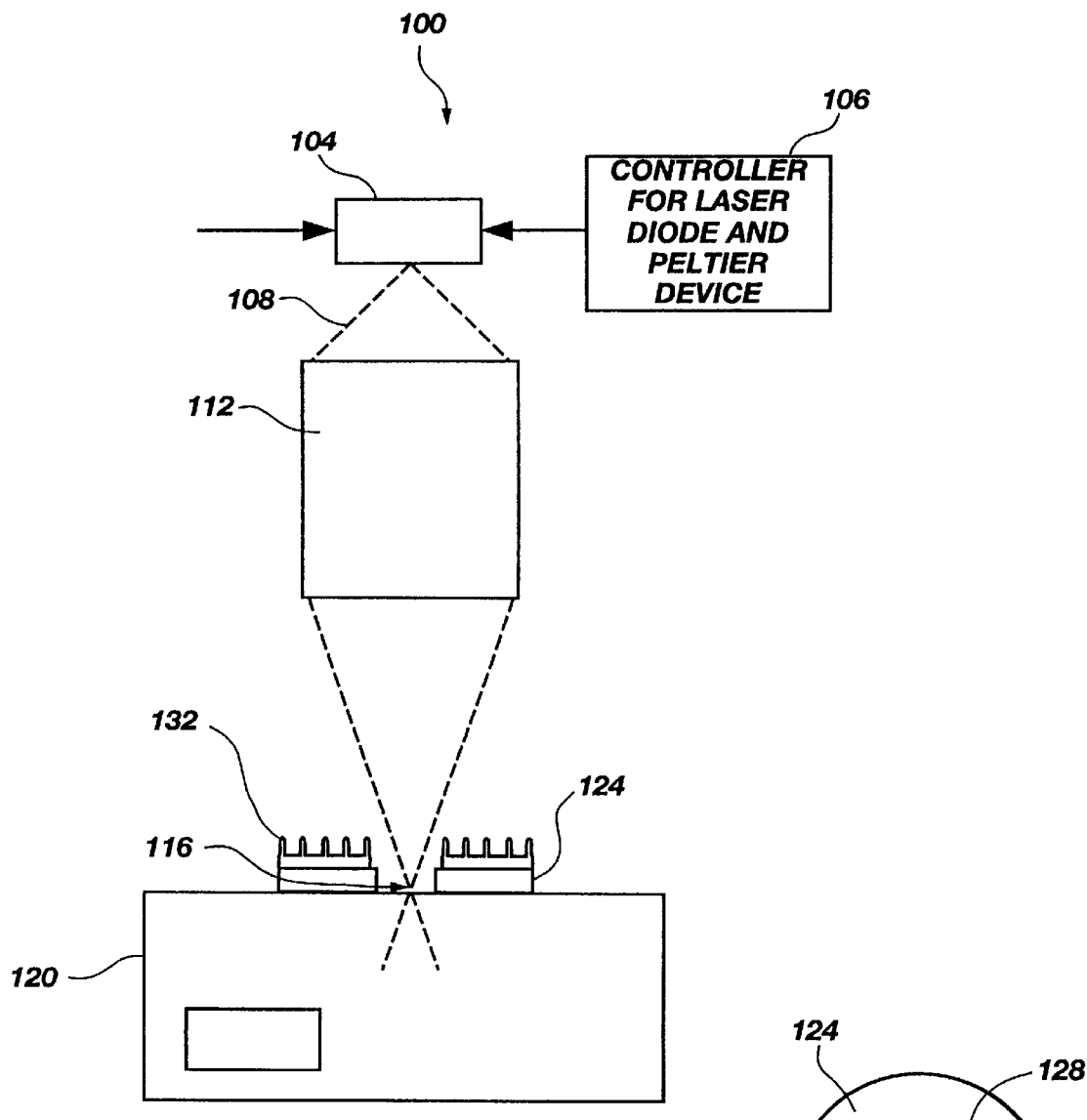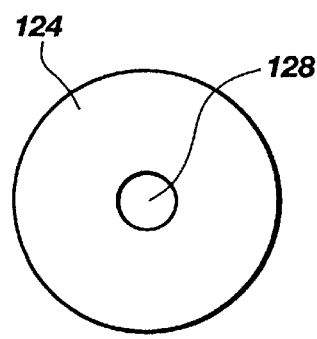
Fig. 3A
Fig. 3B

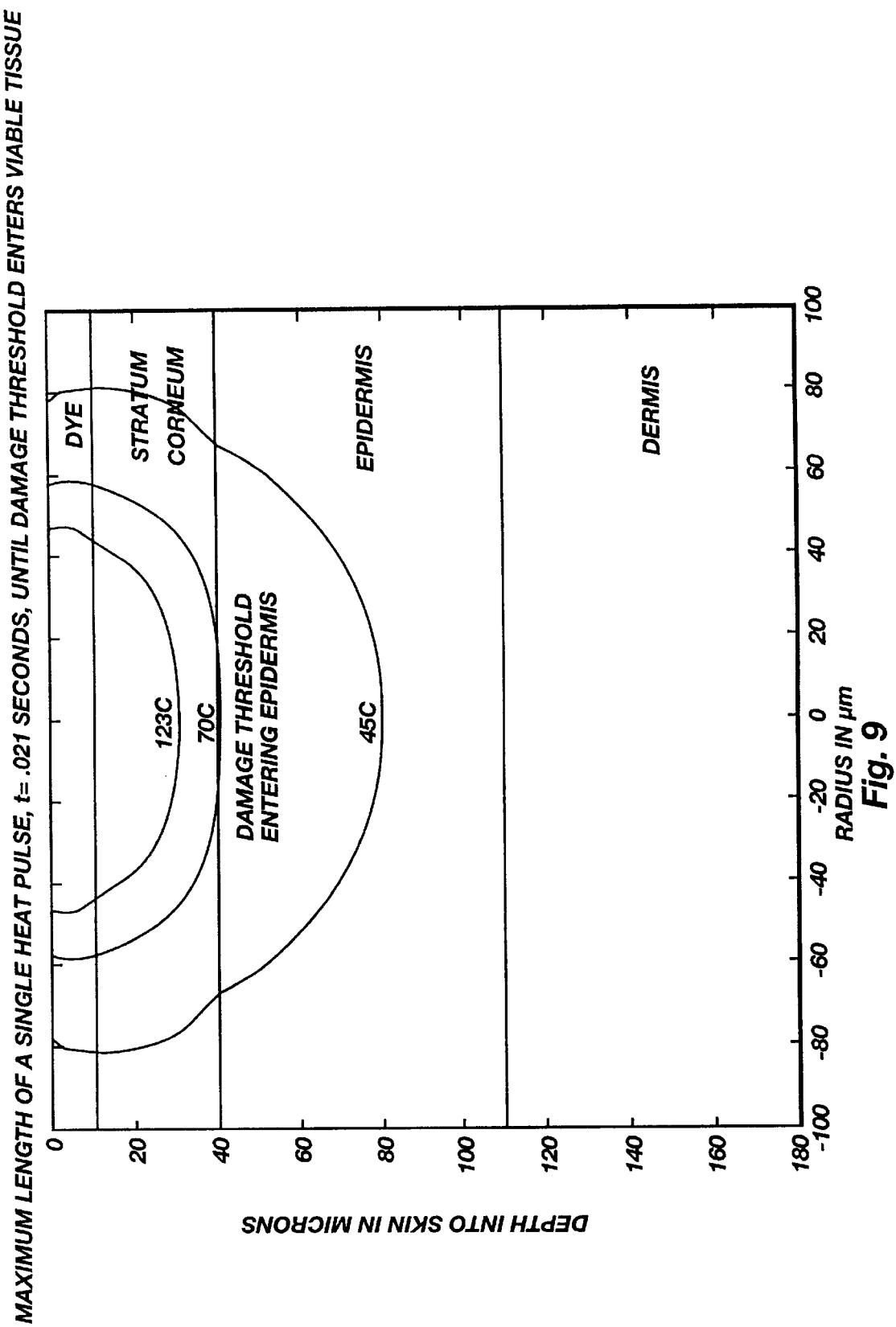

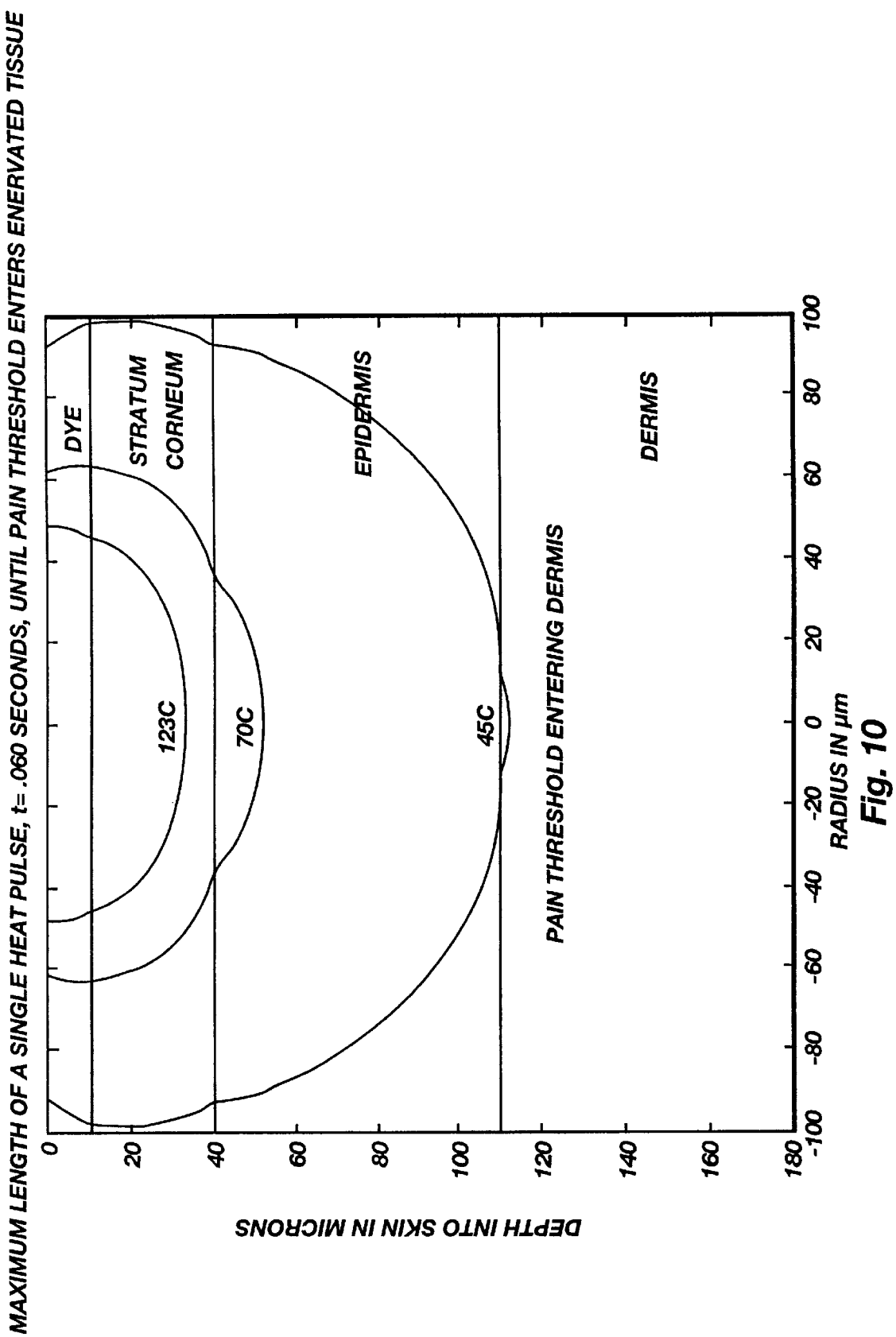

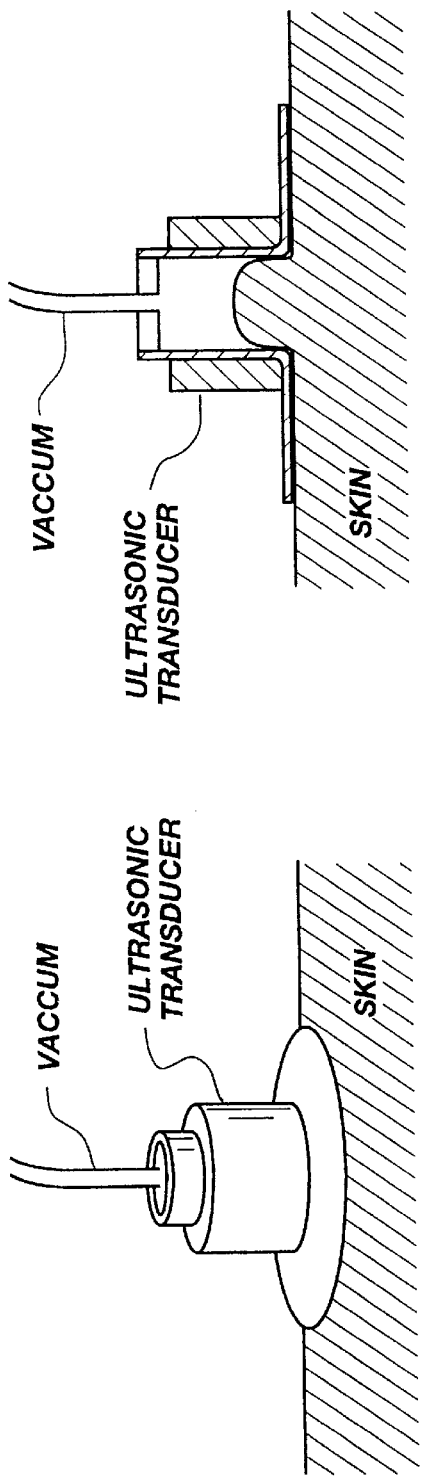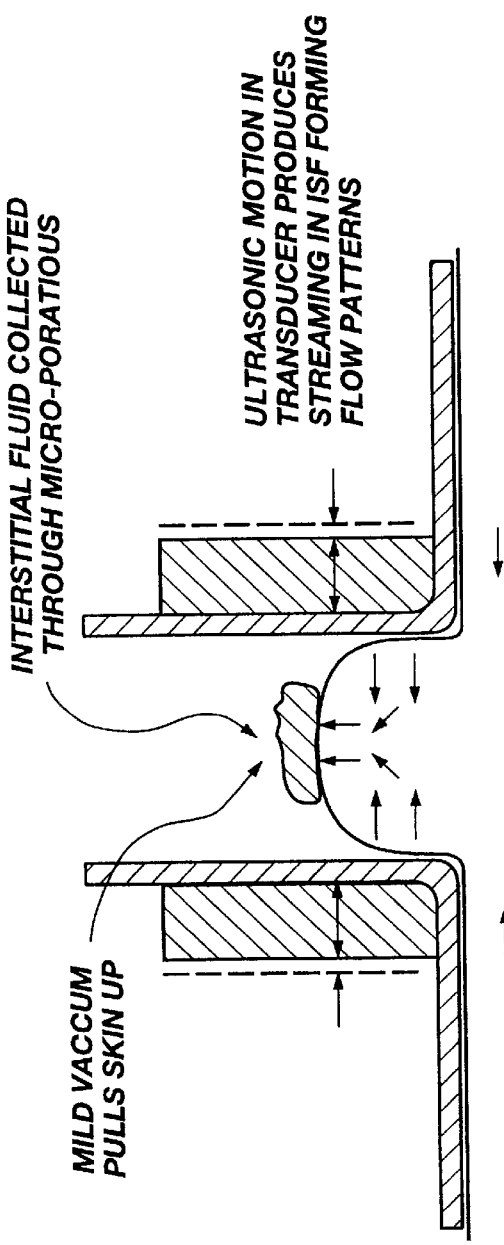
Fig. 31
Fig. 32
Fig. 33

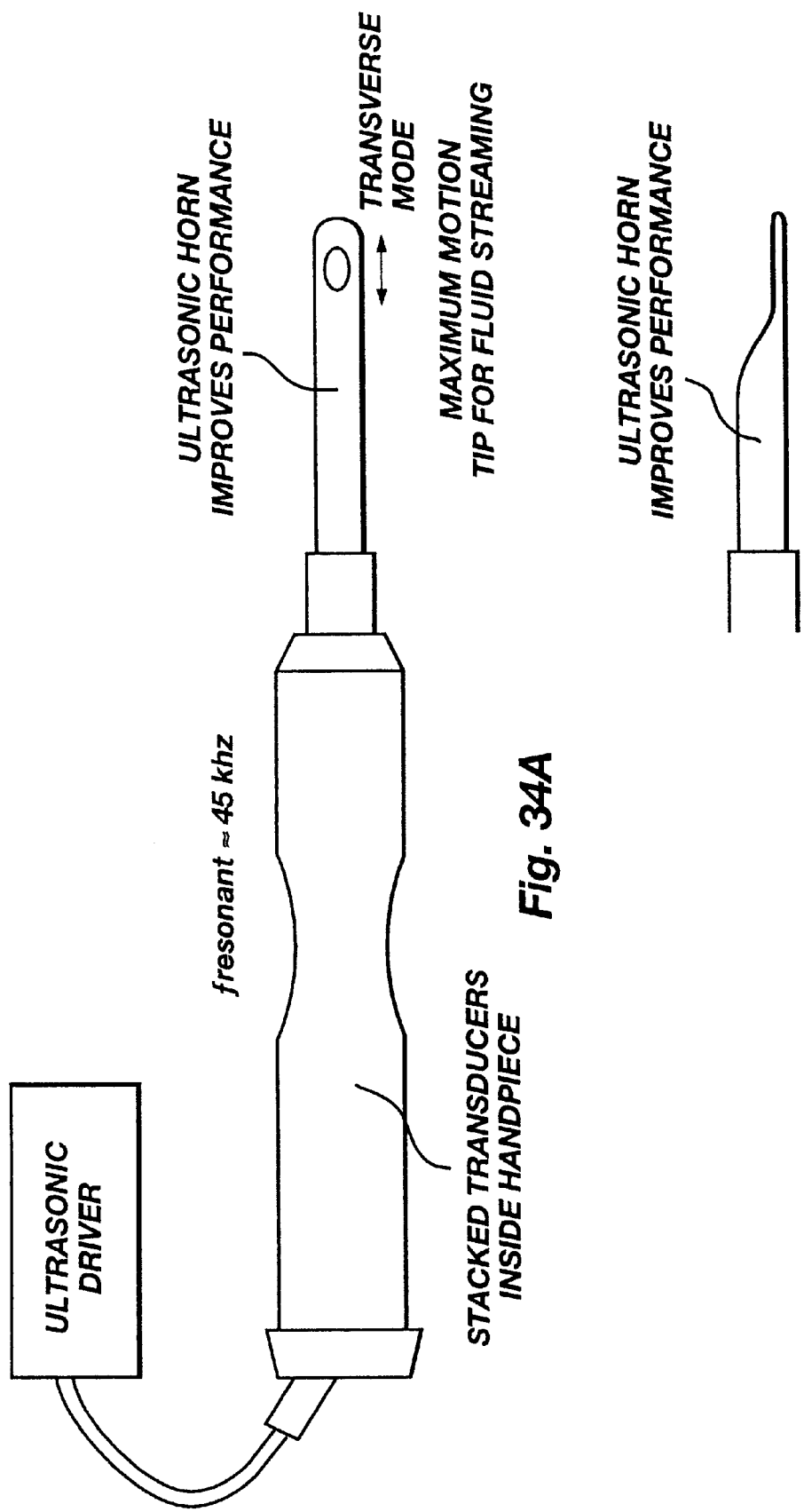

MICROPORATION OF HUMAN SKIN FOR DRUG DELIVERY AND MONITORING APPLICATIONS

CROSS-REFERENCE TO RELATED APPLICATIONS

This application is a continuation of U.S. application Ser. No. 08/776,863, filed Sep. 5, 1997, now U.S. Pat. No. 5,885,211, which is a continuation-in-part of application Ser. No. 08/520,547, filed Aug. 29, 1995, now abandoned, which is a continuation-in-part of Serial No. 08/152,442, filed Nov. 15, 1993, now U.S. Pat. No. 5,458,140, and of Ser. No. 08/152,174, filed Dec. 8, 1993, now U.S. Pat. No. 5,445,611; this application also claims the benefit of U.S. Provisional Application No. 60/008,043, filed Oct. 30, 1995.

BACKGROUND OF THE INVENTION

This invention relates generally to the field of monitoring of analytes in the body and the transdermal delivery of drugs to the body. More particularly, this invention relates to a minimally invasive to non-invasive method of increasing the permeability of the skin through microporation of the stratum corneum, which can be combined with sonic energy, chemical permeation enhancers, pressure, and the like for selectively enhancing outward flux of analytes from the body for monitoring thereof or the delivery of drugs into the body.

The stratum corneum is chiefly responsible for the well known barrier properties of skin. Thus, it is this layer that presents the greatest barrier to transdermal flux of drugs or other molecules into the body and of analytes out of the body. The stratum corneum, the outer horny layer of the skin, is a complex structure of compact keratinized cell remnants separated by lipid domains. Compared to the oral or gastric mucosa, the stratum corneum is much less permeable to molecules either external or internal to the body. The stratum corneum is formed from keratinocytes, which comprise the majority of epidermal cells, that lose their nuclei and become corneocytes. These dead cells comprise the stratum corneum, which has a thickness of only about 10–30 $\mu$m and, as noted above, is a very resistant waterproof membrane that protects the body from invasion by exterior substances and the outward migration of fluids and dissolved molecules. The stratum corneum is continuously renewed by shedding of corneum cells during desquamation and the formation of new corneum cells by the keratinization process.

The flux of a drug or analyte across the skin can be increased by changing either the resistance (the diffusion coefficient) or the driving force (the gradient for diffusion). Flux may be enhanced by the use of so-called penetration or chemical enhancers. Chemical enhancers are well known in the art and a more detailed description will follow.

Another method of increasing the permeability of skin to drugs is iontophoresis. Iontophoresis involves the application of an external electric field and topical delivery of an ionized form of drug or an un-ionized drug carried with the water flux associated with ion transport (electro-osmosis). While permeation enhancement with iontophoresis has been effective, control of drug delivery and irreversible skin damage are problems associated with the technique.

Sonic energy has also been used to enhance permeability of the skin and synthetic membranes to drugs and other molecules. Ultrasound has been defined as mechanical pressure waves with frequencies above 20 kHz, H. Lutz et al., *Manual of Ultrasound* 3–12 (1984). Sonic energy is generated by vibrating a piezoelectric crystal or other electromechanical element by passing an alternating current through the material, R. Brucks et al., 6 *Pharm. Res.* 697 (1989). The use of sonic energy to increase the permeability of the skin to drug molecules has been termed sonophoresis or phonophoresis.

Although it has been acknowledged that enhancing permeability of the skin should theoretically make it possible to transport molecules from inside the body through the skin to outside the body for collection or monitoring, practicable methods have not been disclosed. U.S. Pat. No. 5,139,023 to Stanley et al. discloses an apparatus and method for noninvasive blood glucose monitoring. In this invention, chemical permeation enhancers are used to increase the permeability of mucosal tissue or skin to glucose. Glucose then passively diffuses through the mucosal tissue or skin and is captured in a receiving medium. The amount of glucose in the receiving medium is measured and correlated to determine the blood glucose level. However, as taught in Stanley et al., this method is much more efficient when used on mucosal tissue, such as buccal tissue, which results in detectable amounts of glucose being collected in the receiving medium after a lag time of about 10–20 minutes. However, the method taught by Stanley et al. results in an extremely long lag time, ranging from 2 to 24 hours depending on the chemical enhancer composition used, before detectable amounts of glucose can be detected diffusing through human skin (heat-separated epidermis) in vitro. These long lag times may be attributed to the length of time required for the chemical permeation enhancers to passively diffuse through the skin and to enhance the permeability of the barrier stratum corneum, as well as the length of time required for the glucose to passively diffuse out through the skin. Thus, Stanley et al. clearly does not teach a method for transporting blood glucose or other analytes non-invasively through the skin in a manner that allows for rapid monitoring, as is required for blood glucose monitoring of diabetic patients and for many other body analytes such blood electrolytes.

While the use of sonic energy for drug delivery is known, results have been largely disappointing in that enhancement of permeability has been relatively low. There is no consensus on the efficacy of sonic energy for increasing drug flux across the skin. While some studies report the success of sonophoresis, J. Davick et al., 68 *Phys. Ther.* 1672 (1988); J. Griffin et al., 47 *Phys. Ther.* 594 (1967); J. Griffin & J. Touchstone, 42 *Am. J. Phys. Med.* 77 (1963); J. Griffin et al., 44 *Am. J. Phys. Med.* 20 (1965); D. Levy et al., 83 *J. Clin. Invest.* 2074); D. Bommannan et al., 9 *Pharm. Res.* 559 (1992), others have obtained negative results, H. Benson et al., 69 *Phys. Ther.* 113 (1988); J. McElnay et al., 20 *Br. J. Clin. Pharmacol.* 4221 (1985); H. Pratzel et al., 13 *J. Rheumatol.* 1122 (1986). Systems in which rodent skin were employed showed the most promising results, whereas systems in which human skin was employed have generally shown disappointing results. It is well known to those skilled in the art that rodent skin is much more permeable than human skin, and consequently the above results do not teach one skilled in the art how to effectively utilize sonophoresis as applied to transdermal delivery and/or monitoring through human skin.

A significant improvement in the use of ultrasonic energy in the monitoring of analytes and also in the delivery of drugs to the body is disclosed and claimed in copending applications Ser. No. 08/152,442 filed Nov. 15, 1993, now U.S. Pat. No. 5,458,140, and Ser. No. 08/152,174 filed Dec. 8, 1993, now U.S. Pat. No. 5,445,611, both of which are incorporated herein by reference. In these inventions, the transdermal sampling of an analyte or the transdermal delivery of drugs, is accomplished through the use of sonic energy that is modulated in intensity, phase, or frequency or a combination of these parameters coupled with the use of chemical permeation enhancers. Also disclosed is the use of sonic energy, optionally with modulations of frequency, intensity, and/or phase, to controllably push and/or pump molecules through the stratum corneum via perforations introduced by needle puncture, hydraulic jet, laser, electroporation, or other methods.

The formation of micropores (i.e. microporation) in the stratum corneum to enhance the delivery of drugs has been the subject of various studies and has resulted in the issuance of patents for such techniques.

Jacques et al., 88 *J. Invest. Dermatol.* 88–93 (1987), teaches a method of administering a drug by ablating the stratum corneum of a region of the skin using pulsed laser light of wavelength, pulse length, pulse energy, pulse number, and pulse repetition rate sufficient to ablate the stratum corneum without significantly damaging the underlying epidermis and then applying the drug to the region of ablation. This work resulted in the issuance of U.S. Pat. No. 4,775,361 to Jacques et al. The ablation of skin through the use of ultraviolet-laser irradiation was earlier reported by Lane et al., 121 *Arch. Dermatol.* 609–617 (1985). Jacques et al. is restricted to use of few wavelengths of light and expensive lasers.

Tankovich, U.S. Pat. No. 5,165,418 (hereinafter, "Tankovich '418"), discloses a method of obtaining a blood sample by irradiating human or animal skin with one or more laser pulses of sufficient energy to cause the vaporization of skin tissue so as to produce a hole in the skin extending through the epidermis and to sever at least one blood vessel, causing a quantity of blood to be expelled through the hole such that it can be collected. Tankovich '418 thus is inadequate for noninvasive or minimally invasive permeabilization of the stratum corneum such that a drug can be delivered to the body or an analyte from the body can be analyzed.

Tankovich et al., U.S. Pat. No. 5,423,803 (hereinafter, "Tankovich '803") discloses a method of laser removal of superficial epidermal skin cells in human skin for cosmetic applications. The method comprises applying a light-absorbing "contaminant" to the outer layers of the epidermis and forcing some of this contaminant into the intercellular spaces in the stratum corneum, and illuminating the infiltrated skin with pulses of laser light of sufficient intensity that the amount of energy absorbed by the contaminant will cause the contaminant to explode with sufficient energy to tear off some of the epidermal skin cells. Tankovich '803 further teaches that there should be high absorption of energy by the contaminant at the wavelength of the laser beam, that the laser beam must be a pulsed beam of less than 1 $\mu$s duration, that the contaminant must be forced into the upper layers of the epidermis, and that the contaminant must explode with sufficient energy to tear off epidermal cells upon absorption of the laser energy. This invention also fails to disclose or suggest a method of drug delivery or analyte collection.

Raven et al., WO 92/00106, describes a method of selectively removing unhealthy tissue from a body by administering to a selected tissue a compound that is highly absorbent of infrared radiation of wavelength 750–860 nm and irradiating the region with corresponding infrared radiation at a power sufficient to cause thermal vaporization of the tissue to which the compound was administered but insufficient to cause vaporization of tissue to which the compound had not been administered. The absorbent compound should be soluble in water or serum, such as indocyanine green, chlorophyll, porphyrins, heme-containing compounds, or compounds containing a polyene structure, and power levels are in the range of 50–1000 W/cm$^2$ or even higher.

Konig et al., DD 259351, teaches a process for thermal treatment of tumor tissue that comprises depositing a medium in the tumor tissue that absorbs radiation in the red and/or near red infrared spectral region, and irradiating the infiltrated tissue with an appropriate wavelength of laser light. Absorbing media can include methylene blue, reduced porphyrin or its aggregates, and phthalocyanine blue. Methylene blue, which strongly absorbs at 600–700 nm, and a krypton laser emitting at 647 and 676 nm are exemplified. The power level should be at least 200 mW/cm$^2$.

It has been shown that by stripping the stratum corneum from a small area of the skin with repeated application and removal of cellophane tape to the same location one can easily collect arbitrary quantities of interstitial fluid, which can then be assayed for a number of analytes of interest. Similarly, the 'tape-stripped' skin has also been shown to be permeable to the transdermal delivery of compounds into the body. Unfortunately, 'tape-stripping' leaves a open sore which takes weeks to heal, and for this, as well as other reasons, is not considered as an acceptable practice for enhancing transcutaneous transport in wide applications.

As discussed above, it has been shown that pulsed lasers, such as the excimer laser operating at 193 nm, the erbium laser operating near 2.9 $\mu$m or the $CO_2$ laser operating at 10.2 $\mu$m, can be used to effectively ablate small holes in the human stratum corneum. These laser ablation techniques offer the potential for a selective and potentially non-traumatic method for opening a delivery and/or sampling hole through the stratum corneum. However, due to the prohibitively high costs associated with these light sources, there have been no commercial products developed based on this concept. The presently disclosed invention, by defining a method for directly conducting thermal energy into the stratum corneum with very tightly defined spatial and temporal resolution, makes it possible to produce the desired micro-ablation of the stratum corneum using very low cost energy sources.

In view of the foregoing problems and/or deficiencies, the development of a method for safely enhancing the permeability of the skin for minimally invasive or noninvasive monitoring of body analytes in a more rapid time frame would be a significant advancement in the art. It would be another significant advancement in the art to provide a method of minimally invasively or non-invasively enhancing the transdermal flux rate of a drug into a selected area of an individual's body.

BRIEF SUMMARY OF THE INVENTION

An object of the invention is to minimize the barrier properties of the stratum corneum using poration to controllably collect analytes from within the body through perforations in the stratum corneum to enable the monitoring of these analytes.

It is also an object of the invention to provide a method of monitoring selected analytes in the body through micropores in the stratum corneum in combination with sonic energy, permeation enhancers, pressure gradients, and the like.

Another object of the invention is to provide a method for controlling transdermal flux rates of drugs or other molecules into the body and, if desired, into the bloodstream through minute perforations in the stratum corneum.

It is still another object of the invention to provide a method of delivering drugs into the body through micropores in the stratum corneum in combination with sonic energy, permeation enhancers, pressure gradients, and the like.

These and other objects may be accomplished by providing a method for monitoring the concentration of an analyte in an individual's body comprising the steps of enhancing the permeability of the stratum corneum of a selected area of the individual's body surface to the analyte by means of (a) porating the stratum corneum of the selected area by means that form a micro-pore in the stratum corneum without causing serious damage to the underlying tissues, thereby reducing the barrier properties of the stratum corneum to the withdrawal of the analyte;

(b) collecting a selected amount of the analyte; and (c) quantitating the analyte collected.

In one preferred embodiment, the method further comprises applying sonic energy to the porated selected area at a frequency in the range of about 5 kHz to 100 MHz, wherein the sonic energy is modulated by means of a member selected from the group consisting of frequency modulation, amplitude modulation, phase modulation, and combinations thereof. In another preferred embodiment, the method further comprises contacting the selected area of the individual's body with a chemical enhancer with the application of the sonic energy to further enhance analyte withdrawal.

Porating of the stratum corneum is accomplished by means selected from the group consisting of (a) ablating the stratum corneum by contacting a selected area, up to about 1000 μm across, of the stratum corneum with a heat source such that the temperatureu of tissue-bound water and other vaporizable substances in the selected area is elevated above the vaporization point of the water and other vaporizable substances thereby removing the stratum corneum in the selected area; (b) puncturing the stratum corneum with a micro-lancet calibrated to form a micropore of up to about 1000 μm in diameter; (d) ablating the stratum corneum by focusing a tightly focused beam of sonic energy onto the stratum corneum; (d) hydraulically puncturing the stratum corneum with a high pressure jet of fluid to form a micropore of up to about 1000 μm in diameter and (e) puncturing the stratum corneum with short pulses of electricity to form a micropore of up to about 1000 μm in diameter.

One preferred embodiment of thermally ablating the stratum corneum comprises treating at least the selected area with an effective amount of a dye that exhibits strong absorption over the emission range of a pulsed light source and focusing the output of a series of pulses from the pulsed light source onto the dye such that the dye is heated sufficiently to conductively transfer heat to the stratum corneum to elevate the temperature of tissue-bound water and other vaporizable substances in the selected area above the vaporization point of the water and other vaporizable substances. Preferably, the pulsed light source emits at a wavelength that is not significantly absorbed by skin. For example, the pulsed light source can be a laser diode emitting in the range of about 630 to 1550 nm, a laser diode pumped optical parametric oscillator emitting in the range of about 700 and 3000 nm, or a member selected from the group consisting of arc lamps, incandescent lamps, and light emitting diodes. A sensing system for determining when the barrier properties of the stratum corneum have been sur-mounted can also be provided. One preferred sensing system comprises light collection means for receiving light reflected from the selected area and focusing the reflected light on a photodiode, a photodiode for receiving the focused light and sending a signal to a controller wherein the signal indicates a quality of the reflected light, and a controller coupled to the photodiode and to the pulsed light source for receiving the signal and for shutting off the pulsed light source when a preselected signal is received.

In another preferred embodiment, the method further comprises cooling the selected area of stratum corneum and adjacent skin tissues with cooling means such that said selected area and adjacent skin tissues are in a selected precooled, steady state, condition prior to poration.

In still another preferred embodiment, the method comprises ablating the stratum corneum such that interstitial fluid exudes from the micropores, collecting the interstitial fluid, and analyzing the analyte in the collected interstitial fluid. After the interstitial fluid is collected, the micropore can be sealed by applying an effective amount of energy from the laser diode or other light source such that interstitial fluid remaining in the micropore is caused to coagulate. Preferably, vacuum is applied to the porated selected area to enhance collection of interstitial fluid.

In yet another preferred embodiment, the method comprises, prior to porating the stratum corneum, illuminating at least the selected area with unfocused light from the pulsed light source such that the selected area illuminated with the light is sterilized.

Another preferred method of porating the stratum corneum comprises contacting the selected area with a metallic wire such that the temperature of the selected area is raised from ambient skin temperature to greater than 100° C. within about 10 to 50 ms and then returning the temperature of the selected area to approximately ambient skin temperature within about 30 to 50 ms, wherein this cycle of raising the temperature and returning to approximately ambient skin temperature is repeated a number of time effective for reducing the barrier properties of the stratum corneum. Preferably, the step of returning to approximately ambient skin temperature is carried out by withdrawing the wire from contact with the stratum corneum. It is also preferred to provide means for monitoring electrical impedance between the wire and the individual's body through the selected area of stratum corneum and adjacent skin tissues and means for advancing the position of the wire such that as the ablation occurs with a concomitant reduction in resistance, the advancing means advances the wire such that the wire is in contact with the stratum corneum during heating of the wire. Further, it is also preferred to provide means for withdrawing the wire from contact with the stratum corneum, wherein the monitoring means is capable of detecting a change in impedance associated with contacting an epidermal layer underlying the stratum corneum and sending a signal to the withdrawing means to withdrawn the wire from contact with the stratum corneum. The wire can be heated by an ohmic heating element, can have a current loop having a high resistance point wherein the temperature of the high resistance point is modulated by passing a modulated electrical current through said current loop to effect the heating, or can be positioned in a modulatable alternating magnetic field of an excitation coil such that energizing the excitation coil with alternating current produces eddy currents suffient to heat the wire by internal ohmic losses.

A method for enhancing the transdermal flux rate of an active permeant into a selected area of an individual's body comprising the steps of enhancing the permeability of the stratum corneum layer of the selected area of the individual's body surface to the active permeant by means of (a) porating the stratum corneum of the selected area by means that form a micro-pore in the stratum corneum without causing serious damage to the underlying tissues and thereby reduce the barrier properties of the stratum corneum to the flux of the active permeant; and (b) contacting the porated selected area with a composition comprising an effective amount of the permeant such that the flux of the permeant into the body is enhanced.

In a preferred embodiment, the method further comprises applying sonic energy to the porated selected area for a time and at an intensity and a frequency effective to create a fluid streaming effect and thereby enhance the transdermal flux rate of the permeant into the body.

A method is also provided for applying a tatoo to a selected area of skin on an individual's body surface comprising the steps of:

(a) porating the stratum corneum of the selected area by means that form a micro-pore in the stratum corneum without causing serious damage to the underlying tissues and thereby reduce the barrier properties of the stratum corneum to the flux of a permeant; and (b) contacting the porated selected area with a composition comprising an effective amount of a tattooing ink as a permeant such that the flux of said ink into the body is enhanced.

A method is still further provided for reducing a temporal delay in diffusion of an analyte from blood of an individual to said individual's interstitial fluid in a selected area of skin comprising applying means for cooling to said selected area of skin.

A method is yet further provided for reducing evaporation of interstitial fluid and the vapor pressure thereof, wherein said interstitial fluid is being collected from a micropore in a selected area of stratum corneum of an individual's skin, comprising applying means for cooling to said selected area of skin.

BRIEF DESCRIPTION OF THE SEVERAL VIEWS OF THE DRAWINGS

FIG. 3A shows a schematic representation of an optical poration system comprising a cooling device.

FIG. 3B shows a top view of a schematic representation of an illustrative cooling device according to FIG. 3A.

FIGS. 9–11 show graphic representations of temperature distribution during simulated thermal poration events using optical poration.

FIGS. 31, 32, and 33 show a perspective view of an ultrasonic transducer/vacuum apparatus for harvesting interstitial fluid, a cross section view of the same apparatus, and cross sectional schematic view of the same apparatus, respectively.

FIGS. 34A–B show a top view of a handheld ultrasonic transducer and a side view of the spatulate end thereof, respectively.

DETAILED DESCRIPTION

Figure 1:
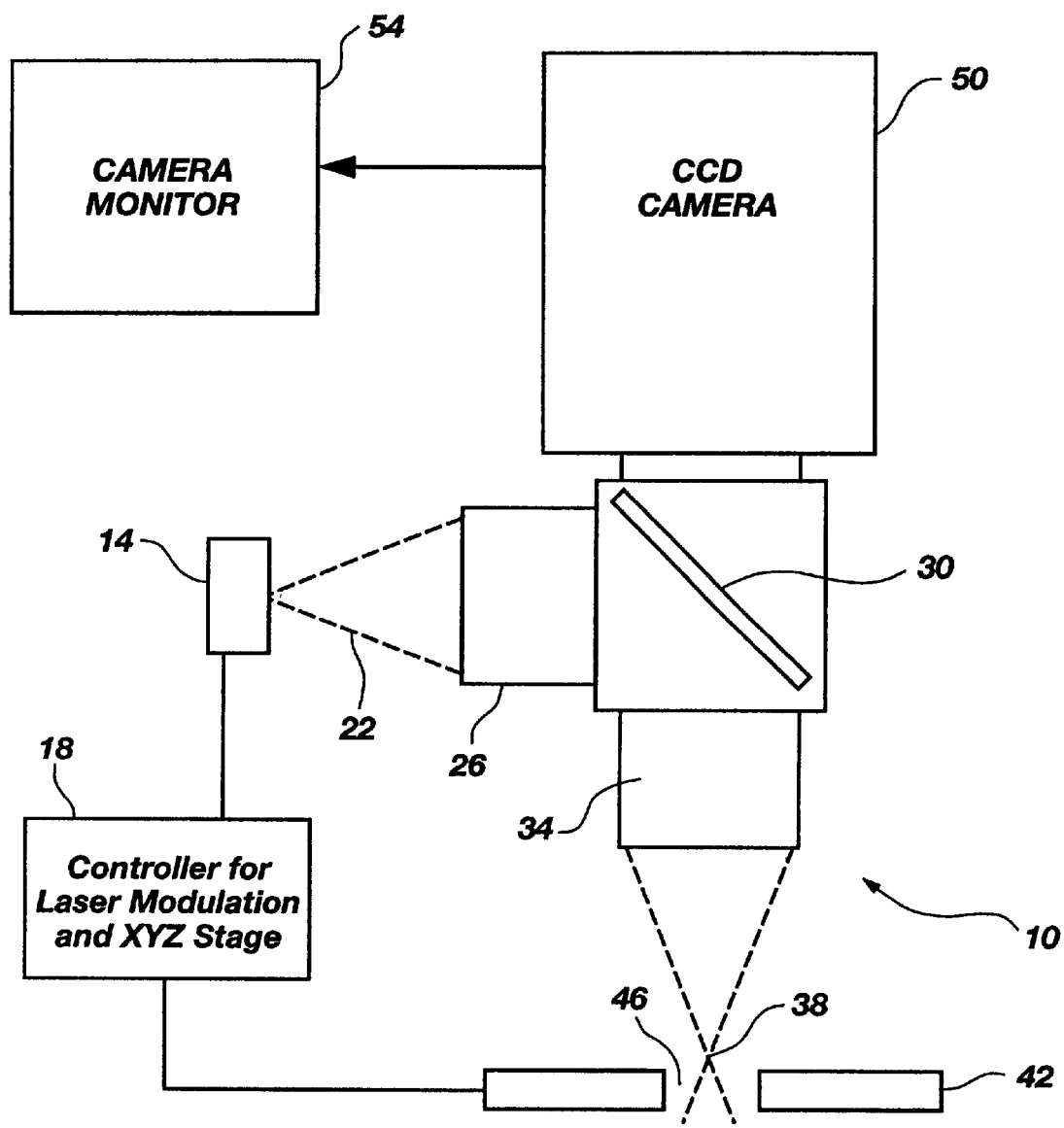
FIG. 1 shows a schematic representation of a system for delivering laser diode light and monitoring the progress of poration.

Before the present methods for permeabilizing the stratum corneum for facilitating transdermal drug delivery and analyte sampling are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the"

include plural referents unless the context clearly dictates otherwise. Thus, for example, reference to a method for delivery of "a drug" includes reference to delivery of a mixture of two or more drugs, reference to "an analyte" includes reference to one or more of such analytes, and reference to "a permeation enhancer" includes reference to a mixture of two or more permeation enhancers.

In describing and claiming the present invention, the following terminology will be used in accordance with the definitions set out below.

As used herein, "poration," "microporation," or any such similar term means the formation of a small hole or pore in the stratum corneum in a selected area of the skin of an individual to lessen the barrier properties of this layer of the skin to the passage of analytes from below the skin surface for analysis or the passage of active permeants or drugs into the body for therapeutic purposes. Preferably the hole or pore will be no larger than about 1 mm in diameter, and more preferably no larger than about 100 $\mu$m in diameter, and will extend into the stratum corneum sufficiently to break the barrier properties of this layer without adversely affecting the underlying tissues.

As used herein "ablation" means the controlled removal of cells caused by kinetic energy released when the vaporizable components of the cells have been heated to the point that vaporization occurs and the resulting rapid expansion of volume due to this phase change causes cells and possibly some adjacent cells to be "blown away" from the abaltion site.

As used herein "puncture" or "micro-puncture" means the use of mechanical, hydraulic, or electrical means to perforate the stratum corneum.

To the extent that "ablation" and "puncture" accomplish the same purpose of poration, i.e. the creating a hole or pore in the stratum corneum without significant damage to the underlying tissues, these terms may be used interchangeably.

As used herein, "penetration enhancement" or "permeation enhancement" means an increase in the permeability of skin to a drug, analyte, dye, stain, or other chemical molecule (also called "permeant"), i.e., so as to increase the rate at which a drug, analyte, or chemical molecule permeates the stratum corneum and facilitates the poration of the stratum corneum, the withdrawal of analytes out through the stratum corneum or the delivery of drugs through the stratum corneum and into the underlying tissues. The enhanced permeation effected through the use of such enhancers can be observed, for example, by observing diffusion of a dye, as a permeant, through animal or human skin using a diffusion apparatus.

As used herein, "chemical enhancer," "penetration enhancer," "permeation enhancer," and the like includes all enhancers that increase the flux of a permeant, analyte, or other molecule across the skin, and is limited only by functionality. In other words, all cell envelope disordering compounds and solvents and any other chemical enhancement agents are intended to be included.

As used herein, "dye," "stain," and the like shall be used interchangeably and refer to a biologically suitable chromophore that exhibits strong absorption at the emission range of a pulsed light source used to ablate tissues of the stratum corneum to form micropores therein.

As used herein, "transdermal" or "percutaneous" means passage of a permeant into and through the skin to achieve effective therapeutic blood levels or deep tissue levels of a drug, or the passage of a molecule present in the body ("analyte") out through the skin so that the analyte molecule may be collected on the outside of the body.

As used herein, the term "permeant," "drug," or "pharmacologically active agent" or any other similar term means any chemical or biological material or compound suitable for transdermal administration by the methods previously known in the art and/or by the methods taught in the present invention, that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anaesthetic effect, or it may be systemic. This invention is not drawn to novel permeants or to new classes of active agents. Rather it is limited to the mode of delivery of agents or permeants that exist in the state of the art or that may later be established as active agents and that are suitable for delivery by the present invention. Such substances include broad classes of compounds normally delivered into the body, including through body surfaces and membranes, including skin. In general, this includes but is not limited to: antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; and tranquilizers. By the method of the present invention, both ionized and nonionized drugs may be delivered, as can drugs of either high or low molecular weight.

As used herein, an "effective" amount of a pharmacologically active agent means a sufficient amount of a compound to provide the desired local or systemic effect and performance at a reasonable benefit/risk ratio attending any medical treatment. An "effective" amount of a permeation or chemical enhancer as used herein means an amount selected so as to provide the desired increase in skin permeability and the desired depth of penetration, rate of administration, and amount of drug delivered.

As used herein, "carriers" or "vehicles" refer to carrier materials without significant pharmacological activity at the quantities used that are suitable for administration with other pharmaceutically active materials, and include any such materials known in the art, e.g., any liquid, gel, solvent, liquid diluent, solubilizer, or the like, that is nontoxic at the quantities employed and does not interact with the drug to be administered in a deleterious manner. Examples of suitable carriers for use herein include water, mineral oil, silicone, inorganic gels, aqueous emulsions, liquid sugars, waxes, petroleum jelly, and a variety of other oils and polymeric materials.

As used herein, a "biological membrane" is intended to mean a membrane material present within a living organism that separates one area of the organism from another and, in many instances, that separates the organism from its outer environment. Skin and mucous membranes are thus included.

As used herein, "individual" refers to both a human and an animal, to which the present invention may be applied.

As used herein, "analyte" means any chemical or biological material or compound suitable for passage through a biological membrane by the technology taught in this present invention, or by technology previously known in the art, of which an individual might want to know the concentration or activity inside the body. Glucose is a specific example of an analyte because it is a sugar suitable for passage through the skin, and individuals, for example those having diabetes, might want to know their blood glucose levels. Other examples of analytes include, but are not limited to, such compounds as sodium, potassium, bilirubin, urea, ammonia, calcium, lead, iron, lithium, salicylates, and the like.

As used herein, "transdermal flux rate" is the rate of passage of any analyte out through the skin of an individual, human or animal, or the rate of passage of any drug, pharmacologically active agent, dye, or pigment in and through the skin of an individual, human or animal.

As used herein, the terms "intensity amplitude," "intensity," and "amplitude" are used synonymously and refer to the amount of energy being produced by the sonic energy system.

As used herein, "frequency modulation" or "sweep" means a continuous, graded or stepped variation in the amplitude or frequency of ultrasound in a given time period. A frequency modulation is a graded or stepped variation in frequency in a given time period, for example 5.4–5.76 MHz in 1 sec., or 5–10 MHz in 0.1 sec., or 10–5 MHz in 0.1 sec., or any other frequency range or time period that is appropriate to a specific application. A complex modulation can include varying both the frequency and intensity simultaneously. For example, FIGS. 4A and 4B of U.S. Pat. No. 5,458,140 could, respectively, represent amplitude and frequency modulations being applied simultaneously to a single sonic energy transducer.

As used herein "phase modulation" means the timing of the signal has been changed relative to its initial state shown in FIG. 4C of U.S. Pat. No. 5,458,140. The frequency and amplitude of the signal can remain the same. A phase modulation can be implemented with a variable delay such as to selectively retard or advance the signal temporarily in reference to its previous state, or to another signal.

The sonic energy, in its various applications such as with frequency, intensity or phase modulation, or combinations thereof and the use of chemical enhancers combined with modulated sonic energy, as described herein, can vary over a frequency range of between about 5 kHz to 100 MHz, with a range of between about 20 kHz and 30 MHz being preferred.

As used herein, "non-invasive" means not requiring the entry of a needle, catheter, or other invasive medical instrument into a part of the body.

As user herein, "minimally invasive" refers to the use of mechanical, hydraulic, or electrical means that invade the stratum corneum to create a small hole or micropore without causing substantial damage to the underlying tissues.

Means for Poration of the Stratum Corneum

The formation of a micropore in the stratum corneum can be accomplished by various state of the art means as well as certain means disclosed herein that are improvements thereof.

The use of laser ablation as described by Jacques et al. in U.S. Pat. No. 4,775,361 and by Lane et al., supra, certainly provide one means for ablating the stratum corneum using an excimer laser. At 193 nm wavelength, and 14 ns pulsewidth, it was found that about 0.24 to 2.8 $\mu$m of stratum corneum could be removed by each laser pulse at radiant exposure of between about 70 and 480 mJ/cm$^2$. As the pulse energy increases, more tissue is removed from the stratum corneum and fewer pulses are required for complete poration of this layer. The lower threshold of radiant exposure that must be absorbed by the stratum corneum within the limit of the thermal relaxation time to cause suitable micro-explosions that result in tissue ablation is about 70 mJ/cm$^2$ within a 50 millisecond (ms) time. In other words, a total of 70 mJ/cm$^2$ must be delivered within a 50 ms window. This can be done in a single pulse of 70 mJ/cm$^2$ or in 10 pulses of 7 mJ/cm$^2$, or with a continuous illumination of 1.4 watts/cm$^2$ during the 50 ms time. The upper limit of radiant exposure is that which will ablate the stratum corneum without damage to underlying tissue and can be empirically determined from the light source, wavelength of light, and other variables that are within the experience and knowledge of one skilled in this art.

By "deliver" is meant that the stated amount of energy is absorbed by the tissue to be ablated. At the excimer laser wavelength of 193 nm, essentially 100% absorption occurs within the first 1 or 2 $\mu$m of stratum corneum tissue. Assuming the stratum corneum is about 20 $\mu$m thick, at longer wavelengths, such as 670 nm, only about 5% of incident light is absorbed within the 20 $\mu$m layer. This means that about 95% of the high power beam passes into the tissues underlying the stratum corneum where it will likely cause significant damage.

The ideal is to use only as much power as is necessary to perforate the stratum corneum without causing bleeding, thermal, or other damage to underlying tissues from which analytes are to be extracted or drugs or other permeants delivered.

It would be beneficial to use sources of energy more economical than energy from excimer lasers. Excimer lasers, which emit light at wavelengths in the far UV region, are much more expensive to operate and maintain than, for example, diode lasers that emit light at wavelengths in visible and IR regions (600 to 1800 nm). However, at the longer wavelengths, the stratum corneum becomes increasingly more transparent and absorption occurs primarily in the underlying tissues.

The present invention facilitates a rapid and painless method of eliminating the barrier function of the stratum corneum to facilitate the transcutaneous transport of therapeutic substances into the body when applied topically or to access the analytes within the body for analysis. The method utilizes a procedure which begins with the contact application of a small area heat source to the targeted area of the stratum corneum.

The heat source must have several important properties, as will now be described. First, the heat source must be sized such that contact with the skin is confined to a small area, typically about 1 to 1000 $\mu$m in diameter. Second, it must have the capability to modulate the temperature of the stratum corneum at the contact point from ambient skin surface temperature levels (33° C.) to greater than 123° C. and then return to approximately ambient skin temperature with cycle times to minimize collateral damage to viable tissues and sensation to the subject individual. This modulation can be created electronically, mechanically, or chemically.

Additionally, an inherent depth limiting feature of the microporation process can be facilitated if the heat source has both a small enough thermal mass and limited energy source to elevate its temperature such that when it is placed in contact with tissues with more than 30% water content, the thermal dispersion in these tissues is sufficient to limit the maximum temperature of the heat source to less than 100° C. This feature effectively stops the thermal vaporization process once the heat probe had penetrated through the stratum corneum into the lower layers of the epidermis.

With the heat source placed in contact with the skin, it is cycled through a series of one or more modulations of temperature from an initial point of ambient skin temperature to a peak temperature in excess of 123° C. to approximately ambient skin temperature. To minimize or eliminate the subject's sensory perception of the microporation process, these pulses are limited in duration, and the inter-pulse spacing is long enough to allow cooling of the viable tissue layers in the skin, and most particularly the enervated dermal tissues, to achieve a mean temperature of less than about 45° C. These parameters are based on the thermal time constants of the viable epidermal tissues (roughly 30–80 ms) located between the heat probe and the enervated tissue in the underlying dermis. The result of this application of pulsed thermal energy is that enough energy is conducted into the stratum corneum within the tiny target spot that the local temperature of this volume of tissue is elevated sufficiently higher than the vaporization point of the tissue-bound water content in the stratum corneum. As the temperature increases above 100° C., the water content of the stratum corneum (typically 5% to 15%) within this localized spot, is induced to vaporize and expand very rapidly, causing a vapor-driven removal of those corneocytes in the stratum corneum located in proximity to this vaporization event. U.S. Pat. No. 4,775,361 teaches that a stratum corneum temperature of 123° C. represents a threshold at which this type of flash vaporization occurs. As subsequent pulses of thermal energy are applied, additional layers of the stratum corneum are removed until a micropore is formed through the stratum corneum down to the next layer of the epidermis, the stratum lucidum. By limiting the duration of the heat pulse to less than one thermal time constant of the epidermis and allowing any heat energy conducted into the epidermis to dissipate for a sufficiently long enough time, the elevation in temperature of the viable layers of the epidermis is minimal. This allows the entire microporation process to take place without any sensation to the subject and no damage to the underlying and surrounding tissues.

The present invention comprises a method for painlessly creating microscopic holes, i.e. micropores, from about 1 to 1000 $\mu$m across, in the stratum corneum of human skin. The key to successfully implementing this method is the creation of an appropriate thermal energy source, or heat probe, which is held in contact with the stratum corneum. The principle technical challenge in fabricating an appropriate heat probe is designing a device that has the desired contact with the skin and that can be thermally modulated at a sufficiently high frequency.

It is possible to fabricate an appropriate heat probe by topically applying to the stratum corneum a suitable light-absorbing compound, such as a dye or stain, selected because of its ability to absorb light at the wavelength emitted by a selected light source. In this instance, the selected light source may be a laser diode emitting at a wavelength which would not normally be absorbed by the skin tissues. By focusing the light source to a small spot on the surface of the topical layer of the dye, the targeted area can be temperature modulated by varying the intensity of the light flux focused on it. It is possible to utilize the energy from laser sources emitting at a longer wavelength than an excimer laser by first topically applying to the stratum corneum a suitable light-absorbing compound, such as a dye or stain, selected because of its ability to absorb light at the wavelength emitted by the laser source. The same concept can be applied at any wavelength and one must only choose an appropriate dye or stain and optical wavelength. One need only look to any reference manual to find which suitable dyes and wavelength of the maximum absorbance of that dye. One such reference is Green, *The Sigma-Aldrich Handbook of Stains, Dyes and Indicators*, Aldrich Chemical Company, Inc. Milwaukee, Wis. (1991). For example, copper phthalocyanine (Pigment Blue 15; CPC) absorbs at about 800 nm; copper phthalocyanine tetrasulfonic acid (Acid Blue 249) absorbs at about 610 nm; and Indocyanine Green absorbs at about 775 nm; and Cryptocyanine absorbs at about 703 nm. CPC is particularly well suited for this embodiment for the following reasons: it is a very stable and inert compound, already approved by the FDA for use as a dye in implantable sutures; it absorbs very strongly at wavelengths from 750 nm to 950 nm, which coincide well with numerous low cost, solid state emitters such as laser diodes and LEDs, and in addition, this area of optical bandwidth is similarly not absorbed directly by the skin tissues in any significant amount; CPC has a very high vaporization point (>550 C. in a vacuum) and goes directly from a solid phase to a vapor phase with no liquid phase; CPC has a relatively low thermal diffusivity constant, allowing the light energy focused on it to selectively heat only that area directly in the focal point with very little lateral spreading of the 'hot-spot' into the surrounding CPC thereby assisting in the spatial definition of the contact heat-probe.

The purpose of this disclosure is not to make an exhaustive listing of suitable dyes or stains because such may be easily ascertained by one skilled in the art from data readily available.

The same is true for any desired particular pulsed light source. For example, this method may be implemented with a mechanically shuttered, focused incandescent lamp as the pulse light source. Various catalogs and sales literature show numerous lasers operating in the near UV, visible and near IR range. Representative lasers are Hammamatsu Photonic Systems Model PLP-02 which operates at a power output of $2 \times 10^{-8}$ J, at a wavelength of 415 nm; Hammamatsu Photonic Systems Model PLP-05 which operates at a power output of 15 J, at a wavelength of 685 nm; SDL, Inc., SDL-3250 Series pulsed laser which operates at a power output of $2 \times 10^6$ J at a wavelength of about 800–810 nm; SDL, Inc., Model SDL-8630 which operates at a power output of 500 mW at a wavelength of about 670 nm; Uniphase Laser Model AR-081-15000 which operates at a power output of 15,000 mW at a wavelength of 790–830 nm; Toshiba America Electronic Model TOLD9150 which operates at a power output of 30 mW at a wavelength of 690 nm; and LiCONIX, Model Diolite 800-50 which operates at a power 50 mW at a wavelength of 780 nm.

For purposes of the present invention a pulsed laser light source can emit radiation over a wide range of wavelengths ranging from between about 100 nm to 12,000 nm. Excimer lasers typically will emit over a range of between about 100 to 400 nm. Commercial excimer lasers are currently available with wavelengths in the range of about 193 nm to 350 nm.

Preferably a laser diode will have an emission range of between about 380 to 1550 nm. A frequency doubled laser diode will have an emission range of between about 190 and 775 nm. Longer wavelengths ranging from between about 1300 and 3000 nm may be utilized using a laser diode pumped optical parametric oscillator. It is expected, given the amount of research taking place on laser technology, that these ranges will expand with time.

Delivered or absorbed energy need not be obtained from a laser as any source of light, whether it is from a laser, a short arc lamp such as a xenon flashlamp, an incandescent lamp, a light-emitting diode (LED), the sun, or any other source may be used. Thus, the particular instrument used for delivering electromagnetic radiation is less important than the wavelength and energy associated therewith. Any suitable instrument capable of delivering the necessary energy at suitable wavelengths, ie. in the range of about 100 nm to about 12,000 nm, can be considered within the scope of the invention. The essential feature is that the energy must be absorbed by the light-absorbing compound to cause localized heating thereof, followed by conduction of sufficient heat to the tissue to be ablated within the timeframe allowed.

In one illustrative embodiment, the heat probe itself is formed from a thin layer, preferably about 5 to 1000 $\mu$m thick, of a solid, non-biologically active compound, applied topically to a selected area of an individual's skin that is large enough to cover the site where a micropore is to be created. The specific formulation of the chemical compound is chosen such that it exhibits high absorption over the spectral range of a light source selected for providing energy to the light-absorbing compound. The probe can be, for example, a sheet of a solid compound, a film treated with a high melting point absorbing compound, or a direct application of the light-absorbing compound to the skin as a precipitate or as a suspension in a carrier. Regardless of the configuration of the light-absorbing heat probe, it must exhibit a low enough lateral thermal diffusion coefficient such that any local elevations of temperature will remain spatially defined and the dominant mode of heat loss will be via direct conduction into the stratum corneum through the point of contact between the skin and the probe.

The required temperature modulation of the probe can be achieved by focusing a light source onto the light-absorbing compound and modulating the intensity of this light source. If the energy absorbed within the illuminated area is sufficiently high, it will cause the light absorbing compound to rapidly heat up. The amount of energy delivered, and subsequently both the rate of heating and peak temperature of the light-absorbing compound at the focal point, can be easily modulated by varying the pulse width and peak power of the light source. In this embodiment, it is only the small volume of light-absorbing compound heated up by the focused, incident optical energy that forms the heat probe, additional light absorbing compound which may have been applied over a larger area then the actual poration site is incidental. By using a solid phase light-absorbing compound with a relatively high melting point, such as copper phthalocyanine (CPC), which remains in its solid phase up to a temperature of greater than 550° C., the heat probe can be quickly brought up to a temperature of several hundred degrees C., and still remain in contact with the skin, allowing this thermal energy to be conducted into the stratum corneum. In addition, this embodiment comprises choosing a light source with an emission spectrum where very little energy would normally be absorbed in the skin tissues.

Once the targeted area has the light-absorbing compound topically positioned on it, the heat probe is formed when the light source is activated with the focal waist of the beam positioned to be coincident with the surface of the treated area. The energy density of light at the focal waist and the amount of absorption taking place within the light-absorbing compound are set to be sufficient to bring the temperature of the light-absorbing compound, within the area of the small spot defined by the focus of the light source, to greater than 123° C. within a few milliseconds. As the temperature of the heat probe rises, conduction into the stratum corneum delivers energy into these tissues, elevating the local temperature of the stratum corneum. When enough energy has been delivered into this small area of stratum corneum to cause the local temperature to be elevated above the boiling point of the water contained in these tissues, a flash vaporization of this water takes place, ablating the stratum corneum at this point.

By turning the light source on and off, the temperature of the heat probe can be rapidly modulated and the selective ablation of these tissues can be achieved, allowing a very precisely dimensioned hole to be created, which selectively penetrates only through the first 10 to 30 $\mu$m of skin.

An additional feature of this embodiment is that by choosing a light source that would normally have very little energy absorbed by the skin or underlying tissues, and by designing the focusing and delivery optics to have a sufficiently high numerical aperture, the small amount of delivered light that does not happen to get absorbed in the heat probe itself, quickly diverges as it penetrates deep into the body. Since there is very little absorption at the delivered wavelengths, essentially no energy is delivered to the skin directly from the light source. This three dimensional dilution of coupled energy in the tissues due to beam divergence and the low level of absorption in the untreated tissue results in a completely benign interaction between the light beam and the tissues, with no damage being done thereby.

In one preferred embodiment of the invention, a laser diode is used as the light source with an emission wavelength of 800±30 nm. A heat-probe can be formed by topical application of a transparent adhesive tape that has been treated on the adhesive side with a 0.5 cm spot formed from a deposit of finely ground copper phthalocyanine (CPC). The CPC exhibits extremely high absorption coefficients in the 800 nm spectral range, typically absorbing more than 95% of the radiant energy from a laser diode.

FIG. 1 shows a system 10 for delivering light from such a laser diode to a selected area of an individual's skin and for monitoring the progress of the poration process. The system comprises a laser diode 14 coupled to a controller 18, which controls the intensity, duration, and spacing of the light pulses. The laser diode emits a beam 22 that is directed to a collection lens or lenses 26, which focuses the beam onto a mirror 30. The beam is then reflected by the mirror to an objective lens or lenses 34, which focuses the beam at a preselected point 38. This preselected point corresponds with the plane of an xyz stage 42 and the objective hole 46 thereof, such that a selected area of an individual's skin can be irradiated. The xyz stage is connected to the controller such that the position of the xyz stage can be controlled. The system also comprises a monitoring system comprising a CCD camera 50 coupled to a monitor 54 The CCD camera is confocally aligned with the objective lens such that the progress of the poration process can be monitored visually on the monitor.

Figure 2:
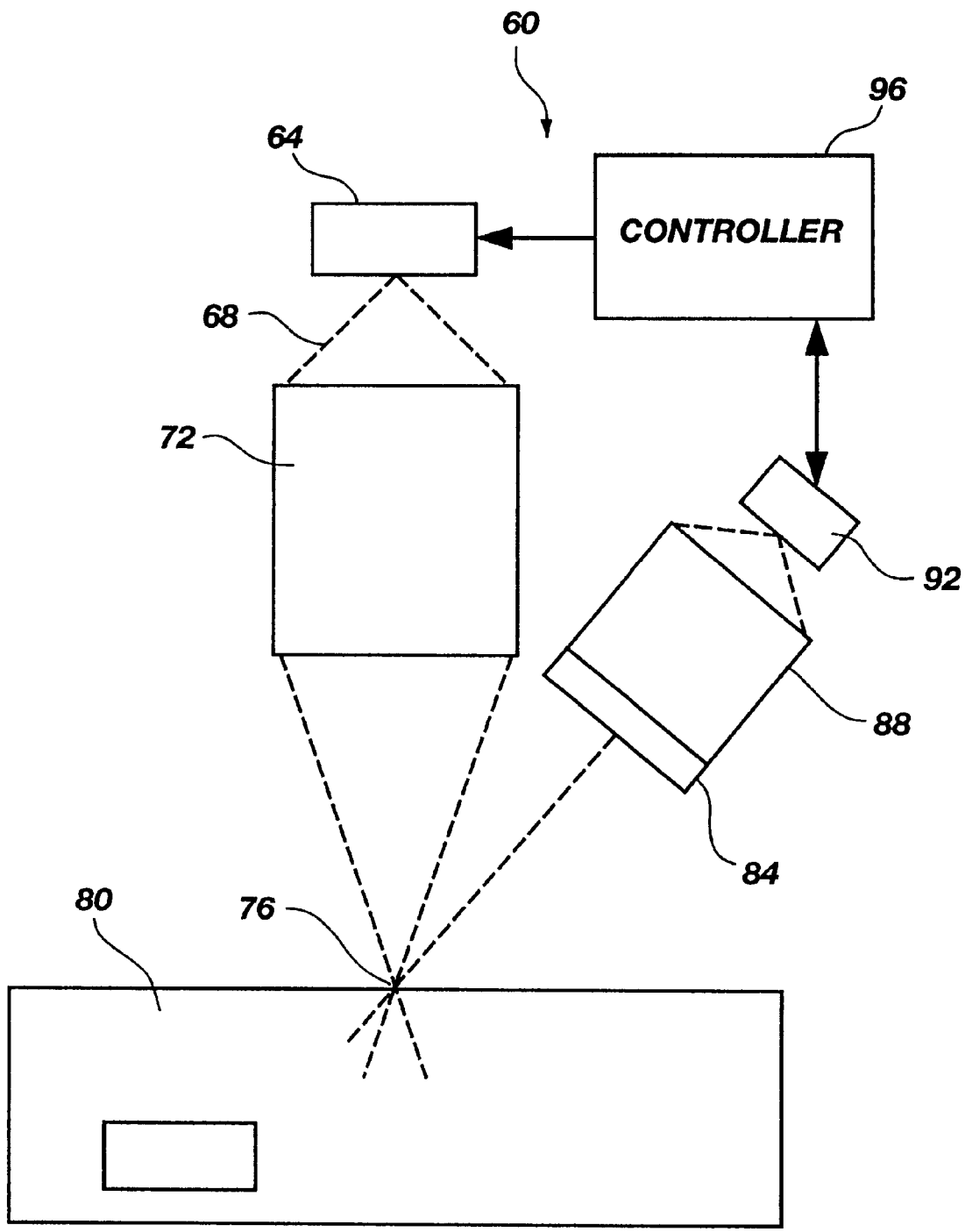
FIG. 2 shows a schematic representation of a closed-loop feedback system for monitoring poration.

In another illustrative embodiment of the invention, a system of sensing photodiodes and collection optics that have been confocally aligned with the ablation light source is provided. FIG. 2 shows a sensor system 60 for use in this embodiment. The system comprises a light source 64 for emitting a beam of light 68, which is directed through a delivery optics system 72 that focuses the beam at a preselected point 76, such as the surface of an individual's skin 80. A portion of the light contacting the skin is reflected, and other light is emitted from the irradiated area. A portion of this reflected and emitted light passes through a filter 84 and then through a collection optics system 88, which focuses the light on a phototodiode 92. A controller 96 is coupled to both the laser diode and the photodiode for, respectively, controlling the output of the laser diode and detecting the light that reaches the photodiode. Only selected portions of the spectrum emitted from the skin pass through the filter. By analyzing the shifts in the reflected and emitted light from the targeted area, the system has the ability to detect when the stratum corneum has been breached, and this feedback is then used to control the light source, deactivating the pulses of light when the microporation of the stratum corneum is achieved. By employing this type of active closed loop feedback system, a self regulating, universally applicable device is obtained that produces uniformly dimensioned micropores in the stratum corneum, with minimal power requirements, regardless of variations from one individual to the next.

In another illustrative embodiment, a cooling device is incorporated into the system interface to the skin. FIG. 3A shows an illustrative schematic representation thereof. In this system 100, a light source 104 (coupled to a controller 106) emits a beam of light 108, which passes through and is focused by a delivery optics system 112. The beam is focused by the delivery optics system to a preselected point 116, such as a selected area of an individual's skin 120. A cooling device 124, such as a Peltier device or other means of chilling, contacts the skin to cool the surface thereof. In a preferred embodiment of the cooling device 124 (FIG. 3B), there is a central hole 128 through which the beam of focused light passes to contact the skin. Referring again to FIG. 3A, a heat sink 132 is also preferably placed in contact with the cooling device. By providing a cooling device with a small hole in its center coincident with the focus of the light, the skin tissues in the general area where the poration is to be created may be pre-cooled to 5° C. to 10° C. This pre-cooling allows a greater safety margin for the system to operate in that the potential sensations to the user and the possibility of any collateral damage to the epidermis directly below the poration site are reduced significantly from non-cooled embodiment. Moreover, for monitoring applications, pre-cooling minimizes evaporation of interstitial fluid and can also provide advantageous physical properties, such as decreased surface tension of such interstitial fluid. Still further, cooling the tissue is known to cause a localized increase in blood flow in such cooled tissue, thus promoting diffusion of analytes from the blood into the interstitial fluid.

The method can also be applied for other micro-surgery techniques wherein the light-absorbing compound/heat-probe is applied to the area to be ablated and then the light source is used to selectively modulate the temperature of the probe at the selected target site, affecting the tissues via the vaporization-ablation process produced.

A further feature of the invention is to use the light source to help seal the micropore after its usefulness has passed. Specifically, in the case of monitoring for an internal analyte, a micropore is created and some amount of interstitial fluid is extracted through this opening. After a sufficient amount of interstitial fluid had been collected, the light source is reactivated at a reduced power level to facilitate rapid clotting or coagulation of the interstitial fluid within the micropore. By forcing the coagulation or clotting of the fluid in the pore, this opening in the body is effectively sealed, thus reducing the risk of infection. Also, the use of the light source itself for both the formation of the micropore and the sealing thereof is an inherently sterile procedure, with no physical penetration into the body by any device or apparatus. Further, the thermal shock induced by the light energy kills any microbes that may happen to be present at the ablation site.

This concept of optical sterilization can be extended to include an additional step in the process wherein the light source is first applied in an unfocused manner, covering the target area with an illuminated area that extends 100 $\mu$m or more beyond the actual size of the micropore to be produced. By selecting the area over which the unfocused beam is to be applied, the flux density can be correspondingly reduced to a level well below the ablation threshold but high enough to effectively sterilize the surface of the skin. After a sufficiently long exposure of the larger area, either in one continuous step or in a series of pulses, to the sterilizing beam, the system is then configured into the sharply focused ablation mode and the optical microporation process begins.

Another illustrative embodiment of the invention is to create the required heat probe from a metallic solid, such as a small diameter wire. As in the previously described embodiment, the contacting surface of tie heat probe must be able to have its temperature modulated from ambient skin temperatures (33° C.) to temperatures greater than 123° C., within the required time allowed of, preferably, between about 1 to 50 ms at the high temperature (on-time) and at least about 10 to 50 ms at the low temperature (off-time). In particular, being able to modulate the temperature up to greater than 150° C. for an "on" time of around 5 ms and an off time of 50 ms produces very effective thermal ablation with little or no sensation to the individual.

Figure 4:
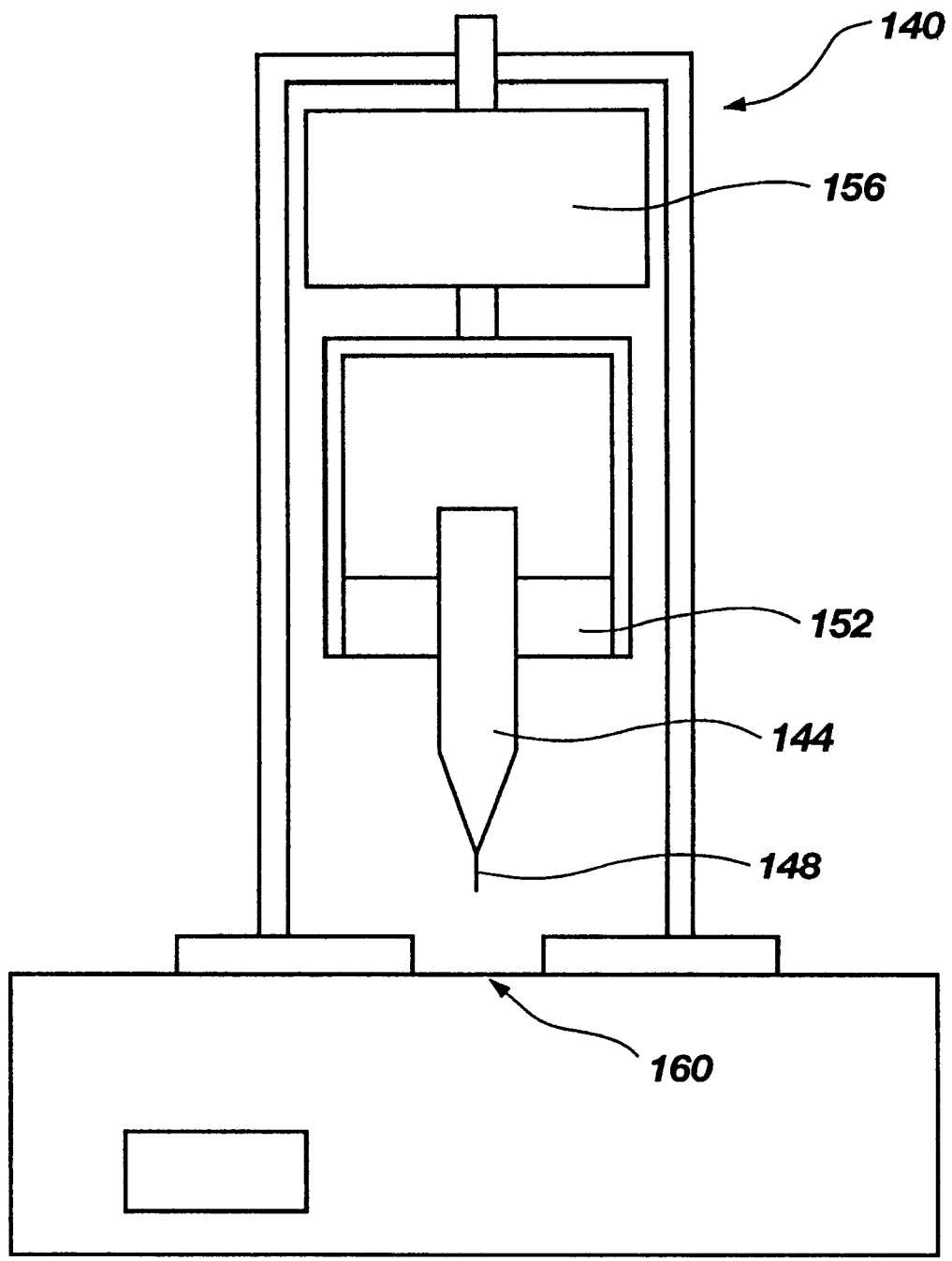
FIG. 4 shows a schematic representation of an ohmic heating device with a mechanical actuator.

Several methods for modulating the temperatures of the wire heat probe contact area may be successfully implemented. For example, a short length of wire may be brought up to the desired high temperature by an external heating element such as an ohmic heating element used in the tip of a soldering iron. FIG. 4 shows an ohmic heating device 140 with a mechanical actuator. The ohmic heating device comprises an ohmic heat source 144 coupled to a wire heat probe 148. The ohmic heat source is also coupled through an insulating mount 152 to a mechanical modulation device 156, such as a solenoid. In this configuration, a steady state condition can be reached wherein the tip of the wire probe will stabilize at some equilibrium temperature defined by the physical parameters of the structure, i.e., the temperature of the ohmic heat source, the length and diameter of the wire, the temperature of the air surrounding the wire, and the material of which the wire is comprised. Once the desired temperature is achieved, the modulation of the temperature of the selected area of an individual's skin 160 is effected directly via the mechanical modulation device to alternatively place the hot tip of the wire in contact with the skin for, preferably, a 5 ms on-time and then withdraw it into the air for, preferably, a 50 ms off-time.

Figure 5:
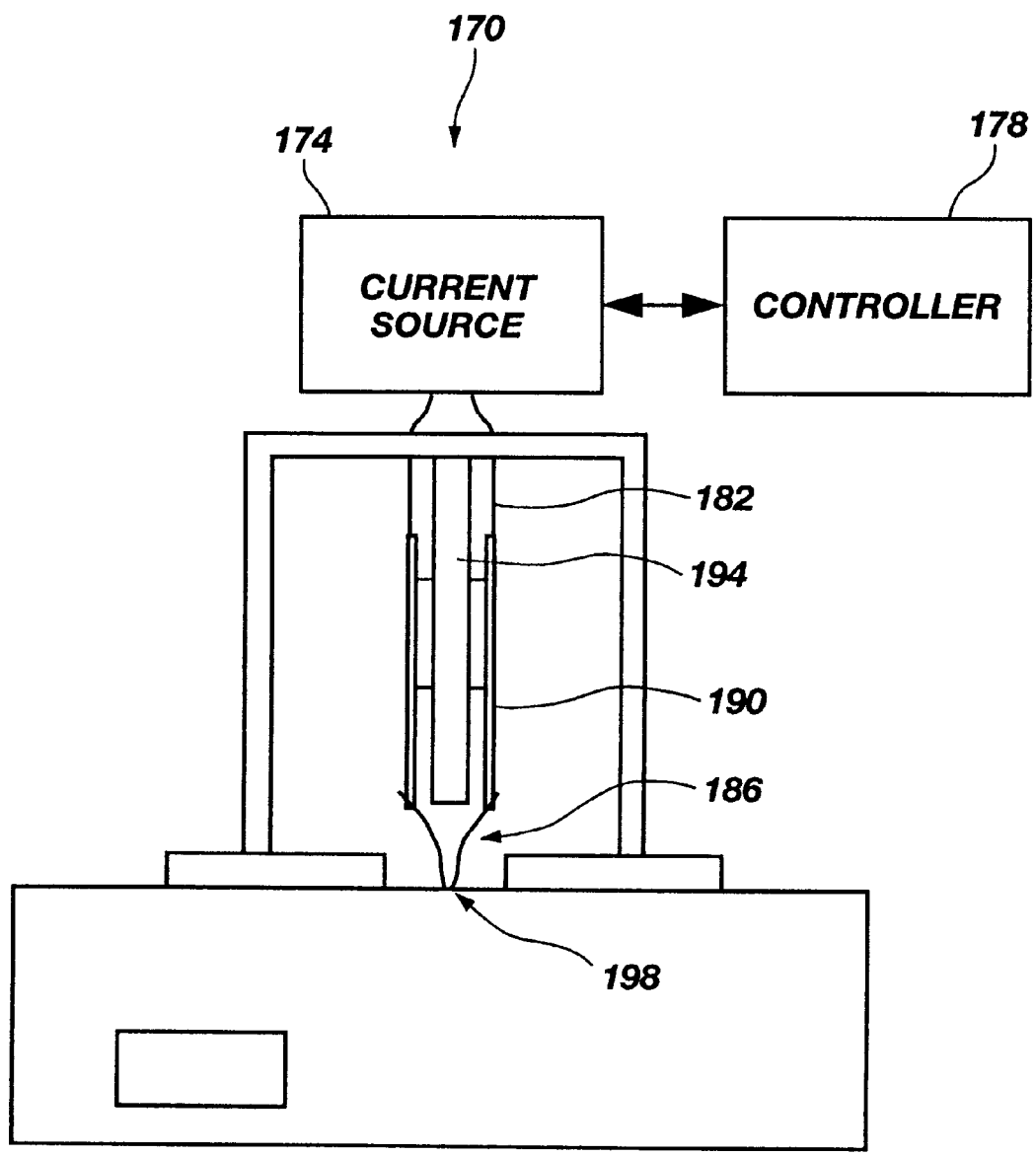
FIG. 5 shows a schematic representation of a high resistance current loop heating device.

Another illustrative example (FIG. 5), shows a device 170 comprising a current source 174 coupled to a controller 178. The current source is coupled to a current loop 182 comprising a wire 186 formed into a structure such that it presents a high resistance point. Preferably, the wire is held on a mount 190, and an insulator 194 separates different parts of the current loop. The desired modulation of temperature is then achieved by merely modulating the current through the wire. If the thermal mass of the wire element is appropriately sized and the heat sinking provided by the electrodes connecting it to the current source is sufficient, the warm-up and cool-down times of the wire element can be achieved in a few milliseconds. Contacting the wire with a selected area of skin 198 heats the stratum corneum to achieve the selected ablation.

Figure 6:
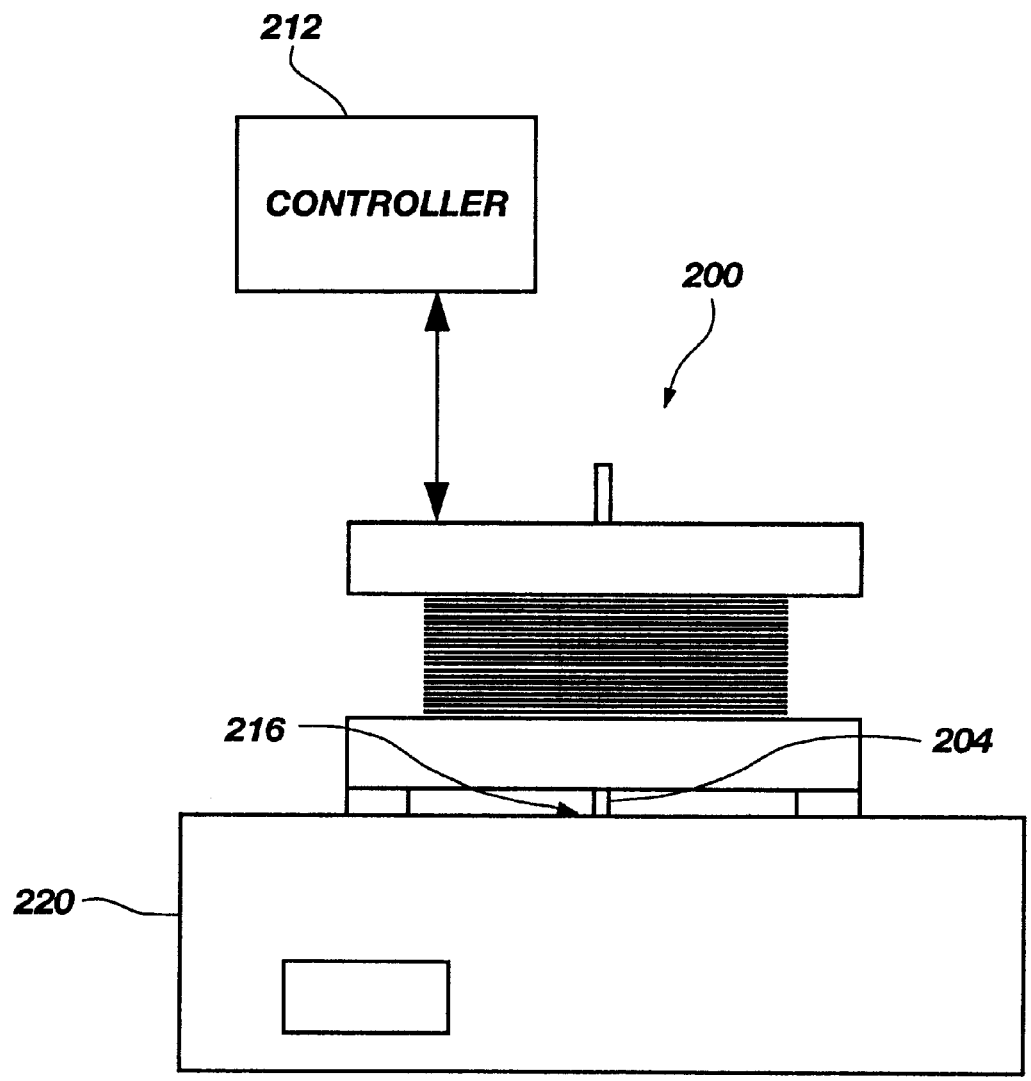
FIG. 6 shows a schematic representation of a device for modulating heating using inductive heating.

In FIG. 6 there is shown still another illustrative example of porating the stratum corneum with a hot wire. In this system 200, the wire 204 can be positioned within a modulatable alternating magnetic field formed by a coil of wire 208, the excitation coil. By energizing the alternating current in the excitation coil by means of a controller 212 coupled thereto, eddy currents can be induced in the wire heat probe of sufficient intensity that it will be heated up directly via the internal ohmic losses. This is essentially a miniature version of an inductive heating system commonly used for heat treating the tips of tools or inducing out-gassing from the electrodes in vacuum or flash tubes. The advantage of the inductive heating method is that the energy delivered into the wire heat probe can be closely controlled and modulated easily via the electronic control of the excitation coil. If the thermal mass of the wire probe itself, and the thermal mass of the stratum corneum in contact with the tip of the probe are known, controlling the inductive energy delivered can produce very precise control of the temperature at the contact point 216 with the skin 220. Because the skin tissue is essentially non-magnetic at the lower frequencies at which inductive heating can be achieved, if appropriately selected frequencies are used in the excitation coil, then this alternating electromagnetic field will have no effect on the skin tissues.

If a mechanically controlled contact modulation is employed, an additional feature may be realized by incorporating a simple closed loop control system wherein the electrical impedance between the probe tip and the subject's skin is monitored. In this manner, the position of the probe can be brought into contact with the subject's skin, indicated by the stepwise reduction in resistance once contact is made, and then held there for the desired "on-time," after which it can be withdrawn. Several types of linear actuators are suitable for this form of closed loop control, such as a voice-coil mechanism, a simple solenoid, a rotary system with a cam or bell-crank, and the like. The advantage is that as the thermal ablation progresses, the position of the thermal probe tip can be similarly advanced into the skin, always ensuring good a contact to facilitate the efficient transfer of the required thermal energy. Also, the change in the conductivity properties of the stratum corneum and the epidermis can be used to provide an elegant closed loop verification that the poration process is complete, i.e., when the resistance indicates that the epidermis has been reached, it is time to stop the poration process.

Figure 7:
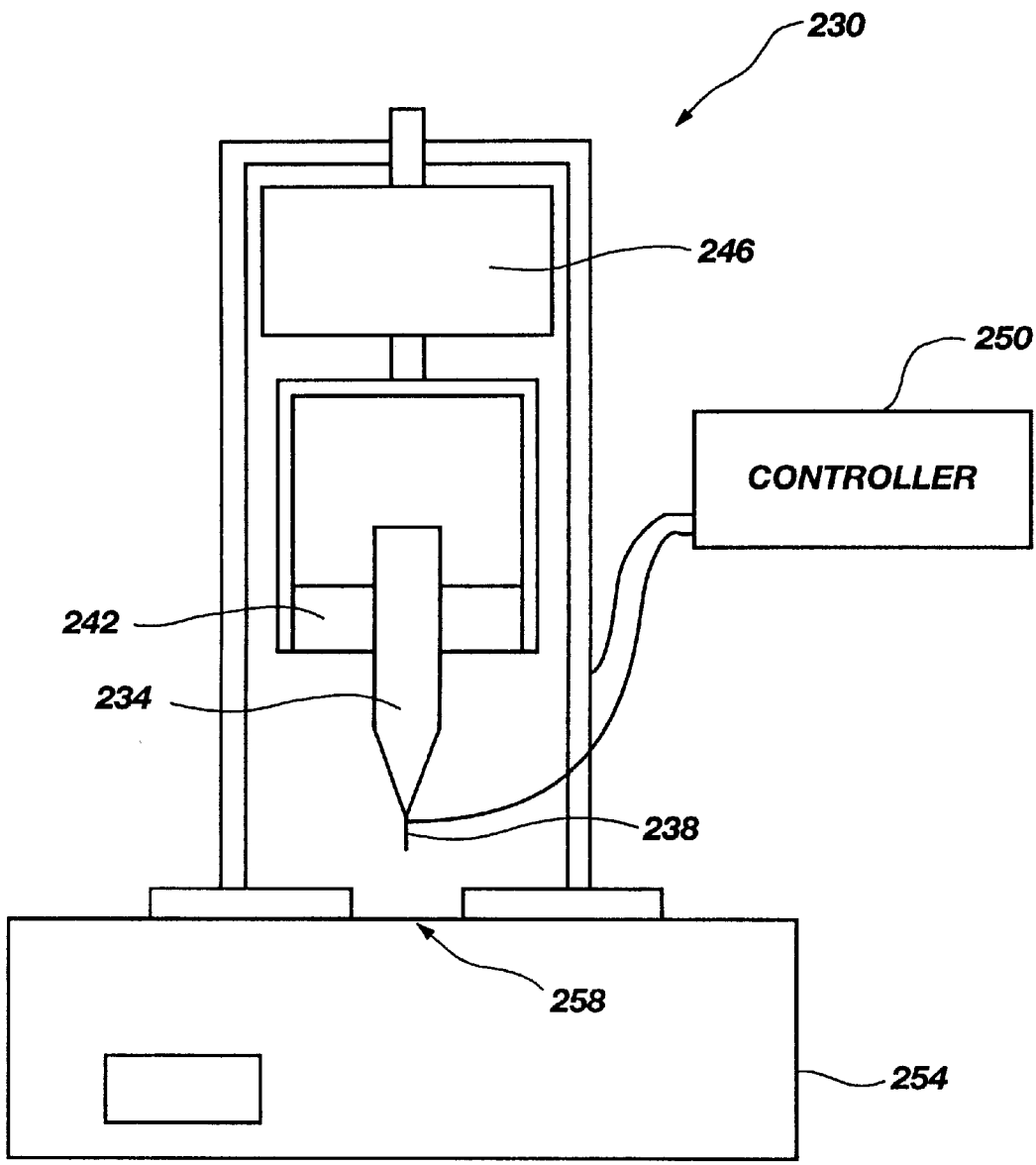
FIG. 7 shows a schematic representation of a closed loop impedance monitor using changes in impedance to determine the extent of poration.

FIG. 7 shows an illustrative example of such a closed loop impedance monitor. In this system 230, there is an ohmic heat source 234 coupled to a wire heat probe 238. The heat source is mounted through an insulating mount 242 on a mechanical modulator 246. A controller 250 is coupled to the wire and to the skin 254, wherein the controller detects changes in impedance in the selected area 258 of skin, and when a predetermined level is obtained the controller stops the poration process.

Along the same line as hydraulic poration means are microlancets adapted to just penetrate the stratum corneum for purposes of administering a permeant, such as a drug, through the pore formed or to withdraw an analyte through the pore for analysis. Such a device is considered to be "minimally invasive" as compared to devices and/or techniques which are non-invasive. The use of micro-lancets that penetrate below the stratum corneum for withdrawing blood are well known. Such devices are commercially available from manufacturers such as Becton-Dickinson and Lifescan and can be utilized in the present invention by controlling the depth of penetration. As an example of a micro-lancet device for collecting body fluids, reference is made to Erickson et al., International Published PCT Application WO 95/10223 (published Apr. 20, 1995). This application shows a device for penetration into the dermal layer of the skin, without penetration into subcutaneous tissues, to collect body fluids for monitoring, such as for blood glucose levels.

Poration of stratum corneum can also be accomplished using sonic means. Sonicporation is a variation of the optical means described above except that, instead of using a light source, a very tightly focused beam of sonic energy is delivered to the area of the stratum corneum to be ablated. The same levels of energy are required, i.e. a threshold of 70 $mJ/cm^2/50$ ms still must be absorbed. The same pulsed focused ultrasonic transducers as described in parent applications Ser. Nos. 08/152,442 and 08/152,174 can be utilized to deliver the required energy densities for ablation as are used in the delivery of sonic energy which is modulated in intensity, phase, or frequency or a combination of these parameters for the transdermal sampling of an analyte or the transdermal delivery of drugs. This has the advantage of allowing use of the same transducer to push a drug through the stratum corneum or pull a body fluid to the surface for analysis to be used to first create a micro-pore.

Additionally, electroporation or short bursts or pulses of electrical current can be delivered to the stratum corneum with sufficient energy to form micropores. Electroporation is known in the art for producing pores in biological membranes and electroporation instruments are commercially available. Thus, a person of skill in this art can select an instrument and conditions for use thereof without undue experimentation according to the guidelines provided herein.

The micropores produced in the stratum corneum by the methods of the present invention allow high flux rates of large molecular weight therapeutic compounds to be delivered transdermally. In addition, these non-traumatic microscopic openings into the body allow access to various analytes within the body, which can be assayed to determine their internal concentrations.

EXAMPLE 1

In this example, skin samples were prepared as follows. Epidermal membrane was separated from human cadaver whole skin by the heat-separation method of Klingman and Christopher, 88 *Arch. Dermatol.* 702 (1963), involving the exposure of the full thickness skin to a temperature of 60° C. for 60 seconds, after which time the stratum corneum and part of the epidermis (epidermal membrane) were gently peeled from the dermis.

EXAMPLE 2

Heat separated stratum corneum samples prepared according to the procedure of Example 1 were cut into 1 $cm^2$ sections. These small samples were than attached to a glass cover slide by placing them on the slide and applying an pressure sensitive adhesive backed disk with a 6 mm hole in the center over the skin sample. The samples were then ready for experimental testing. In some instances the skin samples were hydrated by allowing them to soak for several hours in a neutral buffered phosphate solution or pure water.

As a test of these untreated skin samples, the outputs of several different infrared laser diodes, emitting at roughly 810, 905, 1480 and 1550 nanometers were applied to the sample. The delivery optics were designed to produce a focal waist 25 µm across with a final objective have a numerical aperture of 0.4. The total power delivered to the focal point was measured to be between 50 and 200 milliwatts for the 810 and 1480 nm laser diodes, which were capable of operating in a continuous wave (CW) fashion. The 905 and 1550 nm laser diodes were designed to produce high peak power pulses roughly 10 to 200 nanoseconds long at repetition rates up to 5000 Hz. For the pulsed lasers the peak power levels were measured to be 45 watts at 905 nm and 3.5 watts at 1550 nm.

Under these operating conditions, there was no apparent effect on the skin samples from any of the lasers. The targeted area was illuminated continuously for 60 seconds and then examined microscopically, revealing no visible effects. In addition, the sample was placed in a modified Franz cell, typically used to test transdermal delivery systems based on chemical permeation enhancers, and the conductivity from one side of the membrane to the other was measured both before and after the irradiation by the laser and showed no change. Based on these tests which were run on skin samples from four different donors, it was concluded that at these wavelengths the coupling of the optical energy into the skin tissue was so small that no effects are detectable.

EXAMPLE 3

To evaluate the potential sensation to a living subject when illuminated with optical energy under the conditions of Example 2, six volunteers were used and the output of each laser source was applied to their fingertips, forearms, and the backs of their hands. In the cases of the 810, 905 and 1550 nm lasers, the subject was unable to sense when the laser was turned on or off. In the case of the 1480 nm laser, there was a some sensation during the illumination by the 1480 nm laser operating at 70 mW CW, and a short while later a tiny blister was formed under the skin due to the absorption of the 1480 nm radiation by one of the water absorption bands. Apparently the amount of energy absorbed was sufficient to induce the formation of the blister, but was not enough to cause the ablative removal of the stratum corneum. Also, the absorption of the 1480 nm light occurred predominantly in the deeper, fully hydrated (85% to 90% water content) tissues of the epidermis and dermis, not the relatively dry (10% to 15% water content) tissue of the stratum corneum.

EXAMPLE 4

Having demonstrated the lack of effect on the skin in its natural state (Example 3), a series of chemical compounds was evaluated for effectiveness in absorbing the light energy and then transferring this absorbed energy, via conduction, into the targeted tissue of the stratum corneum. Compounds tested included India ink; "SHARPIE" brand indelible black, blue, and red marking pens; methylene blue; fuschian red; epolite #67, an absorbing compound developed for molding into polycarbonate lenses for protected laser goggles; tincture of iodine; iodine-polyvinylpyrrolidone complex ("BETADINE"); copper phthalocyanine; and printers ink.

Using both of the CW laser diodes described in Example 2, positive ablation results were observed on the in vitro samples of heat-separated stratum corneum prepared according to Example 1 when using all of these products, however some performed better than others. In particular the copper phthalocyanine (CPC) and the epolite #67 were some of the most effective. One probable reason for the superior performance of the CPC is its high boiling point of greater the 500° C. and the fact that it maintains its solid phase up to this temperature.

EXAMPLE 5

As copper phthalocyanine has already been approved by the FDA for use in implantable sutures, and is listed in the Merck index as a rather benign and stabile molecule in regard to human biocompatability, the next step taken was to combine the topical application of the CPC and the focused light source to the skin of healthy human volunteers. A suspension of finely ground CPC in isopropyl alcohol was prepared. The method of application used was to shake the solution and then apply a small drop at the target site. As the alcohol evaporated, a fine and uniform coating of the solid phase CPC was then left on the surface of the skin.

The apparatus show in FIG. 1 was then applied to the site, wherein the CPC had been topically coated onto the skin, by placing the selected area of the individual's skin against a reference plate. The reference plate consists of a thin glass window roughly 3 cm×3 cm, with a 4 mm hole in the center. The CPC covered area was then positioned such that it was within the central hole. A confocal video microscope (FIG. 1) was then used to bring the surface of the skin into sharp focus. Positioning the skin to achieve the sharpest focus on the video system also positioned it such that the focal point of the laser system was coincident with the surface of the skin. The operator then activated the pulses of laser light while watching the effects at the target site on the video monitor. The amount of penetration was estimated visually by the operator by gauging the amount of defocusing of the laser spot in the micropore as the depth of the micropore increased, and this can be dynamically corrected by the operator, essentially following the ablated surface down into the tissues by moving the position of the camera/laser source along the "z" axis, into the skin. At the point when the stratum corneum had been removed down to the epidermis, the appearance of the base of the hole changed noticeably, becoming much wetter and shinier. Upon seeing this change, the operator deactivated the laser. In many instances, depending on the state of hydration of the subject as well as other physiological conditions, a dramatic outflow of interstitial fluid occurred in response to the barrier function of the stratum corneum being removed over this small area. The video system was used to record this visual record of the accessibility of interstitial fluid at the poration site.

EXAMPLE 6

The procedure of Example 5 was followed except that the CPC was applied to a transparent adhesive tape, which was then caused to adhere to a selected site on the skin of an individual. The results were substantially similar to those of Example 5.

EXAMPLE 7

Figure 8A:
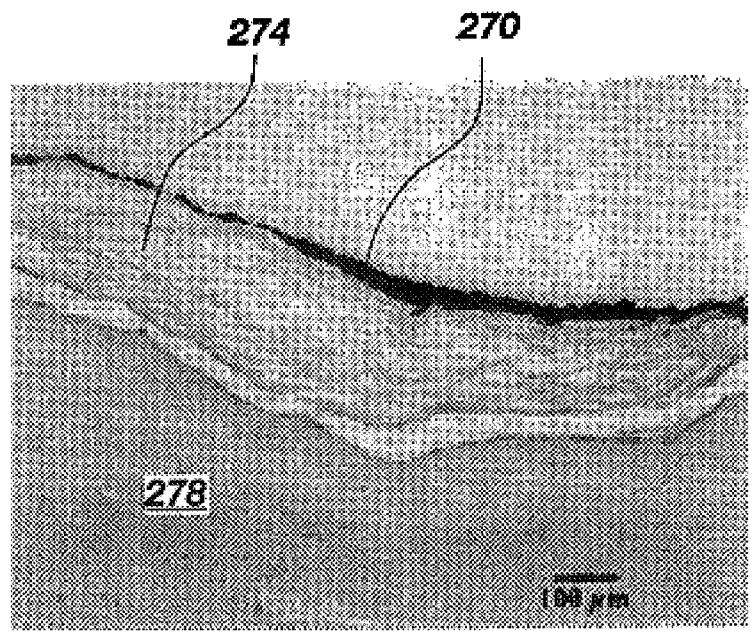
FIGS. 8A–D show cross sections of human skin treated with copper phthalocyanine and then subjected, respectively, to 0, 1, 5, and 50 pulses of 810 nm light with an energy density of 4000 J/cm$^2$ for a pulse period of 20 ms.
Figure 8B:
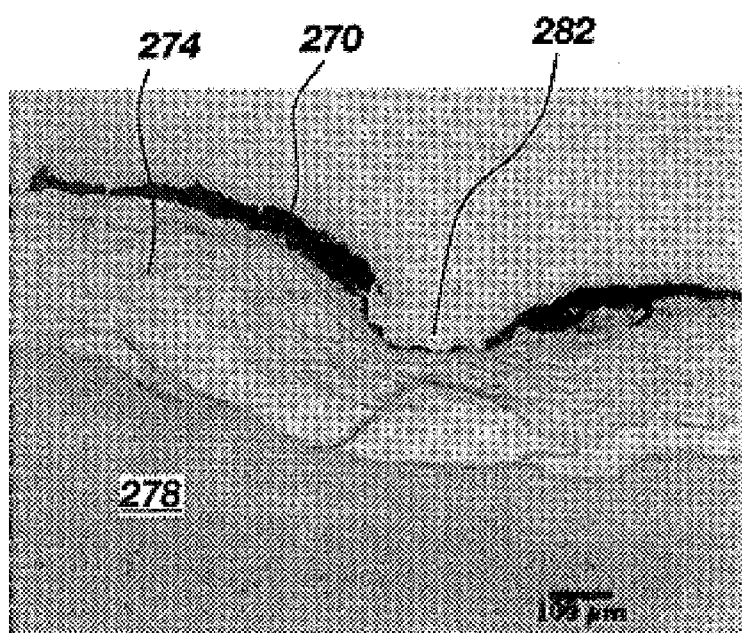
Figure 8C:
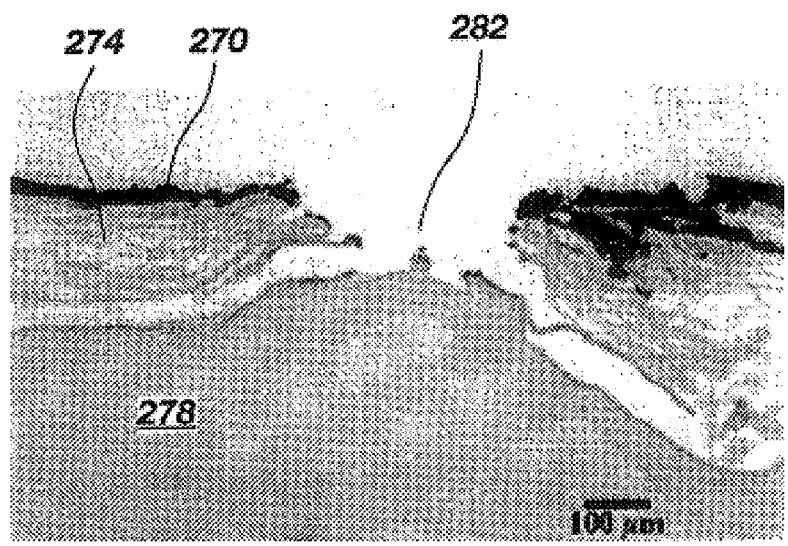
Figure 8D:
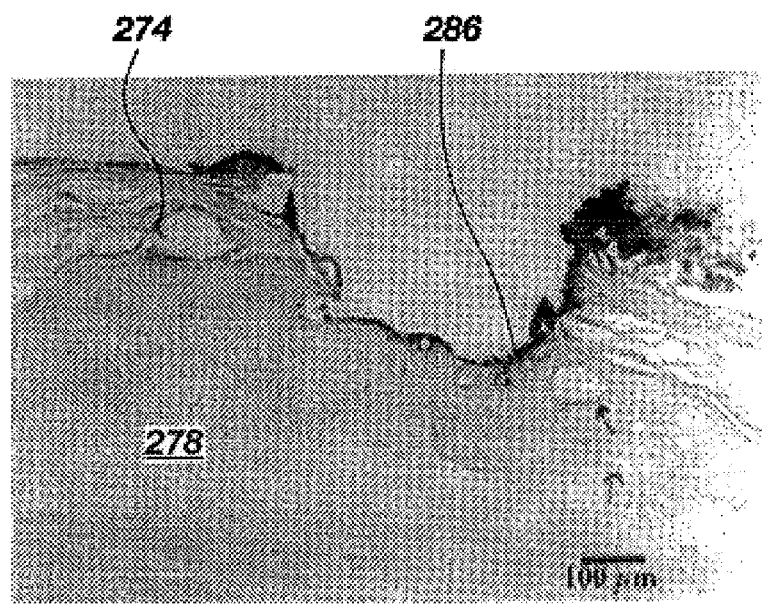

Histology experiments were performed on cadaver skin according to methods well known in the art to determine ablation threshold parameters for given dye mixtures and collateral damage information. The top surface of the skin sample was treated with a solution of copper phthalocyanine (CPC) in alcohol. After the alcohol evaporated, a topical layer of solid phase CPC was distributed over the skin surface with a mean thickness of 10 to 20 um. FIG. 8A shows a cross-section of full thickness skin prior to the laser application, wherein the CPC layer 270, stratum corneum 274, and underlying epidermal layers 278 are shown. FIG. 8B shows the sample after a single pulse of 810 nm light was applied to an 80 um diameter circle with an energy density of 4000 J/cm2, for a pulse period of 20 ms. It is noteworthy that there was still a significant amount of CPC present on the surface of the stratum corneum even in the middle of the ablated crater 282. It should also be noted that laboratory measurements indicate that only about 10% of the light energy incident on the CPC is actually absorbed, with the other 90% being reflected or backscattered. Thus the effective energy flux being delivered to the dye layer which could cause the desired heating is only about 400 J/cm2. 8C shows the sample after 5 pulses of 810 nm light were applied, wherein the stratum corneum barrier was removed with no damage to the underlying tissue. These results are a good representation of the "ideal" optically modulated thermal ablation performance. FIG. 8D shows the sample after 50 pulses were applied. Damaged tissue 286 was present in the epidermal layers due to carbonization of non ablated tissue and thermal denaturing of the underlying tissue. FIGS. 8A–8C show separations between the stratum corneum and the underlying epidermal layers due to an artifact pf dehydration, freezing, and preparations for imaging.

EXAMPLE 8

To examine the details of the thermal ablation mechanism, a mathematical model of the skin tissues was constructed upon which various different embodiments of the thermal ablation method could be tried. This model computes the temperature distribution in a layered semi-infinite medium with a specified heat flux input locally on the surface and heat removal from the surface some distance away, i.e. convection is applied between the two. The axisymmetric, time-dependent diffusion equation is solved in cylindrical coordinates using the alternating-direction-implicit (ADI) method. (Note: Constant Temp. B.C. is applied on lower boundary to serve as z–>inf; and zero radial heat flux is applied on max radial boundary to serve as r–>inf). The layers are parallel to the surface and are defined as: (1) dye; (2) stratum corneum; (3) underlying epidermis; and (4) dermis. The depth into the semi-infinite medium and thermal properties, density (rho), specific heat (c), and conductivity (k) must be specified for each layer.

First, a heat-transfer coefficient, h, on the skin is computed based on the "steady," "I-D," temperature distribution determined by the ambient air temperature, skin surface temperature, and dermis temperature. It is assumed that there is no dye present and provides "h" on the skin surface. The program then allows one to use this "h" on the dye layer surface or input another desired "h" for the dye surface. Next, the "steady" temperature distribution is computed throughout all layers (including the dye layer) using the specified "h" at the dye surface. This temperature distribution is the initial condition for the time-dependent heating problem. This constitutes the "m-file" initial.m. The program then solves for the time-dependent temperature distribution by marching in time, computing and displaying the temperature field at each step.

Each embodiment of the method described herein, for which empirical data have been collected, has been modeled for at least one set of operational parameters, showing how stratum corneum ablation can be achieved in a precise and controllable fashion. The output of the simulations is presented graphically in two different formats: (1) a cross-sectional view of the skin showing the different tissue layers with three isotherms plotted on top of this view which define three critical temperature thresholds, and (2) two different temperature-vs-time plots, one for the point in the middle of the stratum corneum directly beneath the target site, and the second for the point at the boundary of the viable cell layers of the epidermis and the underside of the stratum corneum. These plots show how the temperature at each point varies with time as the heat pulses are applied as if one could implant a microscopic thermocouple into the tissues. In addition, the application of this model allows investigation of the parametric limits within which the method can be employed to set the outer limits for two important aspects of the methods performance. First, general cases are presented cases that define the envelope within which the method can be employed without causing pain or undesired tissue damage.

For any given heat source, as described in the several different embodiments of the invention, there is a point at which the effect on the subject's skin tissues becomes non-optimal in that the subject perceives a pain sensation, or that the viable cells in the underlying epidermis and/or dermis sustain temperatures, which if maintained for a long enough duration, will render damage to these tissues. Accordingly, a test simulation was run using the optically heated topical copper phthalocyanine (CPC) dye embodiment as a baseline method to establish how the thermal time constants of the different skin tissue layers essentially define a window within which the method can be employed without pain or damage to adjacent tissue layers.

FIGS. 9 and 10 show schematic cross-sectional views of the skin and the topical dye layer. In each figure, three distinct isotherms are displayed: (1) 123° C., the point at which vaporization of the water in the tissue produces an ablation of the tissue; (2) 70° C., the point at which viable cells will be damaged if this temperature is maintained for several seconds; and (3) 45° C., the average point at which a sensation of pain will be perceived by the subject. This pain threshold is described in several basic physiology texts, but experience shows this threshold to be somewhat subjective. In fact, in repeated tests on the same individual, different poration sites within a few millimeters of each other can show significantly different amounts of sensation, possibly due to the proximity to a nerve ending in relationship to the poration site.

The dimensions on the graphs show the different layers of the dye and skin, as measured in $\mu$m, with flat boundaries defining them. Whereas the actual skin tissues have much more convoluted boundaries, in a mean sense for the dimensions involved, the model provides a good approximation of the thermal gradients present in the actual tissues. The dimensions used in this, and all subsequent simulations, for the thicknesses of the CPC dye layer and the various skin layers are as follows: dye, 10 $\mu$m; stratum corneum, 30 $\mu$m; underlying epidermis, 70 $\mu$m; and dermis, 100 $\mu$m.

Additional conditions imposed on the model for this particular simulation are shown in the following tables:

TABLE 1

Initial Conditions for Finite Difference Thermal Model

| | |
|---|---|
| Ambient Air Temperature | Ta = 20° C. |
| Skin Surface Temperature | Ts = 30° C. |
| Dermis Temperature | Td = 37° C. |
| Dye Vaporization Temperature | Tvap = 550° C. |

TABLE 1-continued

Initial Conditions for Finite Difference Thermal Model

| S.C. Vaporization Temperature | Tc1 = 123° C. |
| Tissue Damage Temperature | Tc2 = 70° C. |
| "Pain" Temperature | Tc3 = 45° C. |
| Radius of Irradiated Area | $R_{hot}$ = 30 µm |
| Energy Density Applied | FLUX = 400 Joules/cm$^2$ |

TABLE 2

| Parameter | Dye | S.C. | Epidermis | Dermis |
| --- | --- | --- | --- | --- |
| Thermal Conductivity | 0.00046 | .00123 | 0.00421 | 0.00421 |
| Density | 0.67 | 1.28 | 1.09 | 1.09 |
| Specific Heat | 0.8 | 1.88 | 3.35 | 3.35 |

When these simulations are run, the following conservative assumptions are imposed:

1. While some portion of the stratum corneum may be shown as having a temperature already exceeded the ablation threshold for thermal vaporization of the water content, this event is not modeled, and the subsequent loss of heat energy in the tissues due to this vaporization is not factored into the simulation. This will cause a slight elevation in the temperatures shown in the underlying tissues from that point on in the simulation run.

2. Similarly, when some portion of the copper phthalocyanine (CPC) dye layer is shown to have reached its vaporization point of 550° C., this event is not modeled, but the temperature is merely hard-limited to this level. This will also cause a slight elevation of the subsequent temperatures in the underlying layers as the simulation progresses.

Even with these simplifications used in the model, the correlation between the predicted performance and the empirically observed performance based on both clinical studies and histological studies on donor tissue samples is remarkable. The key data to note in FIGS. 9 and 10 are the length of time which the heat pulse is applied, and the location of the three different threshold temperatures displayed by the isotherms.

In FIG. 9, with a pulse length of 21 milliseconds, the 70° C. isotherm just crosses the boundary separating the stratum corneium and the viable cell layers in the epidermis. In in vitro studies on donor skin samples under these conditions, fifty pulses of thermal energy delivered 50 milliseconds apart cause detectable damage to this top layer of living cells (see FIG. 8D). However, it was also shown in the in vitro studies that five pulses of heat energy at these same operating parameters, did not produce any significant damage to these tissues. It seems reasonable that even though the nominal damage threshold may have been exceeded, at least in a transient sense, this temperature must be maintained for some cumulative period of time to actually cause any damage to the cells. Nevertheless, the basic information presented by the simulation is that if one keeps the "on-time" of the heat pulse to less than 20 milliseconds with the flux density of 400 Joules/cm$^2$, then no damage to the living cells in the underlying epidermis will be sustained, even though the ablation threshold isotherm has been moved well into the stratum corneum. In other words, by using a low flux density thermal energy source, modulated such that the "on time" is suitably short, ablation of the stratum corneum can be achieved without any damage to the adjacent cells in the underlying epidermis (see FIG. 8C). This is possible in large part due to the significantly different thermal diffusivities of these two tissues layers. That is, the stratum corneum, containing only about 10% to 20% water content, has a much lower thermal conductivity constant, 0.00123 J/(S*cm*K), than the 0.00421J/(S*cm*K) of the epidermis. This allows the temperature to build up in the stratum corneum, while maintaining a tight spatial definition, to the point at which ablation will occur.

In FIG. 10, the same simulation scenario started in the damage threshold critical point run illustrated in FIG. 9 is carried out farther in time. By leaving the heat pulse on for 58 milliseconds at the same flux density of 400 Joules/cm$^2$ within the 60 µm diameter circle of dye being heated, the pain sensory isotherm at 45° C. just enters the enervated layer of skin comprised by the dermis. In addition, the damage threshold isotherm moves significantly farther into the epidermal layer than where it was shown to be in FIG. 9. Relating this simulation to the numerous clinical studies conducted with this method, an excellent verification of the model's accuracy is obtained in that the model shows almost exactly the duration of 'on-time' that the heat probe can be applied to the skin before the individual feels it. In clinical tests, a controllable pulse generator was used to set the "on-time" and "off-time" of a series of light pulses applied to the topical layer of copper phthalocyanine (CPC) dye on the skin. While maintaining a constant "off-time" of 80 milliseconds, the "on-time" was gradually increased until the subject reported a mild "pain" sensation. Without exception, all of the subjects involved in these studies, reported the first "pain" at an "on-time" of between 45 and 60 milliseconds, very close to that predicted by the model. In addition, the site-to-site variability mentioned previously as regards the sensation of "pain" was noted in these clinical studies. Accordingly, what is reported as "pain" is the point at which the first unambiguous sensation is noticeable. At one site this may be reported as pain, whereas at an adjacent site the same subject may report this as merely "noticeable."

One element of this clinical research is the realization that even at the same site, a non-uniform pulse-train of heat pulses may work with the subject's psycho-physiological neuro-perception to cause a genuine reduction in perceived sensation. For example, a series of shorter length heat pulses can be used to saturate the neurons in the area, momentarily depleting the neurotransmitters available at this synaptic junction and therefore limiting the ability to send a "pain" message. This then allows a longer pulse following these short pulses to be less noticeable than if it were applied at the beginning of the sequence. Accordingly, a series of experiments was conducted with some arbitrarily created pulse trains, and the results were consistent with this hypothesis. An analogy for this situation might be found in the perception when one first steps into a very hot bath that is painful at first, but quickly becomes tolerable as one acclimates to the heat sensation.

EXAMPLE 9

An object of this invention is to achieve a painless, micro-poration of the stratum corneum without causing any significant damage to the adjacent viable tissues. As described in the simulation illustrated in Example 8 and FIGS. 9–10, a boundary appears to exist for any given flux density of thermal energy within the ablation target spot within which the micro-poration can be achieved in just such a painless and non-traumatic manner. Both the in vivo and in vitro studies have shown that this is the case, and this has permitted development through empirical methods of some operational parameters that appear to work very well. The following set of simulations shows how the method works when these specific parameters are used.

Figure 11:
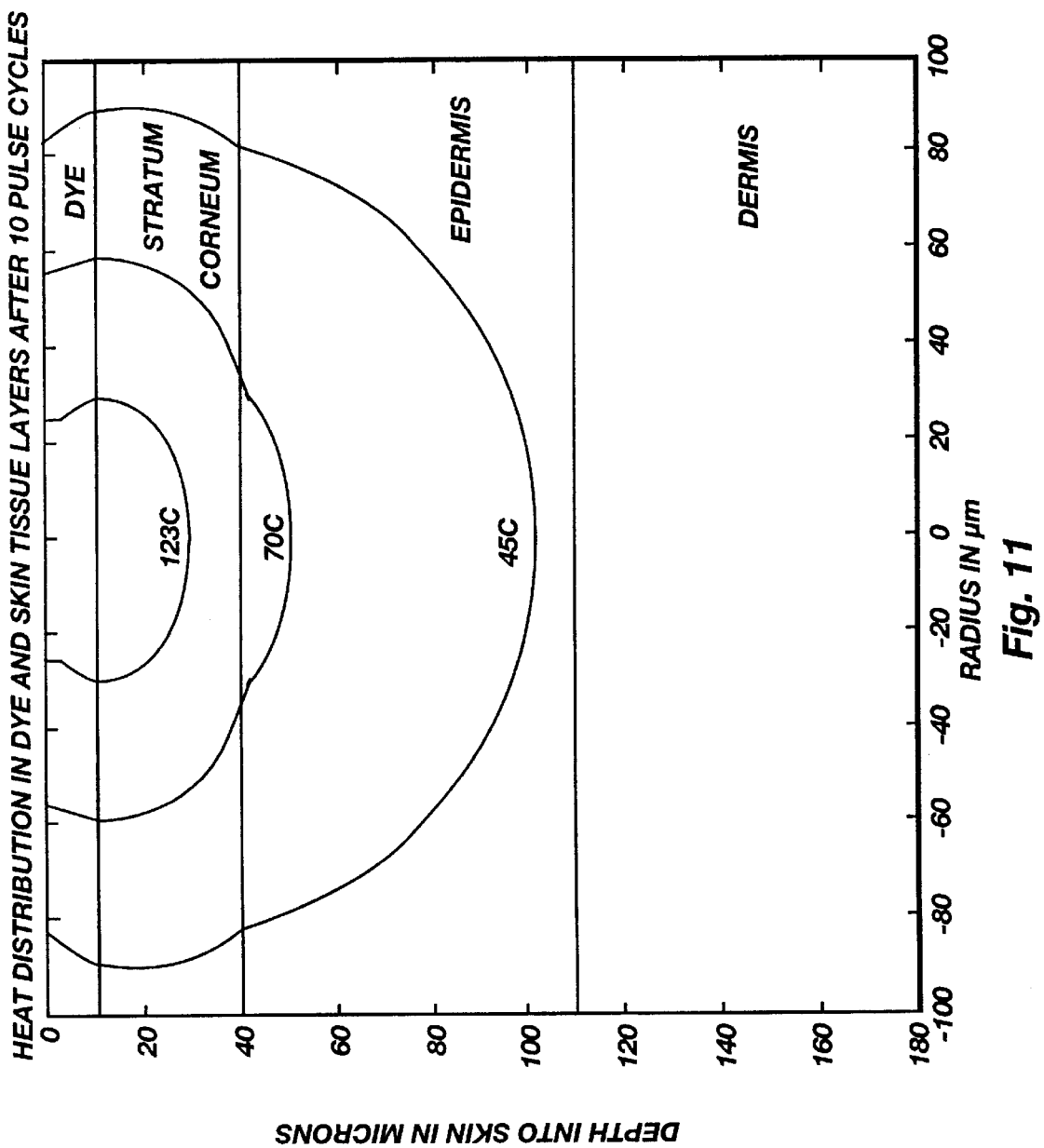
Figure 12:
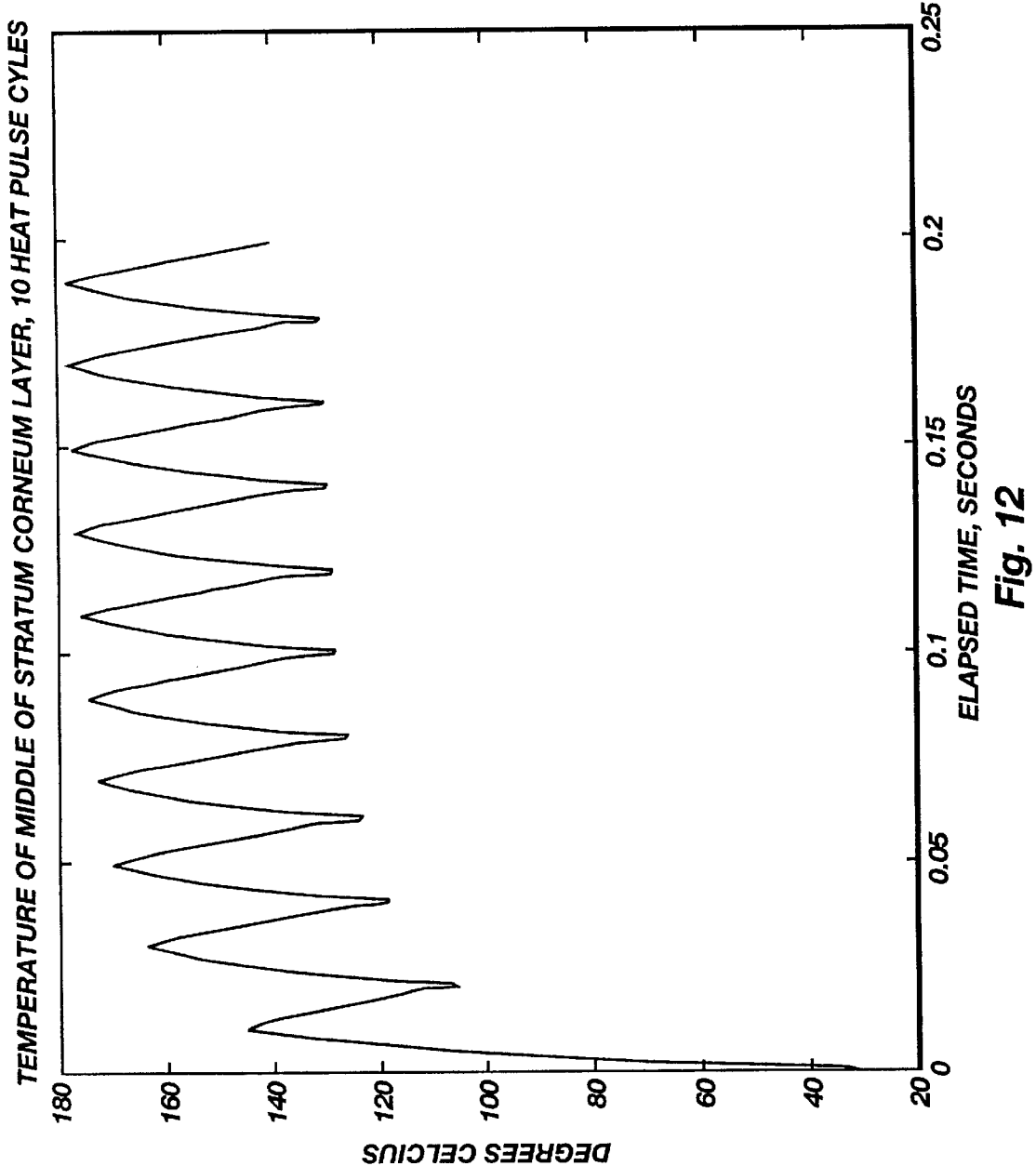
FIGS. 12 and 13 show graphic representations of temperature as a function of time in the stratum corneum and viable epidermis, respectively, during simulated thermal poration events using optical poration.
Figure 13:
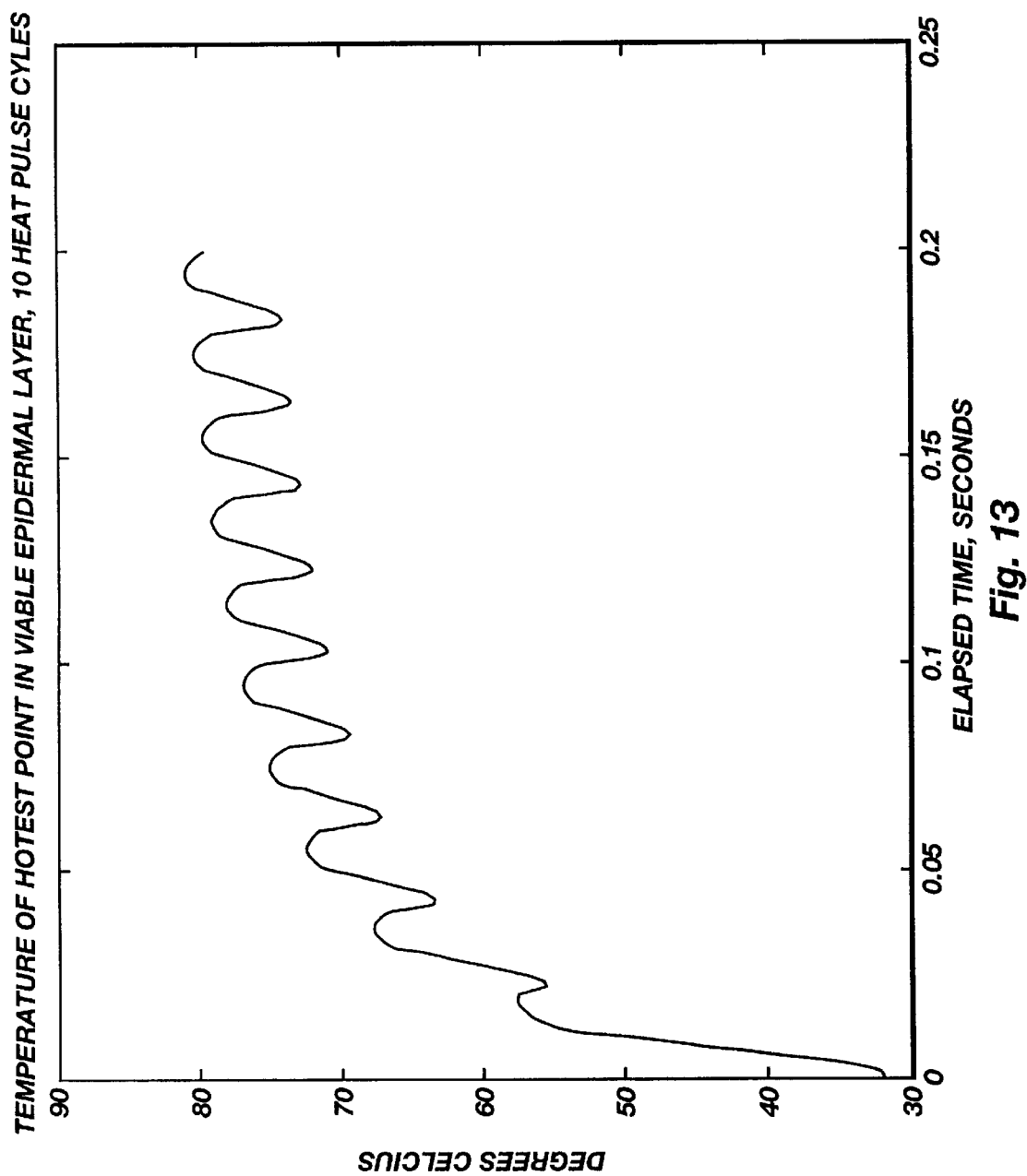
Figure 14:
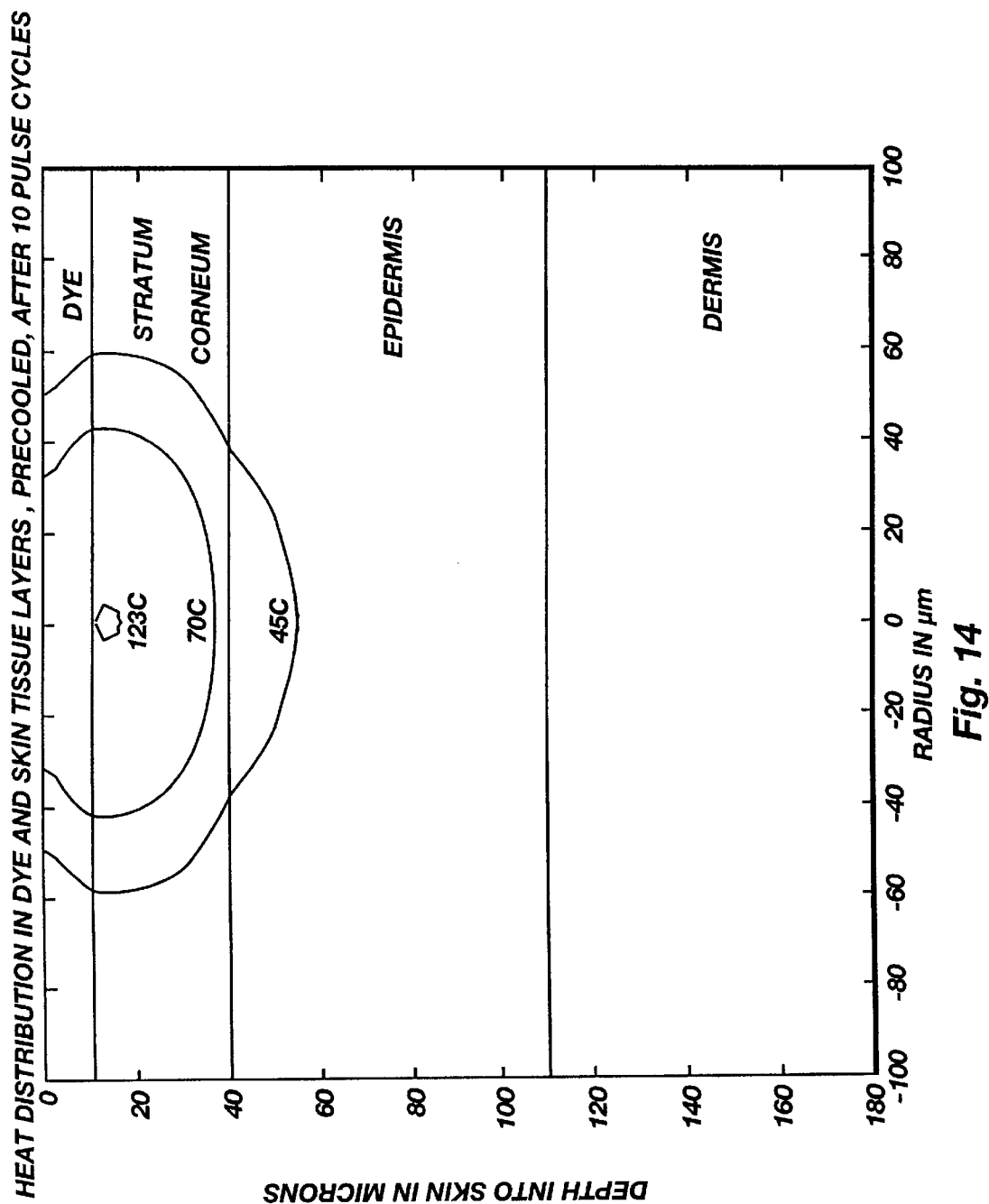
FIGS. 14–16 show graphic representations of temperature distribution, temperature as a function of time in the stratum corneum, and temperature as a function of time in the viable epidermis, respectively, during simulated thermal poration events using optical poration wherein the tissue was cooled prior to poration.
Figure 15:
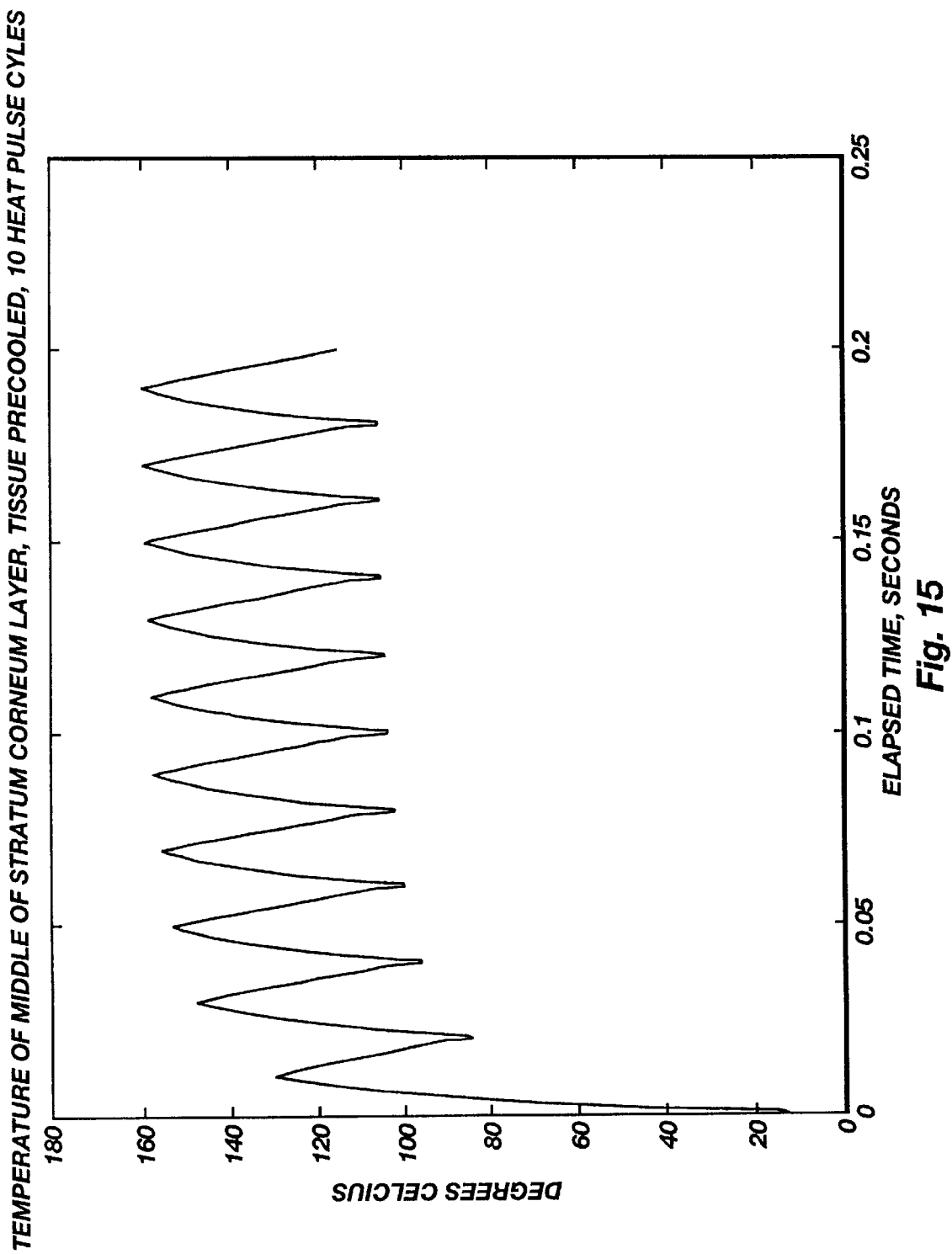
Figure 16:
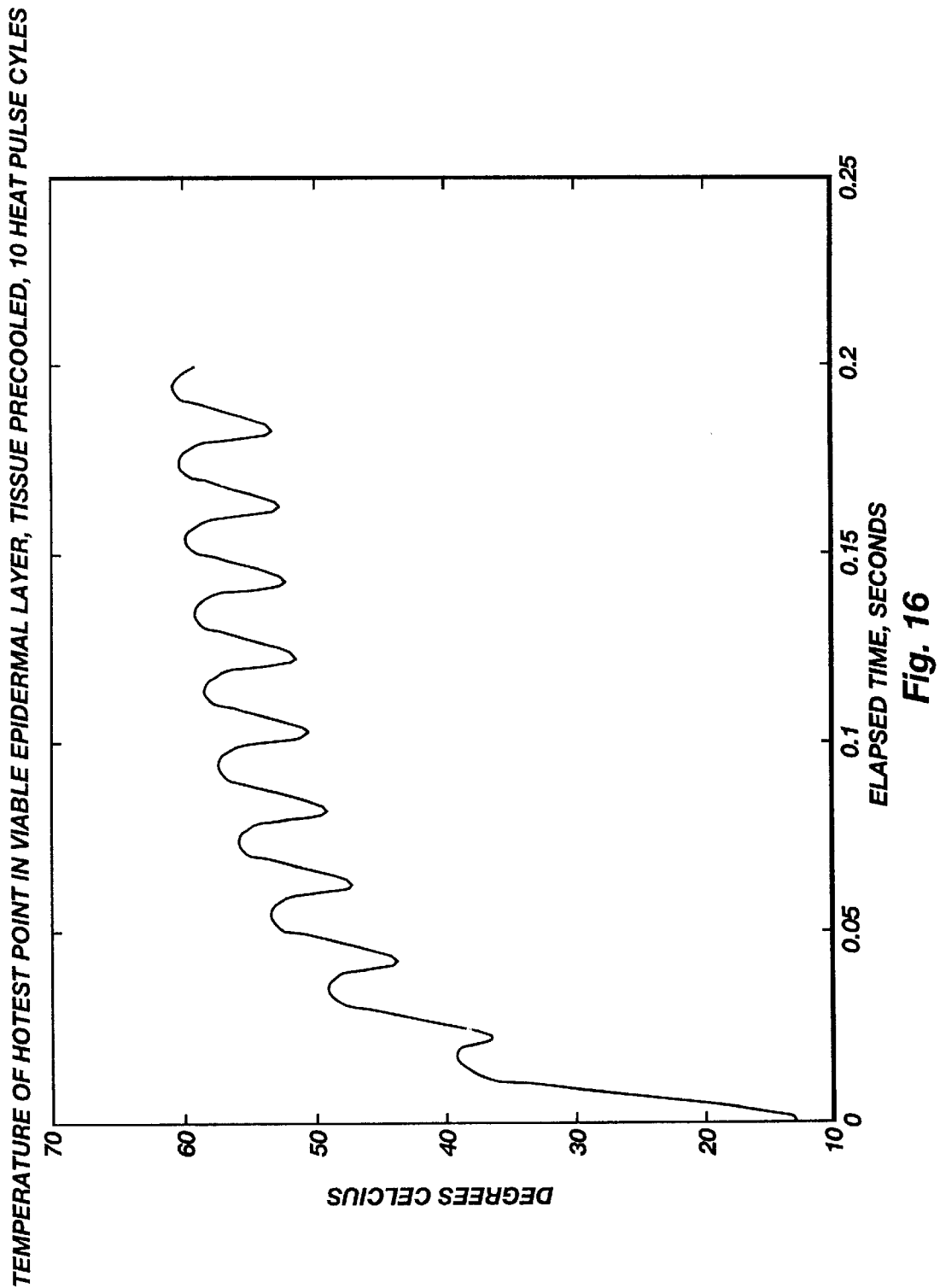

In the first case, a pulse train of ten pulses, 10 milliseconds "on-time" separated by 10 milliseconds "off-time" is applied to the CPC-covered skin. FIG. 11 shows the final temperature distribution in the skin tissues immediately after this pulse train has ended. As can be seen, the isotherms representing the three critical temperature thresholds show that stratum corneum ablation has been achieved, with no sensation present in the dermal layer nerves and very little cross-over of the damage threshold into the viable cells of the underlying epidermis. As mentioned previously, it appears that to actually do permanent cell damage, the epidermal cells must not only be heated up to a certain point, but they also must be held at this temperature for some period of time, generally thought to be about five seconds. FIGS. 12 and 13 show the temperature of the stratum corneum and the viable epidermis, respectively, as a function of time, showing heating during the "on-time" and cooling during the "off-time" for the entire ten cycles. Relating this simulation to the in vivo studies conducted, note that in better than 90% of the poration attempts with the system parameters set to match the simulation, effective poration of the stratum corneum was achieved without pain to the subject, and in subsequent microscopic examination of the poration site several days later, no noticeable damage to the tissues was apparent. The in vitro studies conducted on whole thickness donor skin samples were also consistent with the model's prediction of behavior.

EXAMPLE 10

In conducting both the empirical in vivo studies, and these simulations, it appears that prechilling of the skin aids in optimizing the micro-poration process for reducing the probability of pain or damage to adjacent tissues. In practice, this can easily be achieved using a simple cold-plate placed against the skin prior to the poration process. For example, applying a Peltier cooled plate to the 1 cm diameter circle surrounding the poration target site, with the plate held at roughly 5° C. for a few seconds, significantly reduces the temperature of the tissues. A schematic illustration of an experimental device used for this purpose in the laboratory is shown in FIGS. 3A–B. By applying exactly the same ten-cycle pulse train as used in the run illustrated in Example 9, one can see, by comparing FIG. 11 to FIG. 14, FIG. 12 to FIG. 15, and FIG. 13 to FIG. 16, how much improvement can be made in the control of the temperature penetration into the skin tissues. Once again, the relatively low thermal diffusivity and specific heat of the stratum corneum as compared to the epidermis and dermis is advantageous. Once cooled, the highly hydrated tissues of the epidermis and dermis require a much larger thermal energy input to elevate their temperatures, whereas the stratum corneum, with its relatively dry makeup, can quickly be heated up to the ablation threshold.

EXAMPLE 11

Once the basic thermal conduction mechanism of delivering the energy into the skin tissues underlying the effective painless ablation and micro-poration of the stratum corneum is understood, several different specific methods to achieve the required rapid temperature modulations of the contact point can be conceived, such as the hot wire embodiments illustrated in FIGS. 4–7.

A basic embodiment, as described herein, uses an Ohmic heating element (FIG. 4), such as the tip of a small cordless soldering iron, with a suitably sized, relatively non-reactive, wire wrapped around it with a short amount of the wire left to protrude away from the body of the heater. When electricity is applied with a constant current source, the heater will come up to some temperature and within a few seconds, achieve a steady state with the convection losses to the surrounding air. Similarly, the wire, which is a part of this thermal system, will reach a steady state such that the very tip of the wire can be raised to almost any arbitrary temperature, up to roughly 1000° C. with these types of components. The tip can be sized to give exactly the dimension micropore desired.

In the laboratory, tungsten wires with a diameter of 80 $\mu$m attached to the replaceable tip of a "WAHL" cordless soldering iron with approximately 2 mm of wire protruding from the tip have been utilized. With a thermocouple, the temperature of the tip has been measured at its steady state, and it has been noted that by varying the constant current settings, steady state temperatures of greater than 700° C. can easily be reached. To achieve the desired modulation, a low mass, fast response electromechanical actuator was coupled to the tip such that the position of the wire could be translated linearly more than 2 mm at up to a 200 Hz rate. Then, by mounting the entire apparatus on a precision stage, this vibrating tip could very controllably be brought into contact with the skin surface in a manner where it was only in contact for less than 10 milliseconds at a time, the "on-time," while an "off-time" of arbitrarily long periods could be achieved by setting the pulse generator accordingly. These in vivo studies showed that the poration could actually be achieved before the subject being porated even knew that the tip of the wire was being brought into contact with the skin.

Figure 17:
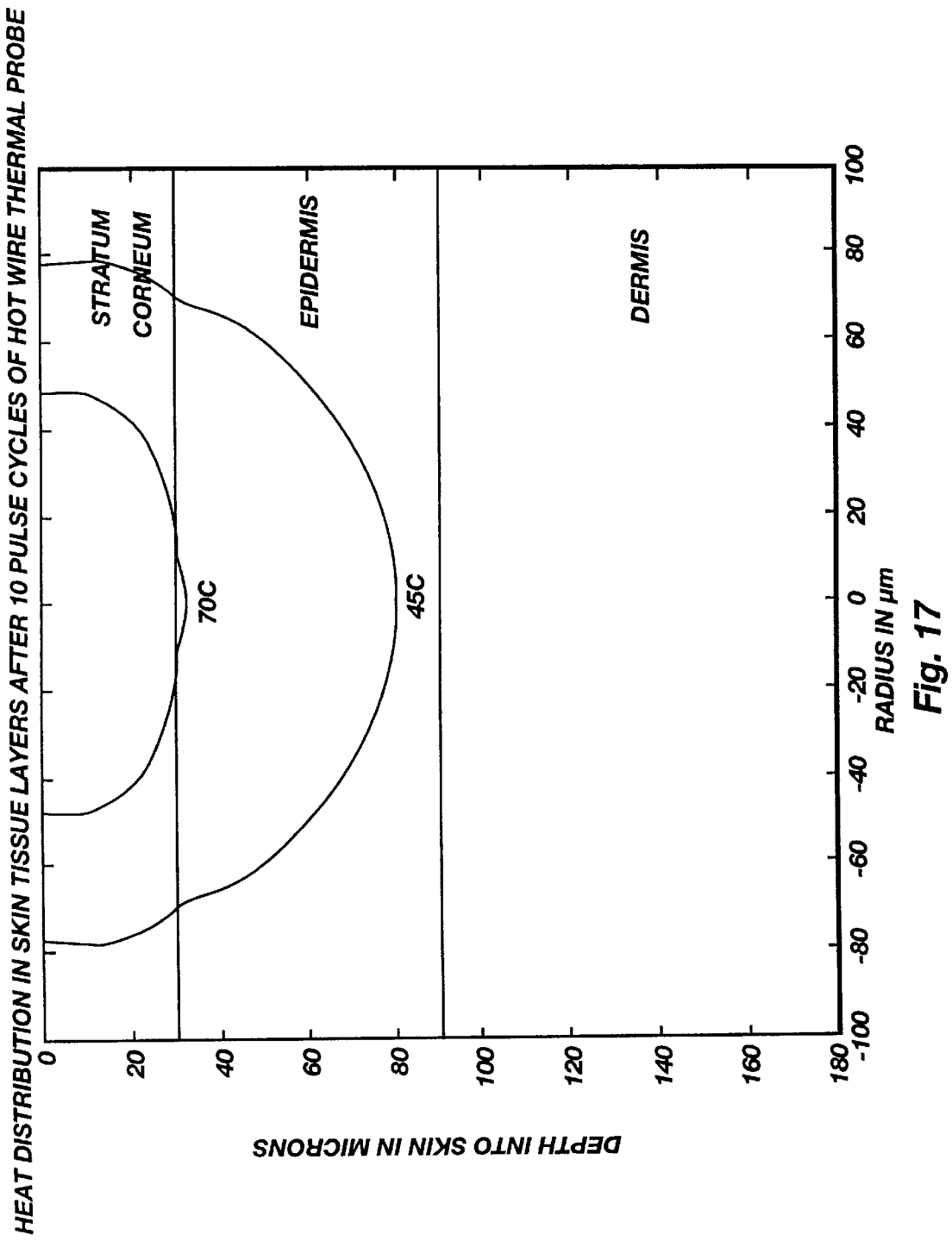
FIGS. 17–19 show graphic representations of temperature distribution, temperature as a function of time in the stratum corneum, and temperature as a function of time in the viable epidermis, respectively, during simulated thermal poration events wherein the tissue was heated with a hot wire.
Figure 18:
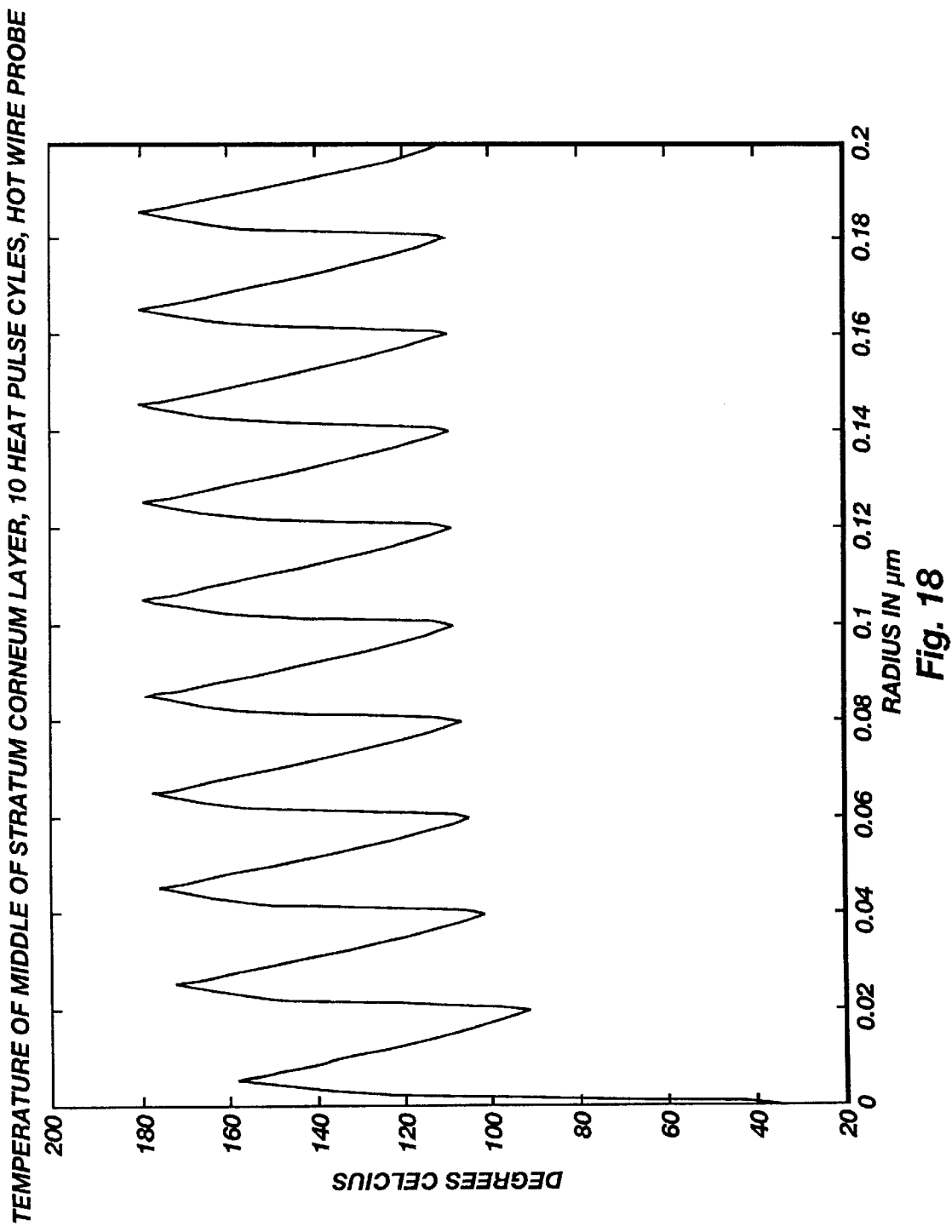
Figure 19:
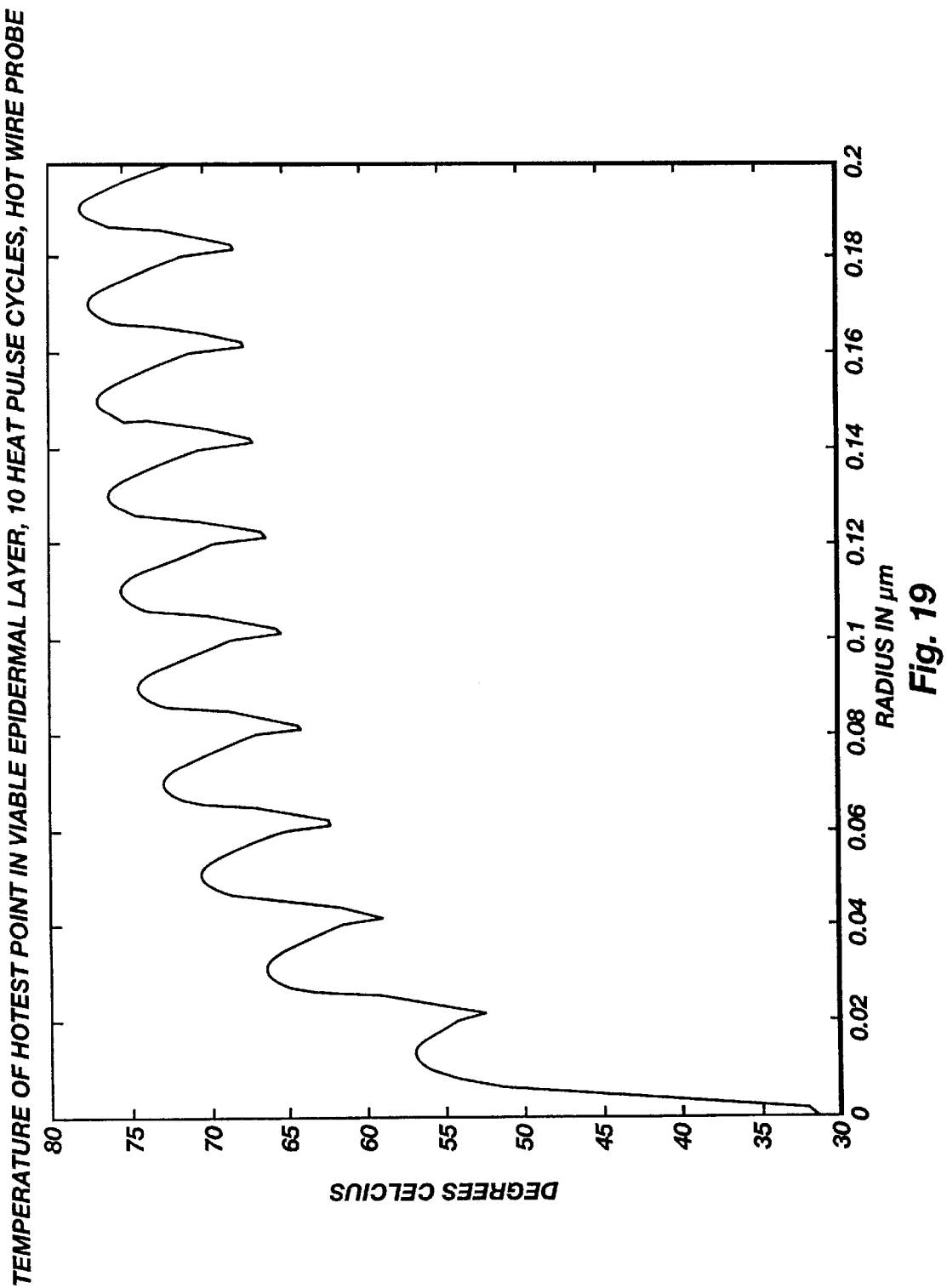

To compare the performance of this embodiment to the optically heated topical CPC dye embodiment, the following simulations were run according to the procedure of Example 8. Essentially, by only varying the initial conditions, the hot wire embodiment can be run with the identical simulation code. Because the contact with the wire occurs essentially instantly, there is no time dependent build-up of heat in the CPC dye layer and when the wire is physically removed from contact with the skin, there is a no residual heat still left on the surface as there is with the heated CPC dye layer. Also, as the wire itself defines the area targeted for ablation/micro-poration, there should be no lateral diffusion of thermal energy prior to its application to the stratum corneum. The comparative performances of the "hot-wire" embodiment are shown in FIGS. 17–19.

EXAMPLE 12

Figure 20:
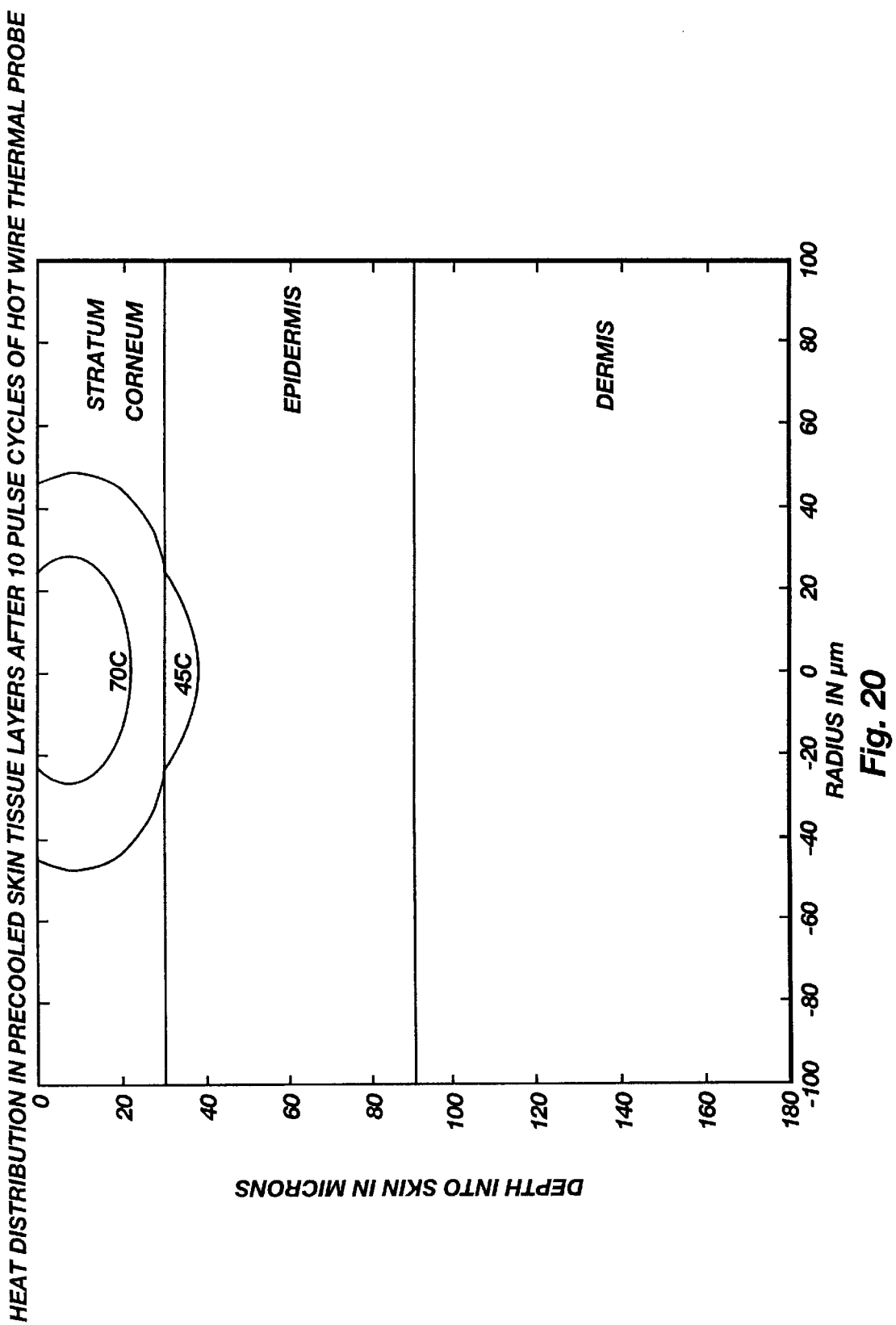
FIGS. 20–22 show graphic representations of temperature distribution, temperature as a function of time in the stratum corneum, and temperature as a function of time in the viable epidermis, respectively, during simulated thermal poration events wherein the tissue was heated with a hot wire and the tissue was cooled prior to poration.
Figure 21:
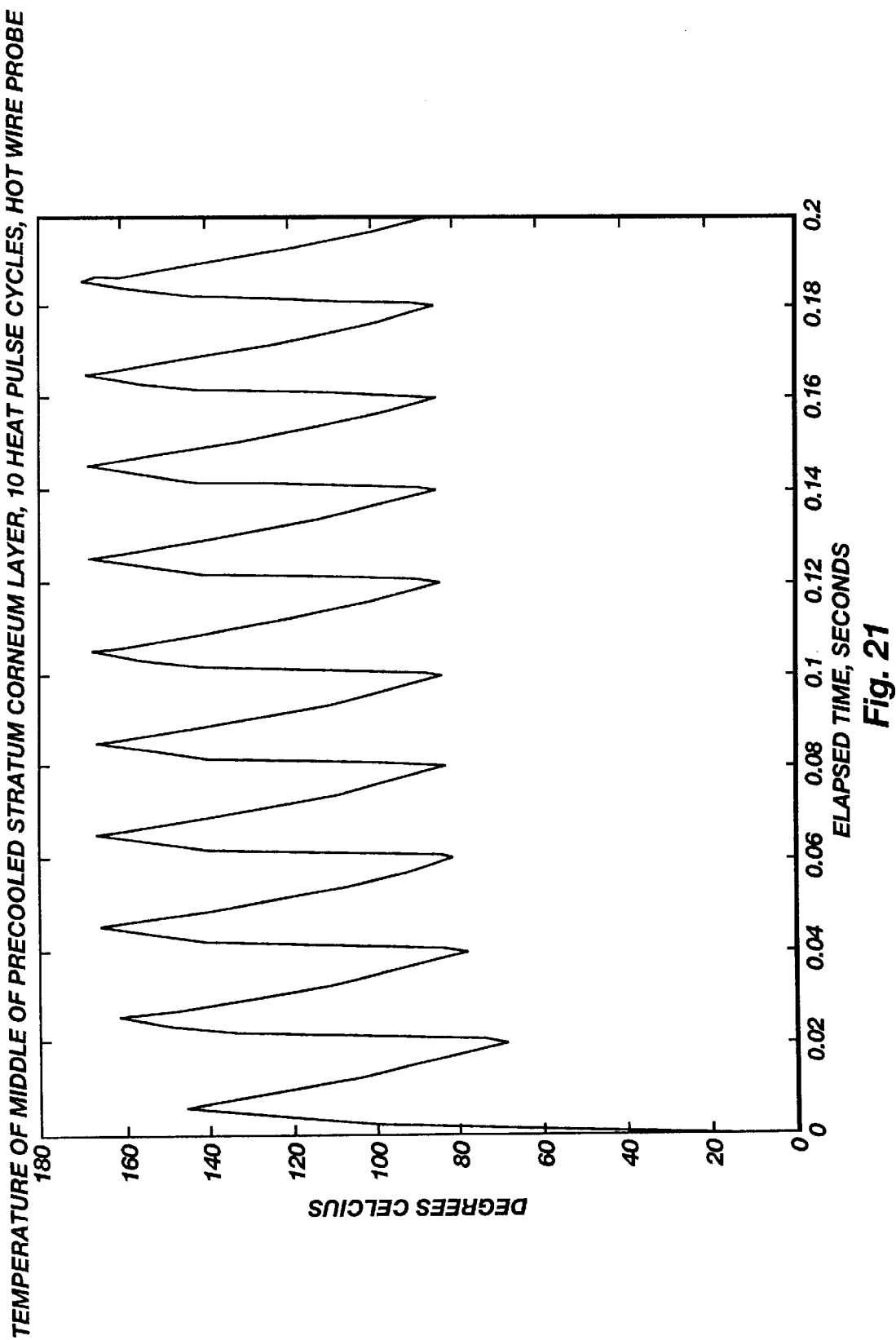
Figure 22:
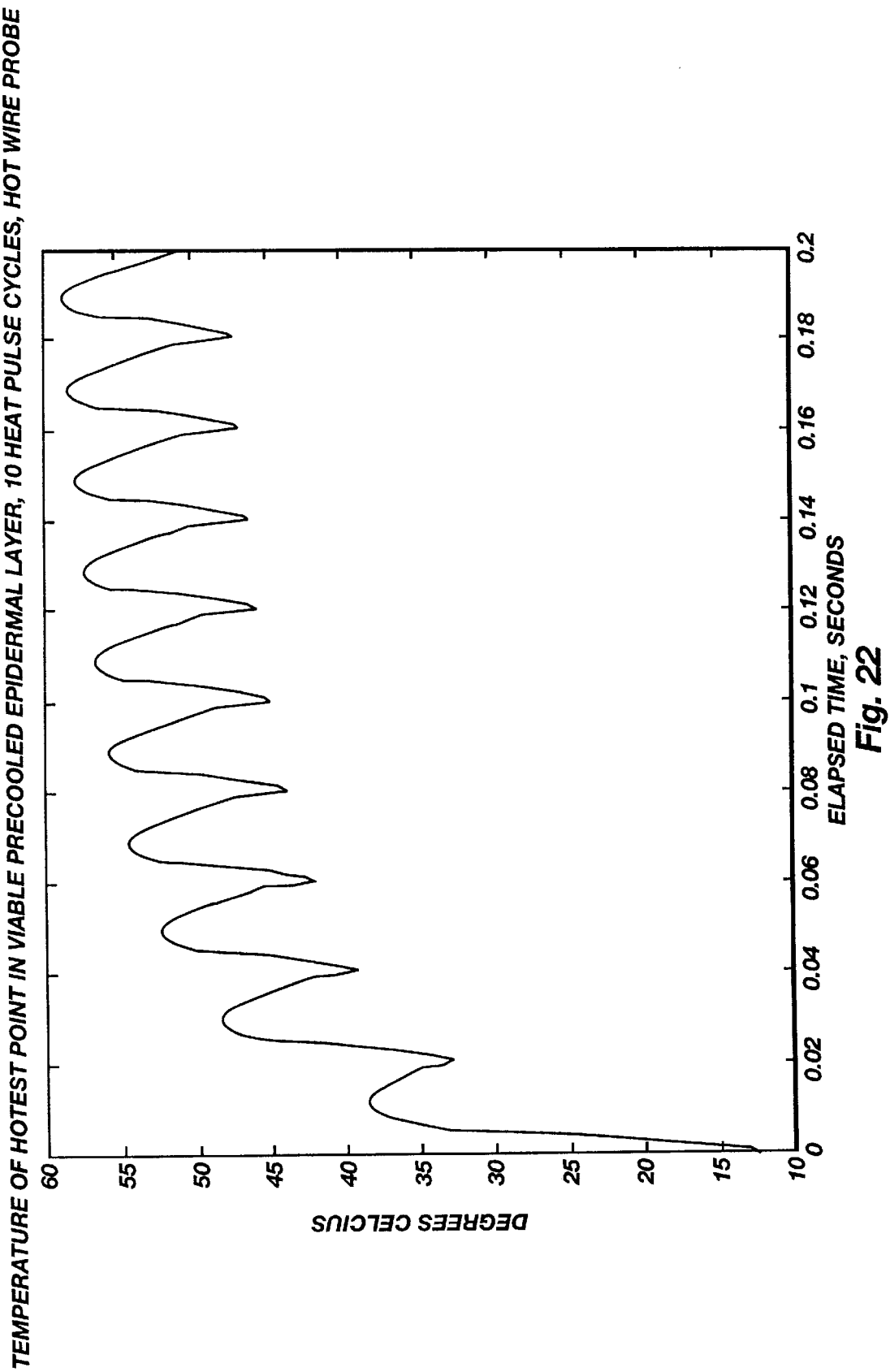

In this example, the procedure of Example 11 was followed except that the skin was pre-cooled according to the procedure of Example 10. Similarly, pre-cooling the target site yields similarly positive results with the "hot-wire" embodiment. The results of the pre-cooled simulation of the "hot-wire" approach are shown in FIGS. 20–22.

EXAMPLE 13

Figure 23:
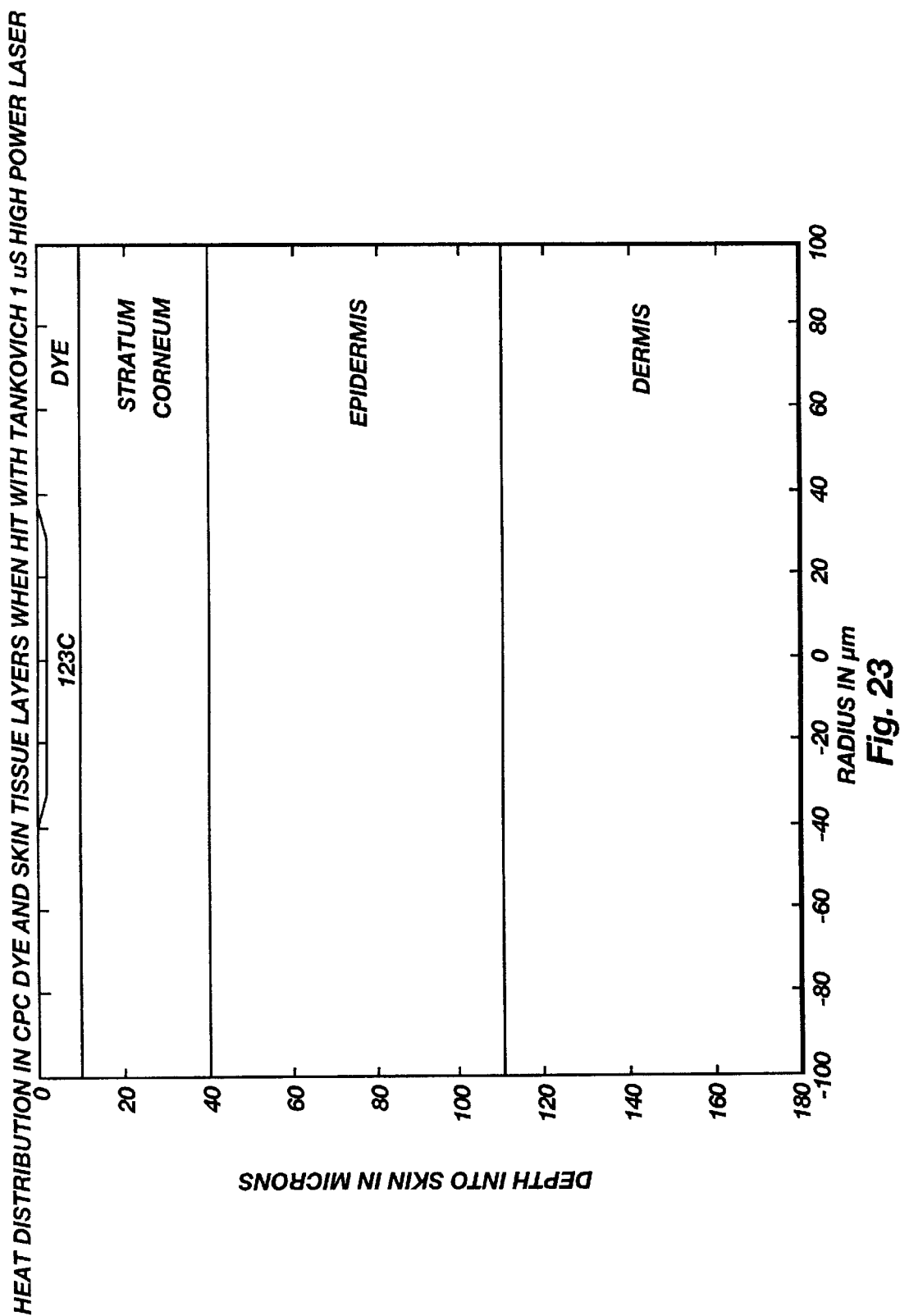
FIGS. 23 and 24 show graphic representations of temperature distribution and temperature as a function of time in the stratum corneum, respectively, during simulated thermal poration events wherein the tissue is heated optically according to the operating parameters of Tankovich '803.
Figure 24:
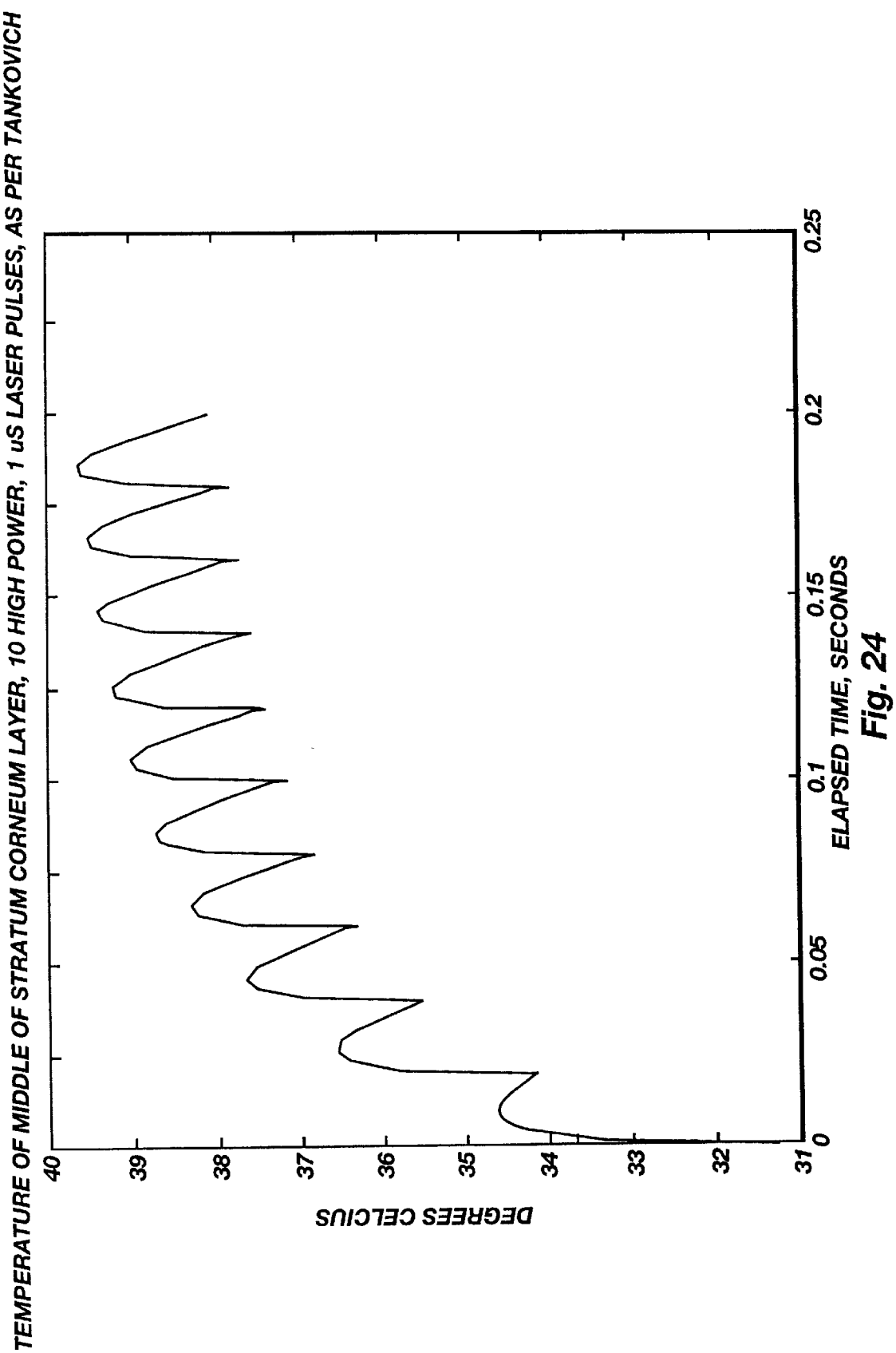

As discussed in the background introduction of this disclosure, the Tankovich '803 patent appears at first glance to be similar to the presently claimed invention. In this example, the simulation model was set up with the operating parameters specified in Tankovich '803, i.e. a pulse width of 1 $\mu$s and a power level of 40,000,000 W/cm$^2$. FIGS. 23 and 24 show that under these conditions no portion of the stratum corneum reaches the threshold for flash vaporization of water, 123° C., and thus no ablation/microporation of the stratum corneum occurs. In practice, applying this type of high peak power, short duration pulse to the topical dye layer merely vaporizes the dye off of the surface of the skin with no effect on the skin. This example, thus, demonstrates that the conditions specified by Tankovich '803 are inoperative in the presently claimed invention.

EXAMPLE 14

In this example, interstitial fluid obtained after porating the skin according to the procedure of Example 6 was collected and analyzed to determine the glucose concentration thereof. Data were obtained on four non-diabetic subjects and six type I diabetic subjects undergoing a glucose load test. Subject's ages ranged from 27 to 43. The goal of the study was to examine the utility of the method for painlessly harvesting enough interstitial fluid (ISF) from the subjects to allow the ISF samples to be assayed for glucose content, and then compare these concentrations to the glucose level presenting in the subject's whole blood.

All subjects had both the blood and ISF glucose assays performed with the "ELITE" system from Miles-Bayer. All ten subjects underwent identical measurement protocols, with adjustments being made regarding the glucose load and insulin shot for those subjects with insulin dependent diabetes.

The basic design of the study was to recruit a modest number of volunteers, some with diabetes and some without diabetes, from which a series of sample pairs of ISF and whole blood were drawn every 3 to 5 minutes throughout the 3 to 4 hour duration of the study period. Both the blood and the ISF samples were assayed for glucose and the statistical relationship between the blood glucose levels and the interstitial fluid determined. To examine the hypothesized temporal lag of the ISF glucose levels as compared to the whole blood glucose levels, the study subjects were induced to exhibit a significant and dynamic change in their glucose levels. This was accomplished by having each subject fast for 12 hours prior to beginning the test and then giving the subject a glucose load after his or her baseline glucose levels have been established via a set of three fasting blood and ISF glucose levels. After the baseline levels had been established, the subjects were given a glucose load in the form of sweet juice based on the following guidelines:

i. For the control subjects, the glucose load was calculated based on a 0.75 gram glucose per pound of body weight.

ii. For the subjects with insulin dependent diabetes the glucose load was 50 grams of glucose. In addition, immediately after taking the glucose load the diabetic subjects will self inject their normal morning dose of fast acting insulin. In the case where the diabetic subject presents with fasting glucose levels above 300 mg/dL, they were asked to give themselves their insulin injection first, and the glucose load was provided after their blood glucose levels have dropped to below 120 mg/dL.

Each subject recruited was first given a complete description of the study in the "Informed Consent" document which they were required to understand and sign before they were officially enrolled into the program. Upon acceptance, they completed a medical history questionnaire. The detailed clinical procedure implemented was:

(a) Subject fasted from 9:00 p.m. the night before the study visit, consuming only water. No caffeine, cigarettes, fruit juice were allowed during this period.

(b) Subject arrived at the testing facility by 9:00 a.m. the next day.

(c) Subject was seated in a reclining chair provided for the subject to relax in throughout the study procedure.

(d) Both whole blood and ISF samples were taken at three to five minute intervals beginning upon the subject's arrival and continuing for the next three to four hours. The duration over which the data were collected was based on when the subject's blood glucose levels had returned to the normal range and stabilized after the glucose load. The ISF samples were harvested using the optical poration, ISF pumping method, described in more detail below. Each ISF sample was roughly 5 $\mu$L by volume to ensure a good fill of the ELITE test strip. The blood samples were obtained via a conventional finger prick lancet. Both the ISF and the blood samples were immediately assayed for glucose with the ELITE home glucometer system from Miles-Bayer. To improve the estimate of the 'true' blood glucose levels, two separate ELITE assays were be done on each finger stick sample.

(e) To facilitate the continued collection of the ISF from the same site throughout the entire data collection phase for a given individual, a 5 by 5 matrix of twenty five micropores was created on the subject's upper forearm, each micropore being between 50 and 80 $\mu$m across and spaced 300 $\mu$m apart. A 30 mm diameter teflon disk with a 6 mm hole in the center was attached to the subject's forearm with a pressure sensitive adhesive and positioned such that the 6 mm center hole was located over the 5 by 5 matrix of micro-pores. This attachment allowed a convenient method by which a small suction hose could be connected, applying a mild vacuum (10 to 12 inches of Hg) to the porated area to induce the ISF to flow out of the body through the micropores. The top of the teflon disk was fitted with a clear glass window allowing the operator to directly view the micro-porated skin beneath it. When a 5 $\mu$L bead of ISF was formed on the surface of the skin, it could easily be ascertained by visually monitoring the site through this window. This level of vacuum created a nominal pressure gradient of around 5 pounds/square inch (PSI). Without the micropores, no ISF whatsoever could be drawn from the subject's body using only the mild vacuum.

(f) After the first three sample pairs have been drawn, the subject was given a glucose load in the form of highly sweetened orange juice. The amount of glucose given was 0.75 grams per pound of body weight for the nondiabetic subjects and 50 grams for the diabetic subjects. The diabetic subjects also self administered a shot of fast acting insulin, (regular) with the dosage appropriately calculated, based on this 50 gram level of glucose concurrent with the ingestion of the glucose load. With the normal 1.5 to 2.5 hour lag between receiving an insulin shot and the maximum effect of the shot, the diabetic subjects were expected to exhibit an upwards excursion of their blood glucose levels ranging up to 300 mg/dL and then dropping rapidly back into the normal range as the insulin takes effect. The nondiabetic subjects were expected to exhibit the standard glucose tolerance test profiles, typically showing a peak in blood glucose levels between 150 mg/dL and 220 mg/dL from 45 minutes to 90 minutes after administering the glucose load, and then a rapid drop back to their normal baseline levels over the next hour or so.

(g) Following the administration of the glucose load or glucose load and insulin shot, the subjects had samples drawn, simultaneously, of ISF and finger prick whole blood at five minute intervals for the next three to four hours. The sampling was terminated when the blood glucose levels in three successive samples indicate that the subject's glucose had stabilized.

Upon examination of the data, several features were apparent. In particular, for any specific batch of ELITE test strips, there exist a distinct shift in the output shown on the glucometer in mg/dL glucose as compared to the level indicated on the blood. An elevated reading would be expected due to the lack of hematocrit in the ISF and to the normal differences in the electrolyte concentrations between the ISF and whole blood. Regardless of the underlying reasons for this shift in output, it was determined via comparison to a reference assay that the true ISF glucose levels are linearly related to the values produced by the ELITE system, with the scaling coefficients constant for any specific batch of ELITE strips. Consequently, for the comparison of the ISF glucose levels versus the whole blood measurements, first order linear correction was applied to the ISF data as follows:

$$ISF_{glucose} = 0.606 * ISF_{ELITE} + 19.5.$$

This scaling of the output of the ELITE glucometer when used to measure ISF glucose levels, allows one to examine, over the entire data set, the error terms associated with using ISF to estimate blood glucose levels. Of course, even with no linear scaling whatsoever, the correlations between the ISF glucose values and the blood glucose levels are the same as the scaled version.

Based on the majority of the published body of literature on the subject of ISF glucose as well as preliminary data, it was originally expected that a 15 to 20 minute lag between the ISF glucose levels and the those presented in the whole blood from a finger stick would be observed. This is not what the data showed when analyzed. Specifically, when each individual's data set is analyzed to determine the time shift required to achieve the maximum correlation between the ISF glucose levels and the blood glucose levels it was discovered that the worst case time lag for this set of subjects was only 13 minutes and the average time lag was only 6.2 minutes, with several subjects showing a temporal tracking that was almost instantaneous (about 1 minute).

Figure 25:
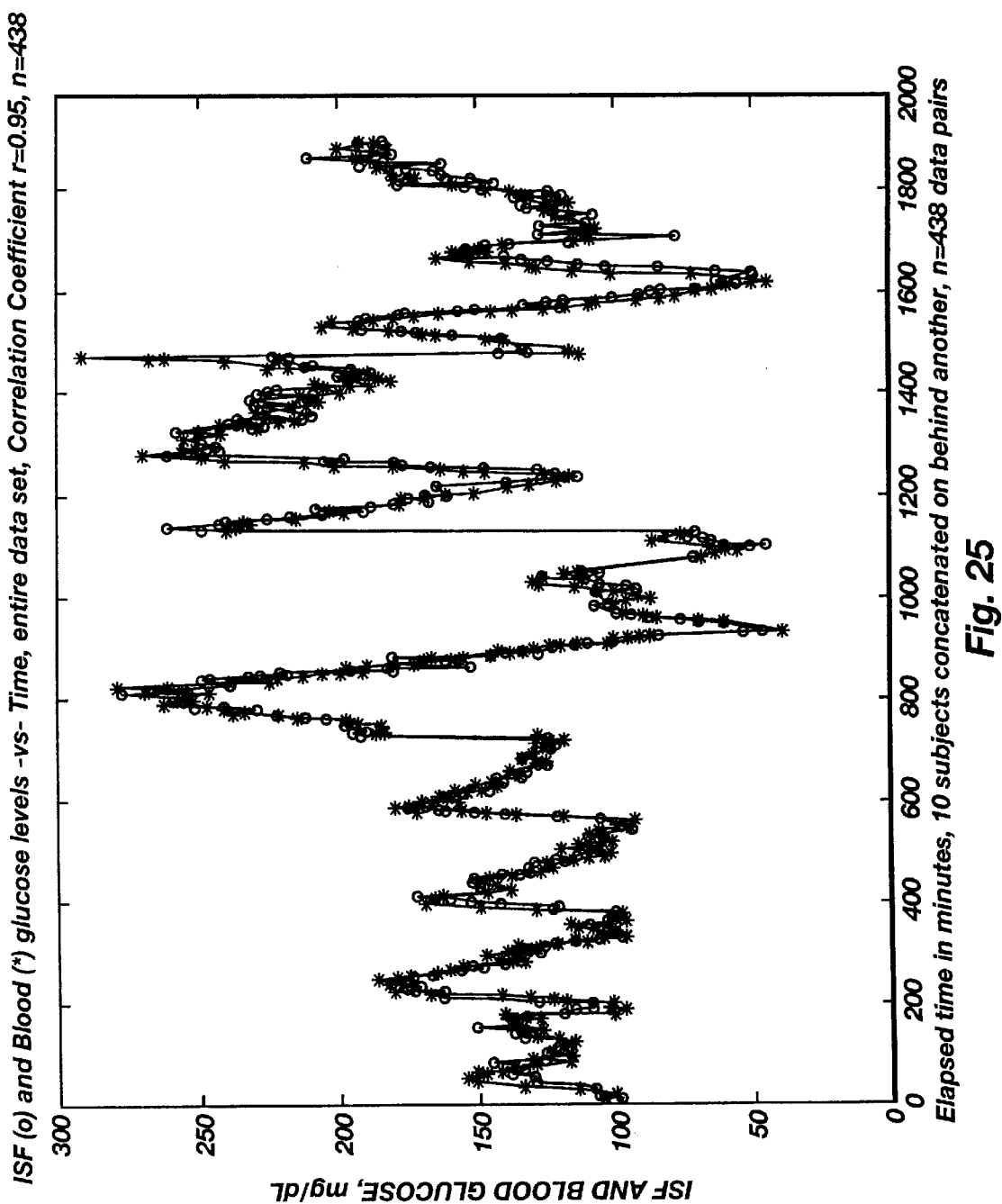
FIG. 25 shows a graphic representation of interstitial fluid (ISF; ○) and blood (*) glucose levels as a function of time.

Based on the minimal amount of lag observed in this data set, the graph shown in FIG. 25 presents all ten of the glucose load tests, concatenated one after another on an extended time scale. The data are presented with no time shifting whatsoever, showing the high level of tracking between the ISF and blood glucose levels the entire clinical data set being dealt with in exactly the same manner. If the entire data set is shifted as a whole to find the best temporal tracking estimate, the correlation between the ISF and blood glucose levels peaks with a delay of two (2) minutes at an r value of r=0.97. This is only a trivial improvement from the unshifted correlation of r=0.964. Therefore, for the remainder of the analysis the ISF values are treated with no time shift imposed on them. That is, each set of blood and ISF glucose levels is dealt with as simultaneously collected data pairs.

After the unshifted Elite ISF readings had been scaled to reflect the proportional glucose present in the ISF, it was possible to examine the error associated with these data. The simplest method for this is to assume that the average of the two ELITE finger-stick blood glucose readings is in fact the absolutely correct value, and then to merely compare the scaled ISF values to these mean blood glucose values. These data are as follows: Standard Deviation Blood-ISF, 13.4 mg/dL; Coefficient of Variance of ISF, 9.7%; Standard Deviation of the Two Elites, 8.3 mg/dL; and Coefficient of Variance of Blood (Miles), 6%.

As these data show, the blood based measurement already contains an error term. Indeed, the manufacturer's published performance data indicates that the ELITE system has a nominal Coefficient of Variance (CV) of between 5% and 7%, depending on the glucose levels and the amount of hematocrit in the blood.

Figure 26:
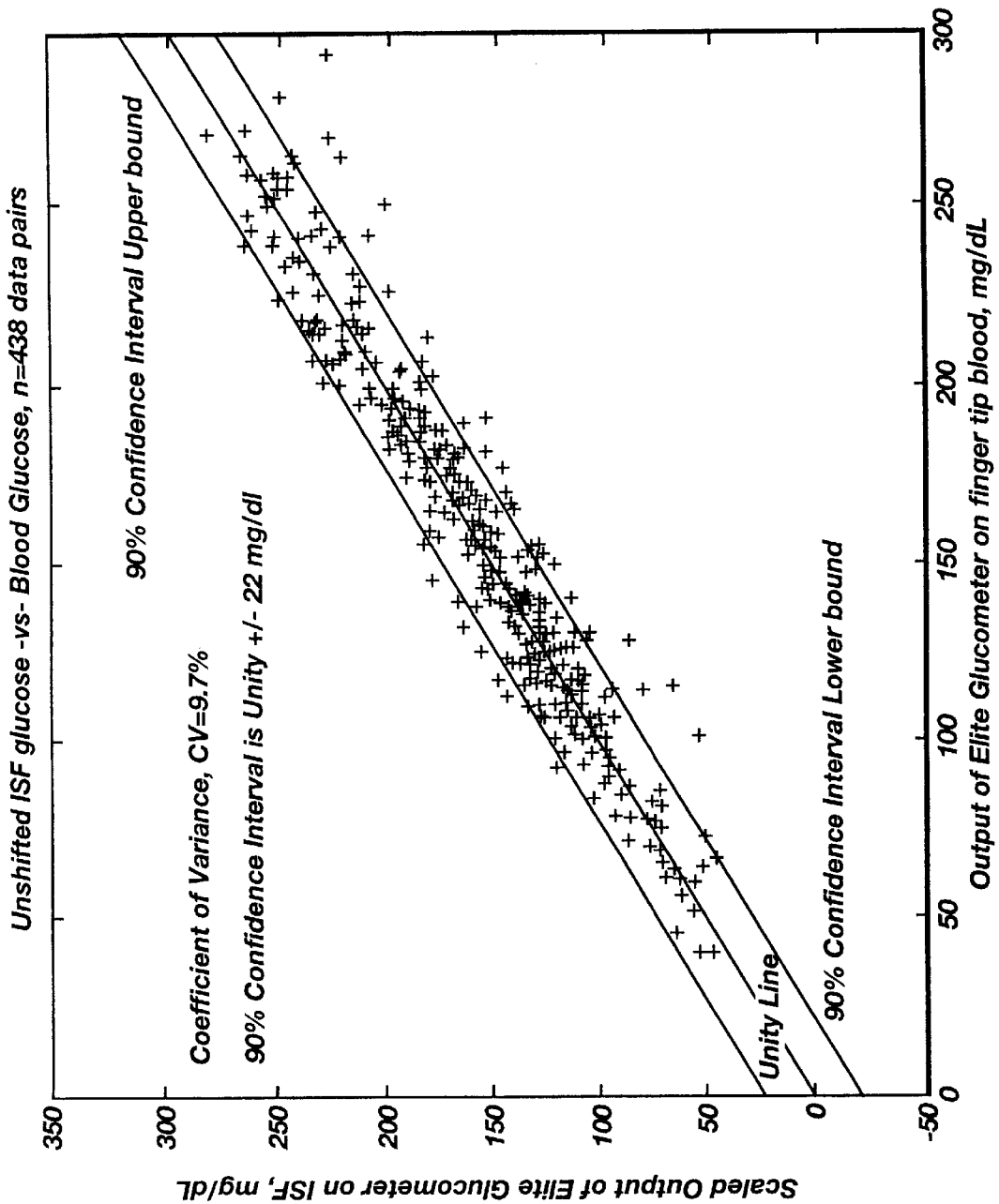
FIG. 26 shows a scatter plot representation of the difference term between the ISF glucose and the blood glucose data of FIG. 25.

An additional look at the difference term between the ISF glucose and the blood glucose is shown in the form of a scatter plot in FIG. 26. In this figure, the upper and lower bounds of the 90% confidence interval are also displayed for reference. It is interesting to note that with only two exceptions, all of the data in the range of blood glucose levels below 100 mg/dL fall within these 90% confidence interval error bars. This is important as the consequences of missing a trend towards hypoglycemia would be very significant to the diabetic user. That is, it would be much better to under-predict glucose levels in the 40 to 120 mg/dL than to over predict them.

Essentially, if one assumes that the basic assay error when the ELITE system is used on ISF is comparable to the assay error associated with the ELITE's use on whole blood, then the Deviation of the ISF glucose from the blood glucose can be described as:

$$ISF_{deviation} = [(ISF_{actual})^2 + (ISF_{actual})^2]^{1/2}.$$

Applying this equation to the values shown above, one can solve for the estimated 'true' value of the ISF error term:

$$ISF_{actual} = [(ISF_{deviation})^2 - (Blood_{actual})^2]^{1/2}.$$

Or, solving the equation, $$ISF_{actual} = [(13.4)^2 - (8.3)^2]^{1/2} = 10.5 \text{ mg/dl}.$$

Figure 27:
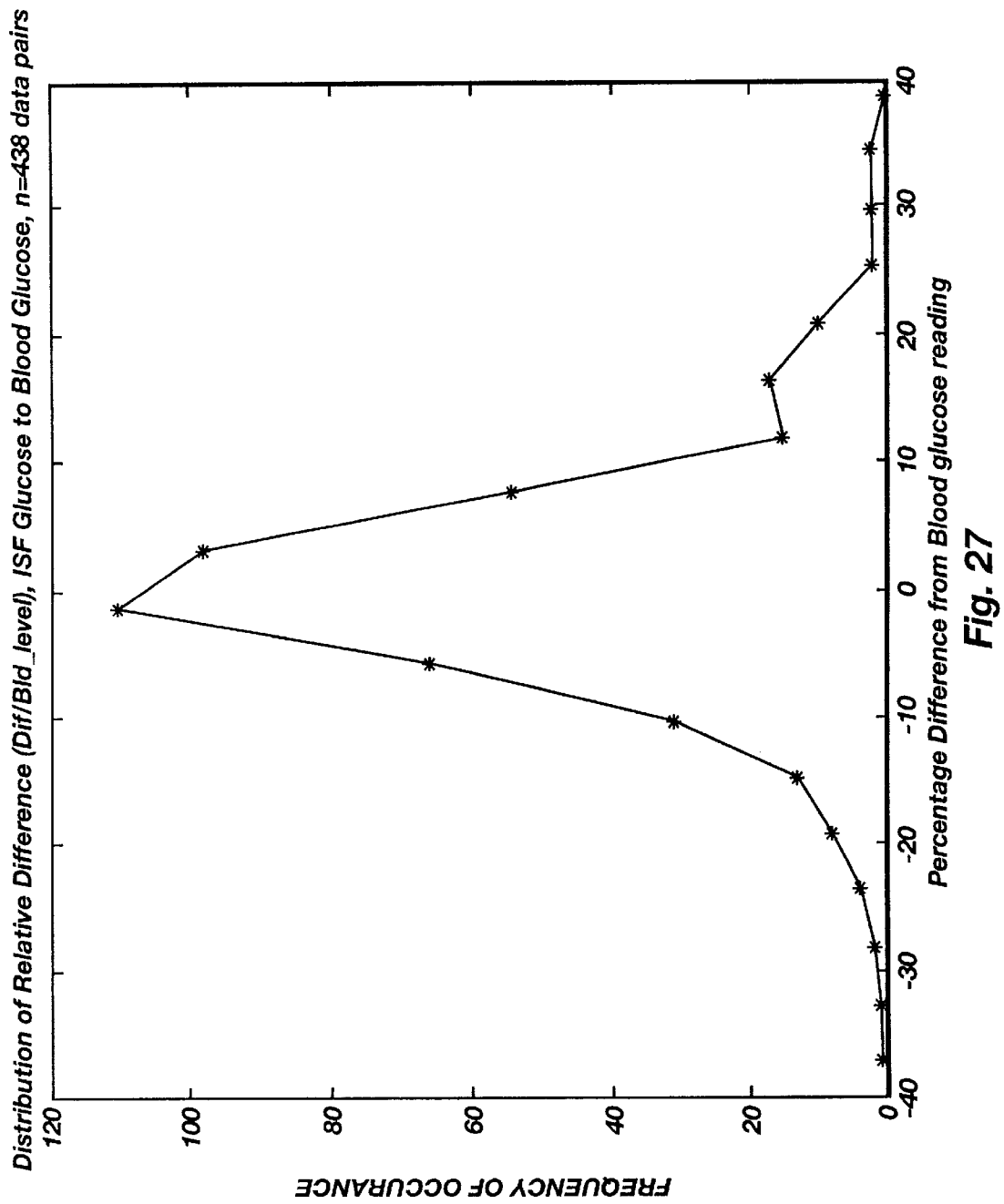
FIG. 27 shows a histogram of the relative deviation of the ISF to the blood glucose levels from FIG. 25.

A histogram of the relative deviation of the ISF to the blood glucose levels is shown in FIG. 27.

Drug Delivery through Pores in the Stratum Corneum

The present invention also includes a method for the delivery of drugs, including drugs currently delivered transdermally, through micro-pores in the stratum corneum. In one illustrative embodiment, the delivery is achieved by placing the solution in a reservoir over the poration site. In another illustrative embodiment, a pressure gradient is used to further enhance the delivery. In still another illustrative embodiment, sonic energy is used with or without a pressure gradient to further enhance the delivery. The sonic energy can be operated according to traditional transdermal parameters or by utilizing acoustic streaming effects, which will be described momentarily, to push the delivery solution through the porated stratum corneum.

EXAMPLE 15

Figure 28:
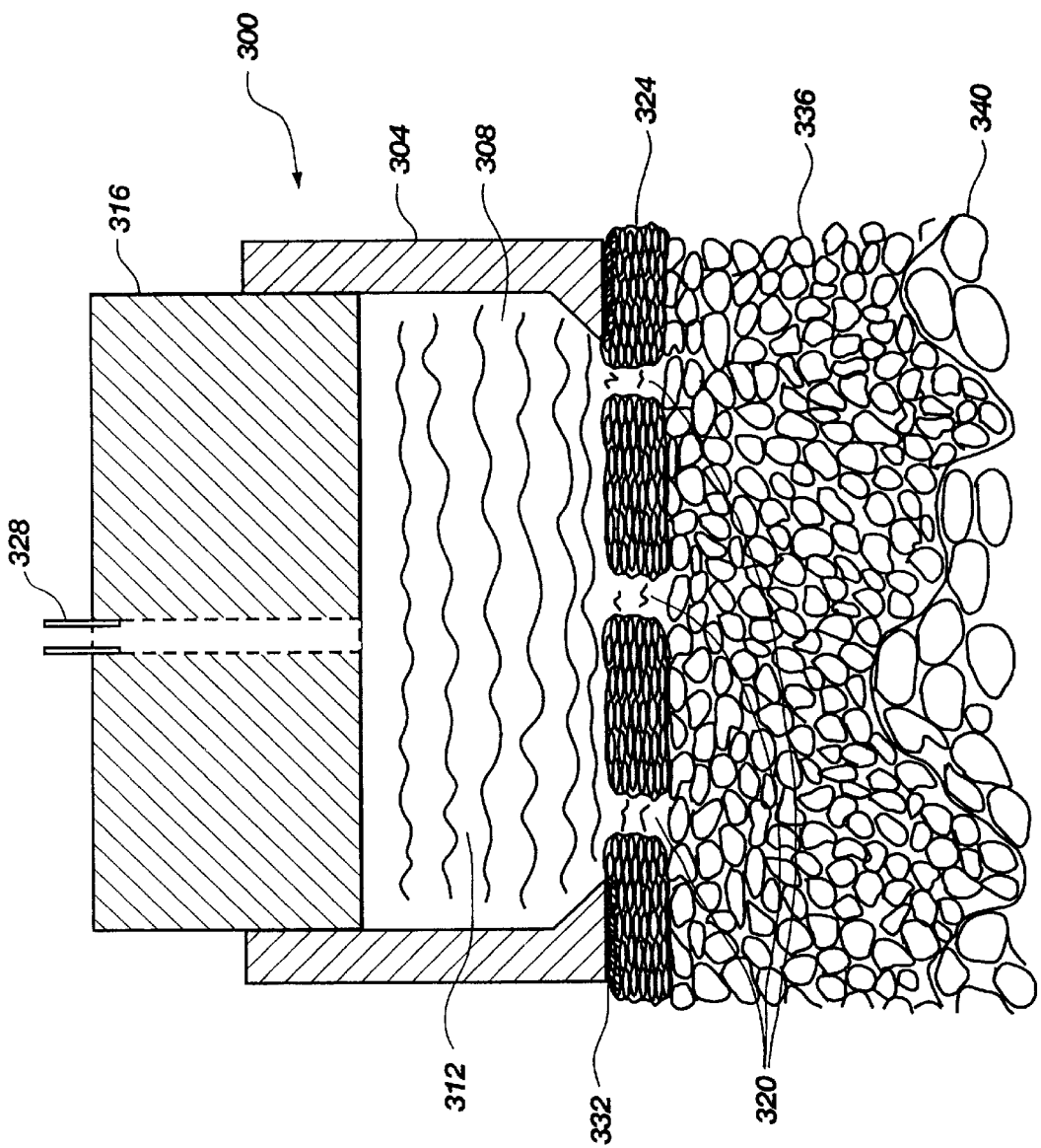
FIG. 28 shows a cross section of an illustrative delivery apparatus for delivering a drug to a selected area on an individual's skin.

This example shows the use of stratum corneum poration for the delivery of lidocaine, a topical analgesic. The lidocaine solution also contained a chemical permeation enhancer formulation designed to enhance its passive diffusion across the stratum corneum. A drawing of an illustrative delivery apparatus 300 is shown in FIG. 28, wherein the apparatus comprises a housing 304 enclosing a reservoir 308 for holding a drug-containing solution 312. The top portion of the housing comprises an ultrasonic transducer 316 for providing sonic energy to aid in transporting the drug-containing solution through micropores 320 in the stratum corneum 324. A port 328 in the ultrasonic transducer permits application of pressure thereto for further aiding in transporting the drug-containing solution through the micropores in the stratum corneum. The delivery apparatus is applied to a selected area of an individual's skin such that it is positioned over at least one, and preferably a plurality, of micropores. An adhesive layer 332 attached to a lower portion of the housing permits the apparatus to adhere to the skin such that the drug-containing solution in the reservoir is in liquid communication with the micropores. Delivery of the drug through the micropores results in transport into the underlying epidermis 336 and dermis 340.

Five subjects were tested for the effectiveness of drug delivery using poration together with ultrasound. The experiment used two sites on the subjects left forearm about three inches apart, equally spaced between the thumb and upper arm. The site near the thumb will be referred to as site the site furthest from the thumb will be referred to as site 2. Site 1 was used as a control where the lidocaine and enhancer solution was applied using an identical delivery apparatus 300, but without any micro-poration of the stratum corneum or sonic energy. Site 2 was porated with 24 holes spaced 0.8 millimeters apart in a grid contained within a 1 cm diameter circle. The micropores in Site 2 were generated according to the procedure of Example 6. Lidocaine and low level ultrasound were applied. Ultrasound applications were made with a custom manufactured Zevex ultrasonic transducer assembly set in burst mode with 0.4 Volts peak to peak input with 1000 count bursts occurring at 10 Hz with a 65.4 kHz fundamental frequency, i.e., a pulse modulated signal with the transducer energized for 15 millisecond bursts, and then turned off for the next 85 milliseconds. The measured output of the amplifier to the transducer was 0.090 watts RMS.

After application of the lidocaine, sensation measurements were made by rubbing a 30 gauge wire across the test site. Experiments were executed on both sites, Site 1 for 10 to 12 minute duration and Site 2 for two 5 minute duration intervals applied serially to the same site. Both sites were assessed for numbness using a scale of 10 to 0, where 10 indicated no numbness and 0 indicated complete numbness as reported by the test subjects. The following summary of results is for all 5 subjects.

Figure 29A:
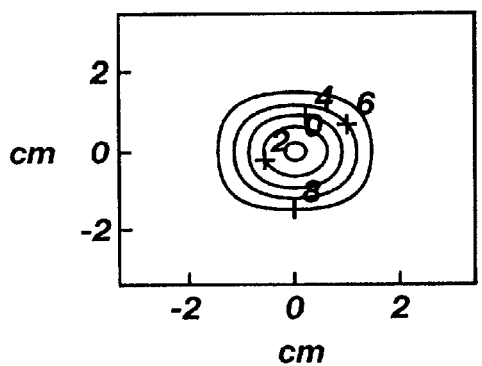
FIGS. 29A–C show graphic representations of areas of skin affected by delivery of lidocaine to selected areas where the stratum corneum is porated (FIGS. 29A–B) or not porated (FIG. 29C).
Figure 29B:
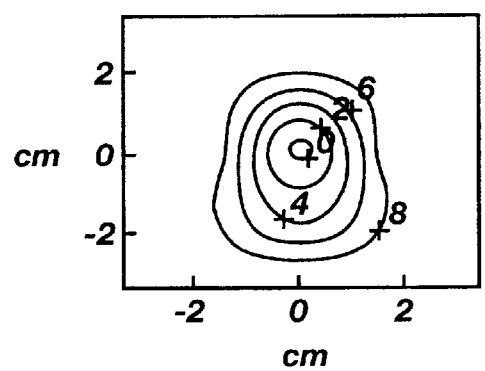
Figure 29C:
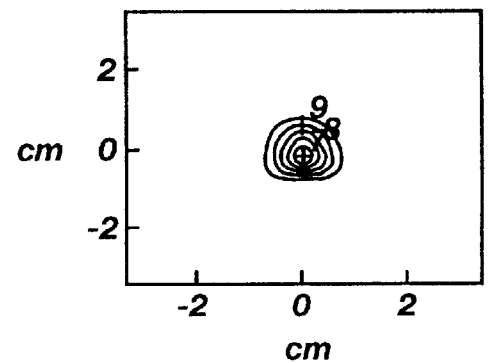

The control site, site 1, presented little to no numbness (scale 7 to 10) at 10 to 12 minutes. At approximately 20 minutes some numbness (scale 3) was observed at site 1 as the solution completely permeated the stratum corneum. Site 1 was cleaned at the completion of the lidocaine application. Site 2 presented nearly complete numbness (scale 0 to 1) in the 1 cm circle containing the porations. Outside the 1 cm diameter circle the numbness fell off almost linearly to 1 at a 2.5 cm diameter circle with no numbness outside the 2.5 cm diameter circle. Assessment of site 2 after the second application resulted in a slightly larger totally numb circle of about 1.2 cm diameter with numbness falling off linearly to 1 in an irregular oval pattern with a diameter of 2 to 2.5 cm perpendicular to the forearm and a diameter of 2 to 6 cm parallel to the forearm. Outside the area no numbness was noted. A graphic representation of illustrative results obtained on a typical subject is shown in FIGS. 29A–C. FIGS. 29A and 29B show the results obtained at Site 2 (porated) after 5 and 10 minutes, respectively. FIG. 29C shows the results obtained at Site 1 (control with no poration).

Sonic Energy and Enhancers for Enhancing Transdermal Flux

The physics of sonic energy fields created by sonic transducers can be utilized in a method by which sonic frequency can be modulated to improve on flux rates achieved by other methods. As shown in FIG. 1 of U.S. Pat. No. 5,445,611, hereby incorporated herein by reference, the energy distribution of an sonic transducer can be divided into near and far fields. The near field, characterized by length N, is the zone from the first energy minimum to the last energy maximum. The zone distal to the last maximum is the far field. The near (N) field pattern is dominated by a large number of closely spaced local pressure peaks and nulls. The length of the near field zone, N, is a function of the frequency, size, and shape of the transducer face, and the speed of sound in the medium through which the ultrasound travels. For a single transducer, intensity variations within its normal operating range do not affect the nature of the sonic energy distribution other than in a linear fashion. However, for a system with multiple transducers, all being modulated in both frequency and amplitude, the relative intensities of separate transducers do affect the energy distribution in the sonic medium, regardless of whether it is skin or another medium.

By changing the frequency of the sonic energy by a modest amount, for example in the range of about 1 to 20%, the pattern of peaks and nulls remains relatively constant, but the length N of the near field zone changes in direct proportion to the frequency. Major changes the frequency, say a factor of 2 or more, will most likely produce a different set of resonances or vibrational modes in the transducer, causing a significantly and unpredictably different near field energy pattern. Thus, with a modest change in the sonic frequency, the complex pattern of peaks and nulls is compressed or expanded in an accordion-like manner. By selecting the direction of frequency modulation, the direction of shift of these local pressure peaks can be controlled. By applying sonic energy at the surface of the skin, selective modulation of the sonic frequency controls movement of these local pressure peaks through the skin either toward the interior of the body or toward the surface of the body. A frequency modulation from high to low drives the pressure peaks into the body, whereas a frequency modulation from low to high pulls the pressure peaks from within the body toward the surface and through the skin to the outside of the body.

Assuming typical parameters for this application of, for example, a 1.27 cm diameter sonic transducer and a nominal operating frequency of 10 MHz and an acoustic impedance similar to that of water, a frequency modulation of 1 MHz produces a movement of about 2.5 mm of the peaks and nulls of the near field energy pattern in the vicinity of the stratum corneum. From the perspective of transdermal and/or transmucosal withdrawal of analytes, this degree of action provides access to the area well below the stratum corneum and even the epidermis, dermis, and other tissues beneath it. For any given transducer, there may be an optimal range of frequencies within which this frequency modulation is most effective.

The flux of a drug or analyte across the skin can also be increased by changing either the resistance (the diffusion coefficient) or the driving force (the gradient for diffusion). Flux can be enhanced by the use of so-called penetration or chemical enhancers.

Chemical enhancers are comprised of two primary categories of components, i.e., cell-envelope disordering compounds and solvents or binary systems containing both cell-envelope disordering compounds and solvents.

Cell envelope disordering compounds are known in the art as being useful in topical pharmaceutical preparations and function also in analyte withdrawal through the skin. These compounds are thought to assist in skin penetration by disordering the lipid structure of the stratum corneum cell-envelopes. A comprehensive list of these compounds is described in European Patent Application 43,738, published Jun. 13, 1982, which is incorporated herein by reference. It is believed that any cell envelope disordering compound is useful for purposes of this invention.

Suitable solvents include water; diols, such as propylene glycol and glycerol; monoalcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones(azones) and the like.

U.S. Pat. No. 4,537,776, Cooper, issued Aug. 27, 1985, contains an excellent summary of prior art and background information detailing the use of certain binary systems for permeant enhancement. Because of the completeness of that disclosure, the information and terminology utilized therein are incorporated herein by reference.

Similarly, European Patent Application 43,738, referred to above, teaches using selected diols as solvents along with a broad category of cell-envelope disordering compounds for delivery of lipophilic pharmacologically-active compounds. Because of the detail in disclosing the cell-envelope disordering compounds and the diols, this disclosure of European Patent Application 43,738 is also incorporated herein by reference.

A binary system for enhancing metoclopramide penetration is disclosed in UK Patent Application GB 2,153,223 A, published Aug. 21, 1985, and consists of a monovalent alcohol ester of a C8-32 aliphatic monocarboxylic acid (unsaturated and/or branched if C18-32) or a C6-24 aliphatic monoalcoliol (unsaturated and/or branched if C14-24) and an N-cyclic compound such as 2-pyrrolidone, N-methylpyrrolidone and the like.

Combinations of enhancers consisting of diethylene glycol monoethyl or monomethyl ether with propylene glycol monolaurate and methyl laurate are disclosed in U.S. Pat. No. 4,973,468 as enhancing the transdermal delivery of steroids such as progestogens and estrogens. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of $C_2$ to $C_4$ alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a $C_2$ or $C_3$ alkanol and an inert diluent such as water.

Other chemical enhancers, not necessarily associated with binary systems include DMSO or aqueous solutions of DMSO such as taught in Herschler, U.S. Pat. No. 3,551,554; Herschler, U.S. Pat. No. 3,711,602; and Herschler, U.S. Pat. No. 3,711,606, and the azones (n-substituted-alkyl-azacycloalkyl-2-ones) such as noted in Cooper, U.S. Pat. No. 4,557,943.

Some chemical enhancer systems may possess negative side effects such as toxicity and skin irritation. U.S. Pat. No. 4,855,298 discloses compositions for reducing skin irritation caused by chemical enhancer containing compositions having skin irritation properties with an amount of glycerin sufficient to provide an anti-irritating effect.

Because the combination of microporation of the stratum corneum and the application of sonic energy accompanied by the use of chemical enhancers can result in an improved rate of analyte withdrawal or permeant delivery through the stratum corneum, the specific carrier vehicle and particularly the chemical enhancer utilized can be selected from a long list of prior art vehicles some of which are mentioned above and incorporated herein by reference. To specifically detail or enumerate that which is readily available in the art is not thought necessary. The invention is not drawn to the use of chemical enhancers per se and it is believed that all chemical enhancers, useful in the delivery of drugs through the skin, will function with dyes in optical microporation and also with sonic energy in effecting measurable withdrawal of analytes from beneath and through the skin surface or the delivery of permeants or drugs through the skin surface.

EXAMPLE 16

Modulated sonic energy and chemical enhancers were tested for their ability to control transdermal flux on human cadaver skin samples. In these tests, the epidermal membrane had been separated from the human cadaver whole skin by the heat-separation method of Example 1. The epidermal membrane was cut and placed between two halves of the permeation cell with the stratum corneum facing either the upper (donor) compartment or lower (receiver) compartment. Modified Franz cells were used to hold the epidermis, as shown in FIG. 2 of U.S. Pat. No. 5,445,611. Each Franz cell consists of an upper chamber and a lower chamber held together with one or more clamps. The lower chamber has a sampling port through which materials can be added or removed. A sample of stratum corneum is held between the upper and lower chambers when they are clamped together. The upper chamber of each Franz cell is modified to allow an ultrasound transducer to be positioned within 1 cm of the stratum corneum membrane. Methylene blue solution was used as an indicator molecule to assess the permeation of the stratum corneum. A visual record of the process and results of each experiment was obtained in a time stamped magnetic tape format with a video camera and video cassette recorder (not shown). Additionally, samples were withdrawn for measurement with an absorption spectrometer to quantitate the amount of dye which had traversed the stratum corneum membrane during an experiment. Chemical enhancers suitable for use could vary over a wide range of solvents and/or cell envelope disordering compounds as noted above. The specific enhancer utilized was: ethanol/glycerol/water/glycerolmonooleate/methyl laurate in 50/30/15/2.5/2.5 volume ratios. The system for producing and controlling the sonic energy included a programmable 0–30 MHz arbitrary waveform generator (Stanford Research Systems Model DS345), a 20 watt 0–30 MHz amplifier, and two unfocused ultrasound immersion transducers having peak resonances at 15 and 25 MHz, respectively. Six cells were prepared simultaneously for testing of stratum corneum samples from the same donor. Once the stratum corneum samples were installed, they were allowed to hydrate with distilled water for at least 6 hours before any tests were done.

EXAMPLE 17

Effects of Sonic Energy without Chemical Enhancers

As stated above in Example 16, the heat-separated epidermis was placed in the Franz cells with the epidermal side facing up, and the stratum corneum side facing down, unless noted otherwise. The lower chambers were filled with distilled water, whereas the upper chambers were filled with concentrated methylene blue solution in distilled water.

Heat Separated Epidermis

Immediately after filling the upper chambers with methylene blue solution, sonic energy was applied to one of the cells with the transducer fully immersed. This orientation would correspond, for example, to having the transducer on the opposite side of a fold of skin, or causing the sonic energy to be reflected off a reflector plate similarly positioned and being used to "push" analyte out of the other side of the fold into a collection device. The sonic energy setting was initially set at the nominal operating frequency of 25 MHz with an intensity equivalent to a 20 volt peak-to-peak (P-P) input wave form. This corresponds to roughly a 1 watt of average input power to the transducer and similarly, assuming the manufacturer's nominal value for conversion efficiency of 1% for this particular transducer, a sonic output power of around 0.01 watts over the 0.78 $cm^2$ surface of the active area or a sonic intensity of 0.13 watts/$cm^2$. Three other control cells had no sonic energy applied to them. After 5 minutes the sonic energy was turned off. No visual indication of dye flux across the stratum corneum was observed during this interval in any of the cells, indicating levels less than approximately 0.0015% (v/v) of dye solution in 2 ml of receiver medium.

Testing of these same 3 control cells and 1 experimental cell was continued as follows. The intensity of sonic energy was increased to the maximum possible output available from the driving equipment of a 70 volt peak-to-peak input 12 watts average power input or ($\approx$0.13 watts/$cm^2$) of sonic output intensity. Also, the frequency was set to modulate or sweep from 30 MHz to 10 MHz. This 20 MHz sweep was performed ten times per second, i.e., a sweep rate of 10 Hz. At these input power levels, it was necessary to monitor the sonic energy transducer to avoid overheating. A contact thermocouple was applied to the body of the transducer and power was cycled on and off to maintain maximum temperature of the transducer under 42° C. After about 30 minutes of cycling maximum power at about a 50% duty cycle of 1 minute on and 1 minute off, there was still no visually detectable permeation of the stratum corneum by the methylene blue dye.

A cooling water jacket was then attached to the sonic energy transducer to permit extended excitation at the maximum energy level. Using the same 3 controls and 1 experimental cell, sonic energy was applied at maximum power for 12 hours to the experimental cell. During this time the temperature of the fluid in the upper chamber rose to only 35° C., only slightly above the approximately 31° C. normal temperature of the stratum corneum in vivo. No visual evidence of dye flux through the stratum corneum was apparent in any of (lie four cells after 12 hrs. of sonic energy applied as described above.

EXAMPLE 18

Effects of Sonic Energy without Chemical Enhancers

Perforated Stratum Corneum

Six cells were prepared as described above in Example 16. The clamps holding the upper and lower chambers of the Franz cells were tightened greater than the extent required to normally seal the upper compartment from the lower compartment, and to the extent to artificially introduce perforations and "pinholes" into the heat-separated epidermal samples. When dye solution was added to the upper chamber of each cell, there were immediate visual indications of leakage of dye into the lower chambers through the perforations formed in the stratum corneum. Upon application of sonic energy to cells in which the stratum corneum was so perforated with small "pinholes," a rapid increase in the transport of fluid through a pinhole in the stratum corneum was observed. The rate of transport of the indicator dye molecules was directly related to whether the sonic energy was applied or not. That is, application of the sonic energy caused an immediate (lag time approximately <0.1 second) pulse of the indicator molecules through the pinholes in the stratum corneum. This pulse of indicator molecules ceased immediately upon turning off of the sonic energy (a shutoff lag of approximately <0.1 second). The pulse could be repeated as described.

EXAMPLE 19

Effects of Sonic Energy and Chemical Enhancers

Two different chemical enhancer formulations were used. Chemical Enhancer One or CE1 was an admixture of ethanol/glycerol/water/glycerol monooleate/methyl laurate in a 50/30/15/2.5/2.5 volume ratio. These are components generally regarded as safe, i.e. GRAS, by the FDA for use as pharmaceutical excipients. Chemical Enhancer Two or CE2 is an experimental formulation shown to be very effective in enhancing transdermal drug delivery, but generally considered too irritating for long term transdermal delivery applications. CE2 contained ethanol/glycerol/water/lauradone/methyllaurate in the volume ratios 50/130/15/2.5/2.5. Lauradone is the lauryl (dodecyl) ester of 2-pyrrolidone-5-carboxylic acid ("PCA") and is also referred to as lauryl PCA.

Six Franz cells were set up as before (Example 16) except that the heat separated epidermis was installed with the epidermal layer down, i.e., stratum corneum side facing up. Hydration was established by exposing each sample to distilled water overnight. To begin the experiment, the distilled water in the lower chambers was replaced with methylene blue dye solution in all six cells. The upper chambers were filled with distilled water and the cells were observed for about 30 minutes confirming no passage of dye to ensure that no pinhole perforations were present in any of the cells. When none were found, the distilled water in the upper chambers was removed from four of the cells. The other two cells served as distilled water controls. The upper chambers of two of the experimental cells were then filled with CE1 and the other two experimental cells were filled with CE2.

Sonic energy was immediately applied to one of the two CE2 cells. A 25 MHz transducer was used with the frequency sweeping every 0.1 second from 10 MHz to 30 MHz at maximum intensity of $\approx$0.13 watts/$cm^2$. After 10–15 minutes of sonic energy applied at a 50% duty cycle, dye flux was visually detected. No dye flux was detected in the other five cells.

Sonic energy was then applied to one of the two cells containing CE1 at the same settings. Dye began to appear in the upper chamber within 5 minutes. Thus, sonic energy together with a chemical enhancer significantly increased the transdermal flux rate of a marker dye through the stratum corneum, as well as reduced the lag time.

EXAMPLE 20

Effects of Sonic Energy and Chemical Enhancers

Formulations of the two chemical enhancers, CE1 and CE2, were prepared minus the glycerin and these new formulations, designated CE1MG and CE2MG, were tested as before. Water was substituted for glycerin so that the proportions of the other components remained unchanged. Three cells were prepared in modified Franz cells with the epidermal side of the heat separated epidermis samples facing toward the upper side of the chambers. These samples were then hydrated in distilled water for 8 hours. After the hydration step, the distilled water in the lower chambers was replaced with either CE1MG or CE2MG and the upper chamber was filled with the dye solution. Sonic energy was applied to each of the three cells sequentially.

Upon application of pulsed, frequency-modulated sonic energy for a total duration of less than 10 minutes, a significant increase in permeability of the stratum corneum samples was observed. The permeability of the stratum corneum was altered relatively uniformly across the area exposed to both the chemical enhancer and sonic energy. No "pinhole" perforations through which the dye could traverse the stratum corneum were observed. The transdermal flux rate was instantly controllable by turning the sonic energy on or off. Turning the sonic energy off appeared to instantly reduce the transdermal flux rate such that no dye was visibly being actively transported through the skin sample; presumably the rate was reduced to that of passive diffusion. Turning the sonic energy on again instantly resumed the high level flux rate. The modulated mode appeared to provide a regular pulsatile increase in the transdermal flux rate at the modulated rate. When the sonic energy was set to a constant frequency, the maximum increase in transdermal flux rate for this configuration seemed to occur at around 27 MHz.

Having obtained the same results with all three samples, the cells were then drained of all fluids and flushed with distilled water on both sides of the stratum corneum. The lower chambers were then immediately filled with distilled water and the upper chambers were refilled with dye solution. The cells were observed for 30 minutes. No holes in the stratum corneum samples were observed and no large amount of dye was detected in the lower chambers. A small amount of dye became visible in the lower chambers, probably due to the dye and enhancer trapped in the skin samples from their previous exposures. After an additional 12 hours, the amount of dye detected was still very small.

EXAMPLE 21

Effects of Sonic Energy and Chemical Enhancers Perforated Stratum Corneum

Three cells were prepared with heat-separated epidermis samples with the epidermal side facing toward the upper side of the chamber from the same donor as in Example 16. The samples were hydrated for 8 hours and then the distilled water in the lower chambers was replaced with either CE1MG or CE2MG. The upper chambers were then filled with dye solution. Pinhole perforations in the stratum corneum samples permitted dye to leak through the stratum corneum samples into the underlying enhancer containing chambers. Sonic energy was applied. Immediately upon application of the sonic energy, the dye molecules were rapidly pushed through the pores. As shown above, the rapid flux of the dye through the pores was directly and immediately correlated with the application of the sonic energy.

EXAMPLE 22

Effects of Sonic Energy and Chemical Enhancers

A low cost sonic energy transducer, TDK #NB-58S-01 (TDK Corp.), was tested for its capability to enhance transdermal flux rates. The peak response of this transducer was determined to be about 5.4 MHz with other local peaks occurring at about 7 MHz, 9 MHz, 12.4 MHz, and 16 MHz.

This TDK transducer was then tested at 5.4 MHz for its ability to enhance transdermal flux rate in conjunction with CE1MG. Three cells were set up with the epidermal side facing the lower chamber, then the skin samples were hydrated for 8 hrs. The dye solution was placed in the lower chamber. The transducer was placed in the upper chamber immersed in CE1MG. Using swept frequencies from 5.3 to 5.6 MHz as the sonic energy excitation, significant quantities of dye moved through the stratum corneum and were detected in the collection well of the cell in 5 minutes. Local heating occurred, with the transducer reaching a temperature of 48° C. In a control using CE1MG without sonic energy, a 24 hour exposure yielded less dye in the collection well than the 5 minute exposure with sonic energy.

This example demonstrates that a low cost, low frequency sonic energy transducer can strikingly affect transdermal flux rate when used in conjunction with an appropriate chemical enhancer. Although higher frequency sonic energy will theoretically concentrate more energy in the stratum corneum, when used with a chemical enhancer, the lower frequency modulated sonic energy can accelerate the transdermal flux rate to make the technology useful and practical.

EXAMPLE 23

Demonstration of Molecule Migration Across Human Skin

Tests with the TDK transducer and CE1MG described above were repeated at about 12.4 MHz, one of the highest local resonant peaks for the transducer, with a frequency sweep at a 2 Hz rate from 12.5 to 12.8 MHz and an sonic energy density less than 0.1 W/cm$^2$. The epidermal side of the heat-separated epidermis was facing down, the dye solution was in the lower chamber, and the enhancer solution and the sonic energy were placed in the upper chamber. Within 5 minutes a significant amount of dye had moved across the stratum corneum into the collection well. Ohmic heating in the transducer was significantly less than with the same transducer being driven at 5.4 MHz, causing an increase in temperature of the chemical enhancer to only about 33° C.

Even at these low efficiency levels, the results obtained with CE1MG and sonic energy from the TDK transducer were remarkable in the monitoring direction. FIGS. 3A and 3B of U.S. Pat. No. 5,445,611 show plots of data obtained from three separate cells with the transdermal flux rate measured in the monitoring direction. Even at the 5 minute time point, readily measurable quantities of the dye were present in the chemical enhancer on the outside of the stratum corneum, indicating transport from the epidermal side through the stratum corneum to the "outside" area of the skin sample.

To optimize the use of the sonic energy or the sonic energy/chemical enhancer approach for collecting and monitoring analytes from the body, means for assaying the amount of analyte of interest are required. An assay system that takes multiple readings while the unit is in the process of withdrawing analytes by sonic energy with or without chemical enhancers makes it unnecessary to standardize across a broad population base and normalize for different skin characteristics and flux rates. By plotting two or more data points in time as the analyte concentration in the collection system is increasing, a curve-fitting algorithm can be applied to determine the parameters describing the curve relating analyte withdrawal or flux rate to the point at which equilibrium is reached, thereby establishing the measure of the interval concentration. The general from of this curve is invariant from one individual to another; only the parameters change. Once these parameters are established, solving for the steady state solution (i.e., time equals infinity) of this function, i.e., when full equilibrium is established, provides the concentration of the analyte within the body. Thus, this approach permits measurements to be made to the desired level of accuracy in the same amount of time for all members of a population regardless of individual variations in skin permeability.

Several existing detection techniques currently exist that are adaptable for this application. See, D. A. Christensen, in 1648 Proceedings of Fiber Optic, Medical and Fluorescent Sensors and Applications 223–26 (1992). One method involves the use of a pair of optical fibers that are positioned close together in an approximately parallel manner. One of the fibers is a source fiber, through which light energy is conducted. The other fiber is a detection fiber connected to a photosensitive diode. When light is conducted through the source fiber, a portion of the light energy, the evanescent wave, is present at the surface of the fiber and a portion of this light energy is collected by the detection fiber. The detection fiber conducts the captured evanescent wave energy to the photosensitive diode which measures it. The fibers are treated with a binder to attract and bind the analyte that is to be measured. As analyte molecules bind to the surface (such as the analyte glucose binding to immobilized lectins such as concanavalin A, or to immobilized anti-glucose antibodies) the amount of evanescent wave coupling between the two fibers is changed and the amount of energy captured by the detection fiber and measured by the diode is changed as well. Several measurements of detected evanescent wave energy over short periods of time support a rapid determination of the parameters describing the equilibrium curve, thus making possible calculation of the concentration of the analyte within the body. The experimental results showing measurable flux within 5 minutes (FIGS. 3A and 3B of U.S. Pat. No. 5,445,611) with this system suggest sufficient data for an accurate final reading are collected within 5 minutes.

In its most basic embodiment, a device that can be utilized for the application of sonic energy and collection of analyte comprises an absorbent pad, either of natural or synthetic material, which serves as a reservoir for the chemical enhancer, if used, and for receiving the analyte from the skin surface. The pad or reservoir is held in place, either passively or aided by appropriate fastening means, such as a strap or adhesive tape, on the selected area of skin surface.

An sonic energy transducer is positioned such that the pad or reservoir is between the skin surface and the transducer, and held in place by appropriate means. A power supply is coupled to the transducer and activated by switch means or any other suitable mechanism. The transducer is activated to deliver sonic energy modulated in frequency, phase or intensity, as desired, to deliver the chemical enhancer, if used, from the reservoir through the skin surface followed by collection of the analyte from the skin surface into the reservoir. After the desired fixed or variable time period, the transducer is deactivated. The pad or reservoir, now containing the analyte of interest, can be removed to quantitate the analyte, for example, by a laboratory utilizing any number of conventional chemical analyses, or by a portable device. Alternately, the mechanism for quantitating the analyte can be build into the device used for collection of the analyte, either as an integral portion of the device or as an attachment. Devices for monitoring an analyte are described in U.S. Pat. No. 5,458,140, which is incorporated herein by reference.

EXAMPLE 24

An alternate method for detection of an analyte, such as glucose, following the sample collection through the porated skin surface as described above, can be achieved through the use of enzymatic means. Several enzymatic methods exist for the measurement of glucose in a biological sample. One method involves oxidizing glucose in the sample with glucose oxidase to generate gluconolactone and hydrogen peroxide. In the presence of a colorless chromogen, the hydrogen peroxide is then converted by peroxidase to water and a colored product.

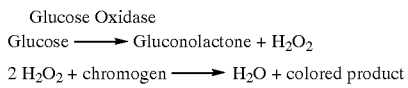

$$\text{Glucose} \xrightarrow{\text{Glucose Oxidase}} \text{Gluconolactone} + H_2O_2$$

$$2\ H_2O_2 + \text{chromogen} \longrightarrow H_2O + \text{colored product}$$

The intensity of the colored product will be proportional to the amount of glucose in the fluid. This color can be determined through the use of conventional absorbance or reflectance methods. By calibration with known concentrations of glucose, the amount of color can be used to determine the concentration of glucose in the collected analyte. By testing to determine the relationship, one can calculate the concentration of glucose in the blood of the subject. This information can then be used in the same way that the information obtained from a blood glucose test from a finger puncture is used. Results can be available within five to ten minutes.

EXAMPLE 25

Any system using a visual display or readout of glucose concentration will indicate to a diagnostician or patient the need for administration of insulin or other appropriate medication. In critical care or other situations where constant monitoring is desired and corrective action needs to be taken almost concurrently, the display may be connected with appropriate signal means which triggers the administration of insulin or other medication in an appropriate manner. For example, there are insulin pumps which are implanted into the peritoneum or other body cavity which can be activated in response to external or internal stimuli. Alternatively, utilizing the enhanced transdermal flux rates possible with micro-poration of the stratum corneum and other techniques described in this invention, an insulin delivery system could be implemented transdermally, with control of the flux rates modulated by the signal from the glucose sensing system. In this manner a complete biomedical control system can be available which not only monitors and/or diagnoses a medical need but simultaneously provides corrective action.

Biomedical control systems of a similar nature could be provided in other situations such as maintaining correct electrolyte balances or administering analgesics in response to a measured analyte parameter such as prostaglandins.

EXAMPLE 26

Similar to audible sound, sonic waves can undergo reflection, refraction, and absorption when they encounter another medium with dissimilar properties [D. Bommannan et al., 9 *Pharm. Res.* 559 (1992)]. Reflectors or lenses may be used to focus or otherwise control the distribution of sonic energy in a tissue of interest. For many locations on the human body, a fold of flesh can be found to support this system. For example, an earlobe is a convenient location which would allow use of a reflector or lens to assist in exerting directional control (e.g., "pushing" of analytes or permeants through the porated stratum corneum) similar to what is realized by changing sonic frequency and intensity.

EXAMPLE 27

Multiple sonic energy transducers may be used to selectively direct the direction of transdermal flux through porated stratum corneum either into the body or from the body. A fold of skin such as an earlobe allow transducers to be located on either side of the fold. The transducers may be energized selectively or in a phased fashion to enhance transdermal flux in the desired direction. An array of transducers or an acoustic circuit may be constructed to use phased array concepts, similar to those developed for radar and microwave communications systems, to direct and focus the sonic energy into the area of interest.

EXAMPLE 28

In this example, the procedure of Example 19 is followed with the exception that the heat-separated epidermis samples are first treated with an excimer laser (e.g. model EMG/200 of Lambda Physik; 193 nm wavelength, 14 ns pulsewidth) to ablate the stratum corneum according to the procedure described in U.S. Pat. No. 4,775,361, hereby incorporated by reference.

EXAMPLE 29

In this example, the procedure of Example 19 is followed with the exception that the heat-separated epidermis samples are first treated with 1,1'-diethyl4,4'-carbocyanine iodide (Aldrich, $\lambda_{max}$=703 nm) and then a total of 70 mJ/cm$^2$/50 ms is delivered to the dye-treated sample with a model TOLD9150 diode laser (Toshiba America Electronic, 30 mW at 690 nm) to ablate the stratum corneum.

EXAMPLE 30

In this example, the procedure of Example 29 is followed with the exception that the dye is indocyanine green (Sigma cat. no. I-2633; $\lambda_{max}$=775 nm) and the laser is a model Diolite 800-50 (LiCONiX, 50 mW at 780 nm).

EXAMPLE 31

In this example, the procedure of Example 29 is followed with the exception that the dye is methylene blue and the laser is a model SDL-8630 (SDL Inc.; 500 mW at 670 nm).

EXAMPLE 32

In this example, the procedure of Example 29 is followed with the exception that the dye is contained in a solution comprising a permeation enhancer, e.g. CE1.

EXAMPLE 33

In this example, the procedure of Example 29 is followed with the exception that the dye and enhancer-containing solution are delivered to the stratum corneum with the aid of exposure to ultrasound.

EXAMPLE 34

In this example, the procedure of Example 31 is followed with the exception that the pulsed light source is a short arc lamp emitting over the broad range of 400 to 100 nm but having a bandpass filter placed in the system to limit the output to the wavelength region of about 650 to 700 nm.

EXAMPLE 35

In this example, the procedure of Example 19 is followed with the exception that the heat-separated epidermis samples are first punctured with a microlancet (Becton Dickinson) calibrated to produce a micropore in the stratum corneum without reaching the underlying tissue.

EXAMPLE 36

In this example, the procedure of Example 19 is followed with the exception that the heat-separated epidermis samples are first treated with focused sonic energy in the range of 70–480 mJ/cm$^2$/50 ms to ablate the stratum corneum.

EXAMPLE 37

In this example, the procedure of Example 19 is followed with the exception that the stratum corneum is first punctured hydraulically with a high pressure jet of fluid to form a micropore of up to about 100 µm diameter.

EXAMPLE 38

In this example, the procedure of Example 19 is followed with the exception that the stratum corneum is first punctured with short pulses of electricity to form a micropore of up to about 100 µm diameter.

EXAMPLE 39

Acoustic Streaming

A new mechanism and application of sonic energy in the delivering of therapeutic substances into the body and/or harvesting fluids from within the body into an external reservoir through micro-porations formed in the stratum corneum layer will now be described. An additional aspect of this invention is the utilization of sonic energy to create an acoustic streaming effect on the fluids flowing around and between the intact cells in the epidermis and dermis of the human skin. Acoustic streaming is a well documented mode by which sonic energy can interact with a fluid medium. Nyborg, Physical Acoustics Principles and Methods, p. 265–331, Vol II-Part B, Academic Press, 1965. The first theoretical analysis of acoustic streaming phenomenon was given by Rayleigh (1884, 1945). In an extensive treatment of the subject, Longuet-Higgins (1953–1960) has given a result applicable to two dimensional flow that results in the near vicinity of any vibrating cylindrical surface. A three dimensional approximation for an arbitrary surface was developed by Nyborg (1958). As described by Fairbanks et al., 1975 Ultrasonics Symposium Proceedings, IEEE Cat. #75, CHO 994-4SU, sonic energy, and the acoustic streaming phenomenon can be of great utility in accelerating the flux of a fluid through a porous medium, showing measurable increases in the flux rates by up to 50 times that possible passively or with only pressure gradients being applied.

All previous transdermal delivery or extraction efforts utilizing ultrasound have focused on methods of interaction between the sonic energy and the skin tissues designed to permeabilize the stratum corneum layer. The exact mode of interaction involved has been hypothesized to be due exclusively to the local elevation of the temperature in the SC layer, and the resultant melting of the lipid domains in the intercellular spaces between the corneocytes. Srinivasan et al. Other researchers have suggested that micro-cavitations and or shearing of the structures in the stratum corneum opens up channels through which fluids may flow more readily. In general, the design of the sonic systems for the enhancement of transdermal flux rates has been based on the early realization that the application of an existing therapeutic ultrasound unit designed to produce a "deep-heating" effect on the subject, when used in conjunction with a topical application of a gelled or liquid preparation containing the drug to be delivered into the body, could produce a quantifiable increase in the flux rate of the drug into the body in the context of the method taught herein to create micropores in this barrier layer, the use of sonic energy may now be thought of in a totally new and different sense than the classically defined concepts of sonophoresis.

Based on the experimental discovery mentioned in U.S. Pat. Nos. 5,458,140 and 5,445,611 that when a small hole existed or was created in the stratum corneum (SC) in the Franz cells used in the in vitro studies, that the application of an appropriately driven ultrasonic transducer to the fluid reservoir on either side of the porated SC sample, an "acoustic streaming" event could be generated wherein large flux rates of fluid where capable of being pumped through this porated membrane.

With the method taught herein to create the controlled micro-porations in the stratum corneum layer in the living subject's skin, the application of the fluid streaming mode of sonic/fluid interaction to the induction of fluid into or out of the body may now be practically explored. For example, clinical studies have shown that by making a series of four 80 $\mu$m diameter micro-pores in a 400 $\mu$m square, and then applying a mild (10 to 12 inches of Hg) suction to this area, an average of about 1 $\mu$l of interstitial fluid can be induced to leave the body for external collection in an external chamber. By adding a small, low power sonic transducer to this system, configured such that it actively generates inwardly converging concentric circular pressure waves in the 2 to 6 mm of tissue surrounding the poration site, it has been demonstrated that this ISF flux rate can be increased by 50%.

By relieving ourselves of the desire to create some form of direct absorption of sonic energy in the skin tissues (as required to generate heating), frequencies of sonic energy can be determined for which the skin tissues are virtually transparent, that is at the very low frequency region of 1 kHz to 500 KHz. Even at some of the lowest frequencies tested, significant acoustic streaming effects could be observed by using a micro-scope to watch an in vivo test wherein the subject's skin was micro-porated and ISF was induced to exit the body an pool on the surface of the skin. Energizing the sonic transducer showed dramatic visual indications of the amount of acoustic streaming as small pieces of particulate matter were carried along with the ISF as it swirled about. Typical magnitude of motion exhibited can be described as follows: for a 3 mm diameter circular pool of ISF on the surface of the skin, a single visual particle could be seen to be completing roughly 3 complete orbits per second. This equates to a linear fluid velocity of more than 2.5 mm/second. All of this action was demonstrated with sonic power levels into the tissues of less than 100 mW/cm2.

Figure 30:
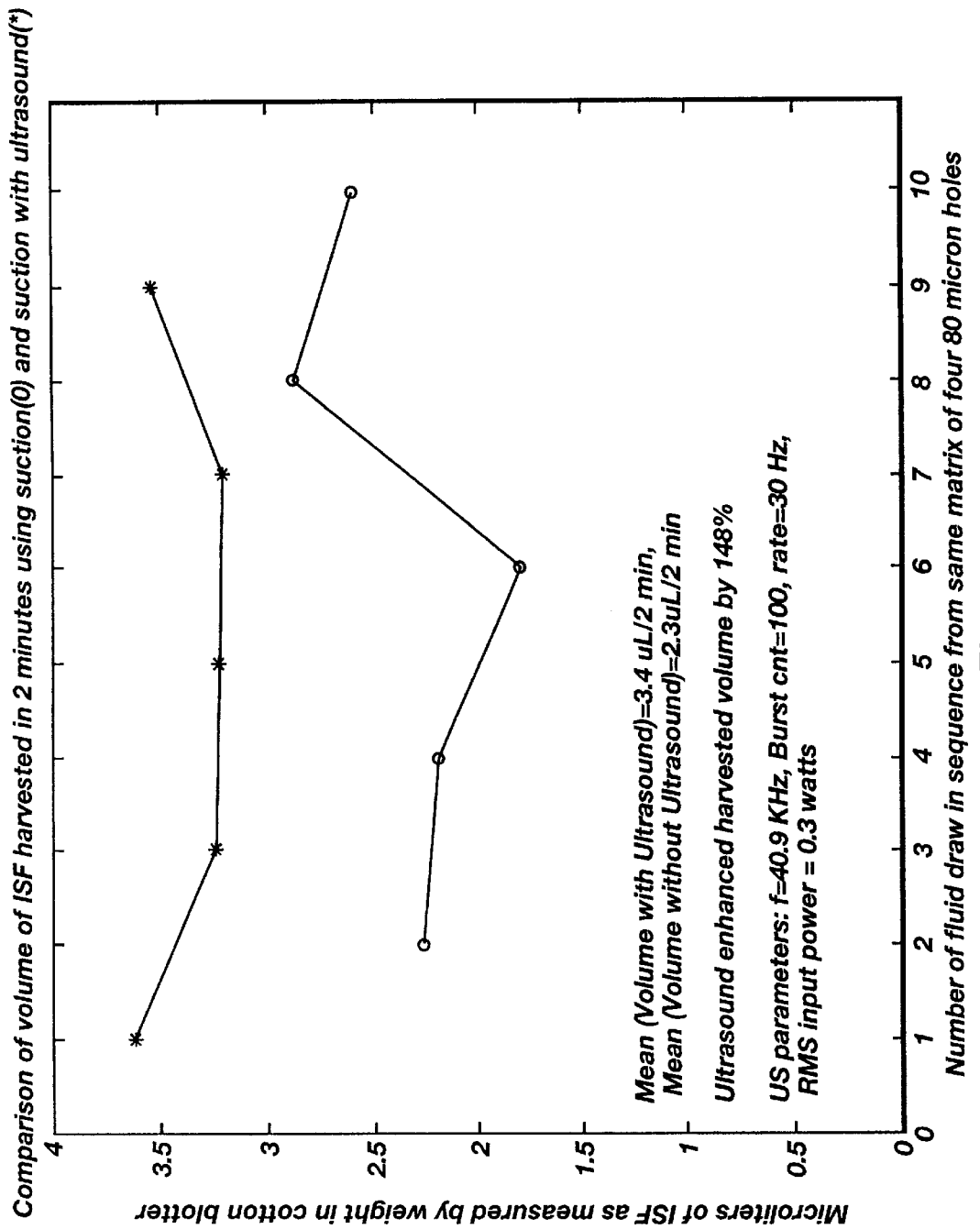
FIG. 30 shows a plot comparing the amount of interstitial fluid harvested from micropores with suction alone (○) and with a combination of suction and ultrasound (*).

While one can easily view the top surface of the skin, and the fluidic activity thereon, assessing what is taking place dynamically within the skin tissue layers in response to the coupling into these tissues of sonic energy is much more difficult. One can assume, that if such large fluid velocities (e.g. >2.5 mm/S) may be so easily induced on the surface, then some noticeable increase in the fluid flow in the intercellular channels present in the viable dermal tissues could also be realized in response to this sonic energy input. Currently, an increase in harvested ISF through a given set of incorporations when a low frequency sonic energy was applied to the area in a circle surrounding the poration sites has been quantified. In this experiment, an ISF harvesting technique based solely on a mild suction (10 to 12 inches of HG) was alternated with using the exact same apparatus, but with the sonic transducer engaged. Over a series of 10 two-minute harvesting periods, five with mere suction and five with both suction and sonic energy active, it was observed that by activating the sonic source roughly 50% more ISF was collectable in the same time period. These data are shown in FIG. 30. This increase in ISF flux rate was realized with no reported increase in sensation from the test subject due to the sonic energy. The apparatus used for this experiment is illustrated in FIGS. 31–33. The transducer assembly in FIGS. 31–33 is comprised of a thick walled cylinder of piezo-electric material, with an internal diameter of roughly 8 mm and a wall thickness of 4 mm. The cylinder has been polarized such that when an electrical field is applied across the metalized surfaces of the outer diameter and inner diameter, the thickness of the wall of the cylinder expands or contracts in response to the field polarity. In practice, this configuration results in a device which rapidly squeezes the tissue which has been suctioned into the central hole, causing an inward radial acoustic streaming effect on those fluids present in these tissues. This inward acoustic streaming is responsible for bringing more ISF to the location of the micro-porations in the center of the hole, where it can leave the body for external collection.

A similar device shown in FIGS. 34A–B was built and tested and produced similar initial results. In the FIGS. 34A–B version, an ultrasonic transducer built by Zevex, Inc. Salt Lake City, Utah, was modified by having a spatulate extension added to the sonic horn. A 4 mm hole was placed in the 0.5 mm thick spatulate end of this extension. When activated, the principle motion is longitudinal along the length of the spatula, resulting in essentially a rapid back and forth motion. The physical perturbation of the metalic spatula caused by the placement of the 4 mm hole, results in a very active, but chaotic, large displacement behavior at this point. In use, the skin of the subject was suctioned up into this hole, and the sonic energy was then cunductined into the skin in a fashion similar to that illustrated in FIG. 33.

The novel aspect of this new application of ultrasound lies in the following basic areas:

1. The function of the ultrasound is no longer needed to be focused on permeabilizing the SC barrier membrane as taught by Langer, Kost, Bommannan and others.

2. A much lower frequency system can be utilized which has very little absorption in the skin tissues, yet can still create the fluidic streaming phenomenon desired within the intercellular passageways between the epidermal cells which contain the interstitial fluid.

3. The mode of interaction with the tissues and fluids therein, is the so-called "streaming" mode, recognized in the sonic literature as a unique and different mode than the classical vibrational interactions capable of shearing cell membranes and accelerating the passive diffusion process.

By optimizing the geometric configuration, frequency, power and modulations applied to the sonic transducer, it has been shown that significant increases in the fluid flux through the porated skin sites can be achieved. The optimization of these parameters is designed to exploit the non-linearities governing the fluid flow relationships in this microscopically scaled environment. Using frequencies under 200 kHz, large fluidic effects can be observed, without any detectable heating or other negative tissue interactions. The sonic power levels required to produce these measurable effects are very low, with average power levels typically under 100 milliwatts/cm2.

Therefore, the above examples are but representative of systems which may be employed in the utilization of ultrasound or ultrasound and chemical enhancers in the collection and quantification of analytes for diagnostic purposes and for the transdermal delivery of permeants. The invention is directed to the discovery that the poration of the stratum corneum followed by the proper use of ultrasound, particularly when accompanied with the use of chemical enhancers, enables the noninvasive or minimally invasive transdermal determination of analytes or delivery of permeants. However, the invention is not limited only to the specific illustrations. There are numerous poration techniques and enhancer systems, some of which may function better than another, for detection and withdrawn of certain analytes or delivery of permeants through the stratum corneum. However, within the guidelines presented herein, a certain amount of experimentation to obtain optimal poration, enhancers, or optimal time, intensity and frequency of applied ultrasound, as well as modulation of frequency, amplitude and phase of applied ultrasound can be readily carried out by those skilled in the art. Therefore, the invention is limited in scope only by the following claims and functional equivalents thereof.

What is claimed is:

1. An apparatus for forming micropores in a selected area of the stratum corneum for enhancing the permeability of the skin, the apparatus comprising a heat conducting element to be placed in substantial physical contact with the selected area to deliver sufficient energy by conduction to said selected area such that the temperature of tissue-bound water and other vaporizable substances in said selected area is elevated above the vaporization point of said water and other vaporizable substances thereby removing the stratum corneum and forming at least one micropore 1–1000 $\mu$m across in said selected area of said stratum corneum.

2. The apparatus of claim 1, wherein the heat conducting element comprises an effective amount of an energy-absorbing compound that exhibits absorption over a predetermined frequency range of electromagnetic energy, and further comprising a pulsed light source capable of emitting electromagnetic energy in the predetermined frequency range, wherein the pulsed light source is focused onto said energy-absorbing compound such that said energy-absorbing compound is heated sufficiently to conductively transfer heat to said stratum corneum.

3. The apparatus of claim 2, wherein the heat conducting element comprises a film treated with said energy-absorbing compound.

4. The apparatus of claim 2, wherein the heat conducting element comprises a solid support comprising on one side an adhesive that is treated with said energy-absorbing compound.

5. The apparatus of claim 2, and further comprising a chemical enhancer combined with said energy-absorbing compound.

6. The apparatus of claim 2, and further comprising a controller coupled to the pulsed light source that controls said pulsed light source to emit pulses at a wavelength that is not significantly absorbed by the stratum corneum.

7. The apparatus of claim 6, wherein the controller controls the duration of a pulse on-time and the duration of a pulse off-time of a cycle of the pulsed light source so as to reduce the sensation to the individual.

8. The apparatus of claim 6, wherein the controller controls the duration of the pulse on-time to be less than 50 milliseconds and the duration of the pulse off-time to be greater than 10 milliseconds.

9. The apparatus of claim 2, wherein the pulsed light source comprises a laser diode emitting in the range of about 630 to 1550 nm.

10. The apparatus of claim 2, wherein the pulsed light source comprises a laser diode pumped optical parametric oscillator emitting in the range of about 700 to 3000 nm.

11. The apparatus of claim 2, wherein the pulsed light source is a member selected from the group consisting of arc lamps, incandescent lamps, and light emitting diodes.

12. The apparatus of claim 2, and further comprising means for sensing when the barrier properties of the stratum corneum have been surmounted.

13. The apparatus of claim 12, wherein the means for sensing comprises a sensor that receives reflected light from said selected area and a controller coupled to the sensor and to the pulsed light source that measures a quality of said reflected light and terminates output of the pulse light source based upon the quality of the reflected light.

14. The apparatus of claim 1, and further comprising a cooling device suitable for being disposed around said selected area to cool said selected area of stratum corneum and adjacent skin tissues to a selected cooled condition.

15. The apparatus of claim 14, wherein the cooling device comprises a Peltier device.

16. The apparatus of claim 1, wherein the heat conducting element comprises a solid probe.

17. The apparatus of claim 16, and further comprising a heat source coupled to the solid probe, wherein the heat source is an ohmic heating element.

18. The apparatus of claim 16, and further comprising means for modulating the temperature of said selected area of the stratum corneum with the solid probe.

19. The apparatus of claim 18, wherein the means for modulating heats the selected area of the stratum corneum to greater than 123° C. for less than 50 milliseconds for an on-time of a cycle and returns the temperature of the selected area of the stratum corneum to approximately ambient temperature for more than 10 milliseconds for an off-time of a cycle.

20. The apparatus of claim 18, wherein the means for modulating comprises a mechanical element capable of alternately applying and withdrawing the solid probe in contact with the surface of the stratum corneum.

21. The apparatus of claim 16, and further comprising a controller coupled to the solid probe and to the skin, the controller determining the depth of said micropore by monitoring electrical impedance between said solid probe and the biological organism through said selected area of stratum corneum and adjacent skin tissues, and wherein the controller controls a mechanical element to withdraw said solid thermal probe from contact with the stratum corneum when a predetermined change in impedance associated with contacting an epidermal layer underlying the stratum corneum is detected.

22. The apparatus of claim 16, wherein the solid probe comprises a current loop having a high resistance point.

23. The apparatus of claim 22, and further comprising a current source coupled to the current loop and a controller coupled to the current source, wherein the controller modulates the current supplied by the current source to the current loop.

24. The apparatus of claim 16, wherein the solid probe comprises a wire.

25. The apparatus of claim 24, and further comprising an excitation coil arranged such that the wire is positioned within the excitation coil and a controller coupled to the excitation coil, the controller controlling an alternating magnetic field of the excitation coil such that energizing the excitation coil with alternating current produces eddy currents sufficient to heat the solid thermal probe by internal ohmic losses.

26. The apparatus of claim 1, and further comprising means for applying sonic energy to said selected area at a frequency in the range of 5 kHz to 100 MHZ to further enhance the permeability of the skin.

27. The apparatus of claim 26, wherein said means for applying sonic energy further comprises means for modulating the sonic energy by frequency modulation, amplitude modulation, phase modulation, or combinations thereof.

28. The apparatus of claim 1, and further comprising means for applying a pressure gradient to said selected area of stratum corneum for enhancing exudation of biological fluid.

29. The apparatus of claim 28, wherein the means for applying a pressure gradient comprises a suction device for applying a vacuum to said selected area of the stratum corneum.

30. The apparatus of claim 1, and further comprising means for collecting biological fluid from said selected area of the stratum corneum.

31. The apparatus of claim 30, and further comprising means for quantitating an analyte in the biological fluid.

32. The apparatus of claim 31, wherein the means for quantitating comprises a glucose assay strip.

33. The apparatus of claim 1, and further comprising means for delivering a composition comprising an effective amount of a permeant through the at least one micropore.

* * * * *